US012569134B2

(12) United States Patent
Yamaguchi et al.

(10) Patent No.: US 12,569,134 B2
(45) Date of Patent: Mar. 10, 2026

(54) OPHTHALMIC APPARATUS, METHOD OF CONTROLLING OPHTHALMIC APPARATUS, AND RECORDING MEDIUM

(71) Applicant: Topcon Corporation, Tokyo (JP)

(72) Inventors: Tatsuo Yamaguchi, Tokyo (JP); Ryo Bando, Tokyo (JP)

(73) Assignee: TOPCON CORPORATION, Tokyo (JP)

( * ) Notice: Subject to any disclaimer, the term of this patent is extended or adjusted under 35 U.S.C. 154(b) by 636 days.

(21) Appl. No.: 17/882,600

(22) Filed: Aug. 8, 2022

(65) Prior Publication Data

US 2024/0041323 A1        Feb. 8, 2024

(51) Int. Cl.
*A61B 3/14*        (2006.01)
*A61B 3/00*        (2006.01)
*G06T 7/00*        (2017.01)
(52) U.S. Cl.
CPC .............. *A61B 3/14* (2013.01); *A61B 3/0008* (2013.01); *A61B 3/0025* (2013.01); *G06T 7/0014* (2013.01); *G06T 2207/30041* (2013.01)
(58) Field of Classification Search
CPC ....... A61B 3/14; A61B 3/0008; A61B 3/0025; G06T 7/0014; G06T 2207/30041
(Continued)

(56) References Cited

U.S. PATENT DOCUMENTS 5,321,446 A        6/1994   Massig et al.
5,726,735 A        3/1998   Kawamura et al.
(Continued)

FOREIGN PATENT DOCUMENTS

EP        3449810 A1        3/2019
JP        H08206070 A        8/1996
(Continued)

OTHER PUBLICATIONS

Qian et al., "In vivo quantitative analysis of anterior chamber white blood cell mixture composition using spectroscopic optical coherence tomography", Biomedical Optics Express, vol. 12, No. 4, Apr. 1, 2021, pp. 2134-2148.
(Continued)

*Primary Examiner* — Mohammed A Hasan
(74) *Attorney, Agent, or Firm* — XSENSUS LLP

(57)        ABSTRACT

An ophthalmic apparatus according to an embodiment includes an illumination system configured to project illumination light onto a subject's eye, and a photography system configured to perform photography of the subject's eye. The illumination system and the photography system are configured to satisfy a Scheimpflug condition. The illumination system includes a light source unit configured to output slit illumination light, and an illumination polarizer configured to extract an illumination polarization component from the slit illumination light. The illumination system is further configured to project the illumination polarization component onto the subject's eye. The photography system includes a photography polarizer configured to extract a photography polarization component from return light from the subject's eye with the slit illumination light projected, and an image sensor configured to detect the photography polarization component.

29 Claims, 39 Drawing Sheets

(58) Field of Classification Search
USPC ........................................................ 351/221
See application file for complete search history.

(56) References Cited

U.S. PATENT DOCUMENTS

| 11,596,303 | B1 | 3/2023 | Shen et al. | |
| 2002/0101567 | A1* | 8/2002 | Sumiya | A61B 3/156 |
| | | | | 351/206 |
| 2011/0267582 | A1* | 11/2011 | Endo | G06V 40/19 |
| | | | | 351/206 |
| 2012/0229617 | A1* | 9/2012 | Yates | A61B 3/1208 |
| | | | | 348/78 |
| 2021/0152740 | A1* | 5/2021 | Abe | H04N 5/907 |
| 2022/0248953 | A1* | 8/2022 | Shimizu | A61B 3/14 |
| 2024/0260931 | A1 | 8/2024 | Kato | |

FOREIGN PATENT DOCUMENTS

| JP | 2004236937 | A | 8/2004 |
| JP | 2016-159073 | A | 9/2016 |
| JP | 2016-179004 | A | 10/2016 |
| JP | 2019042304 | A | 3/2019 |
| JP | 2019-213733 | A | 12/2019 |
| JP | 70481440 | B1 | 4/2022 |
| WO | 2009100866 | A1 | 8/2009 |
| WO | 2019/240149 | A1 | 12/2019 |
| WO | 2021161030 | A1 | 8/2021 |

OTHER PUBLICATIONS

Li, Xiaoran, et al., "Simultaneous optical coherence tomography and Scheimpflug imaging using the same incident light", Optics Express, Dec. 21, 2020, vol. 28, No. 26, pp. 39660-39676.
Japanese Office Action issued Oct. 7, 2025, in corresponding Japanese Patent Application No. 2024-540312, 10pp.
English translation of the International Search Report (Appl. No. Pct/JP2023/025099) issued Sep. 19, 2023, 3pp.

* cited by examiner

OUTPUT OF ILLUMINATION LIGHT
TOP: ON
BOTTOM: OFF

EXPOSURE OF IMAGE SENSOR
TOP: EXPOSURE
BOTTOM: CHARGE TRANSFER /
EXPOSURE STANDBY

SCAN POSITION
TOP: SCAN END POSITION
BOTTOM: SCAN START POSITION

TIME t

OUTPUT OF ILLUMINATION LIGHT
TOP: ON
BOTTOM: OFF

EXPOSURE OF IMAGE SENSOR
TOP: EXPOSURE
BOTTOM: CHARGE TRANSFER /
EXPOSURE STANDBY

SCAN POSITION
TOP: SCAN END POSITION
BOTTOM: SCAN START POSITION

→ TIME t

OUTPUT OF ILLUMINATION LIGHT
TOP: PROJECTION PERIOD
BOTTOM: NON-PROJECTION PERIOD

EXPOSURE OF IMAGE SENSOR
TOP: EXPOSURE PERIOD
BOTTOM: NON-EXPOSURE PERIOD

FIG. 7B

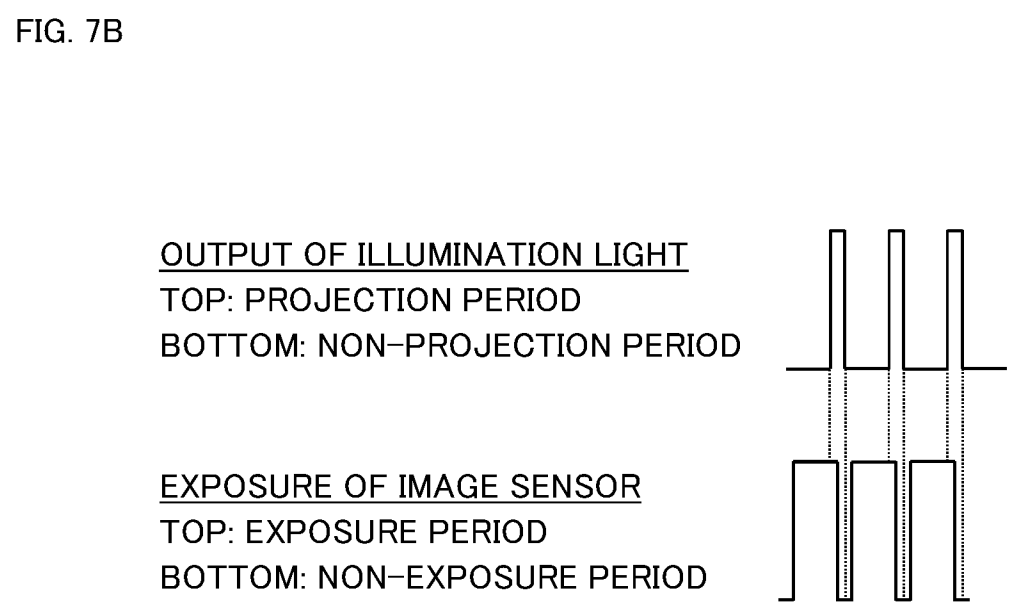

OUTPUT OF ILLUMINATION LIGHT
TOP: PROJECTION PERIOD
BOTTOM: NON-PROJECTION PERIOD

EXPOSURE OF IMAGE SENSOR
TOP: EXPOSURE PERIOD
BOTTOM: NON-EXPOSURE PERIOD

START

S1  PERFORM PHOTOGRAPHY WITH ILLUMINATION POLARIZER AND PHOTOGRAPHY POLARIZER ARRANGED IN CROSSED NICOLS

S2  PERFORM PHOTOGRAPHY WITH ILLUMINATION POLARIZER AND PHOTOGRAPHY POLARIZER ARRANGED IN PARALLEL NICOLS

S3  GENERATE IMAGE CONTAINING NO SPECULAR REFLECTION NOISE BASED ON DIFFUSE REFLECTION IMAGE AND SPECULAR REFLECTION IMAGE

END

START

S11  PERFORM PHOTOGRAPHY WITH ILLUMINATION POLARIZER AND PHOTOGRAPHY POLARIZER ARRANGED IN CROSSED NICOLS

S12  PERFORM PHOTOGRAPHY WITH ILLUMINATION POLARIZER AND PHOTOGRAPHY POLARIZER ARRANGED IN PARALLEL NICOLS

S13  PERFORM COMPARATIVE ANALYSIS BETWEEN DIFFUSE REFLECTION IMAGE AND SPECULAR REFLECTION IMAGE

END

OPHTHALMIC APPARATUS, METHOD OF CONTROLLING OPHTHALMIC APPARATUS, AND RECORDING MEDIUM

FIELD

The present disclosure relates generally to an ophthalmic apparatus, a method of controlling the same, and a recording medium.

BACKGROUND

Diagnostic imaging serves an important role in the field of ophthalmology. Ophthalmic diagnostic imaging uses various kinds of ophthalmic apparatuses. Types of or kinds examples of ophthalmic apparatuses include a slit lamp microscope, a fundus camera, a scanning laser ophthalmoscope (SLO), an optical coherence tomography (OCT) apparatus, and the like. In addition, various kinds of ophthalmic examination apparatuses and ophthalmic measurement apparatuses, such as a refractometer, a keratometer, a tonometer, a specular microscope, a wavefront analyzer, and a microperimeter, are equipped with a function of imaging anterior eye segment, eye fundus, etc.

A slit lamp microscope, also known as the stethoscope for ophthalmologists, is one of the most widely and frequently utilized apparatuses among such various kinds of ophthalmic apparatuses. A slit lamp microscope is used for illuminating a subject's eye with slit light and observing and/or photographing the illuminated cross section from an oblique or side position with a microscope (see, for example, Patent Documents 1 and 2 below). Further, also known is a slit lamp microscope that is capable of scanning a three dimensional region of the subject's eye at relatively high speed by using an optical system configured to satisfy the Scheimpflug condition (see, for example, Patent Document 3 below). In addition to a slit lamp microscope, a rolling shutter camera or the like is also known as an imaging technique for scanning an object with slit light.

PATENT DOCUMENT 1: Japanese Unexamined Patent Application Publication No. 2016-159073

PATENT DOCUMENT 2: Japanese Unexamined Patent Application Publication No. 2016-179004

PATENT DOCUMENT 3: Japanese Unexamined Patent Application Publication No. 2019-213733 (International Publication No. WO 2019/240149)

BRIEF SUMMARY

An object of the present disclosure is to provide an improvement in ophthalmic imaging.

An aspect example of an embodiment is an ophthalmic apparatus including: an illumination system configured to project illumination light onto a subject's eye; and a photography system configured to perform photography of the subject's eye, wherein the illumination system and the photography system are configured to satisfy a Scheimpflug condition, the illumination system includes a light source unit configured to output slit illumination light and an illumination polarizer configured to extract an illumination polarization component from the slit illumination light output by the light source unit, and the illumination system is configured to project the illumination polarization component extracted by the illumination polarizer onto the subject's eye as the illumination light, and the photography system includes a photography polarizer configured to extract a photography polarization component from return light from the subject's eye with the slit illumination light projected and an image sensor configured to detect the photography polarization component extracted by the photography polarizer.

Another aspect example of an embodiment is a method of controlling an ophthalmic apparatus that includes an illumination system configured to project slit illumination light onto a subject's eye, a photography system configured to perform photography of the subject's eye, a movement mechanism configured to move the illumination system and the photography system, and a processor, wherein the illumination system and the photography system are configured to satisfy a Scheimpflug condition, the illumination system includes a light source unit configured to output slit illumination light and an illumination polarizer configured to extract an illumination polarization component from the slit illumination light output by the light source unit, the illumination system is configured to project the illumination polarization component extracted by the illumination polarizer onto the subject's eye as the illumination light, and the photography system includes a photography polarizer configured to extract a photography polarization component from return light from the subject's eye with the slit illumination light projected and an image sensor configured to detect the photography polarization component extracted by the photography polarizer, the method including causing the processor to perform at least control of the photography system and control of the movement mechanism to cause the photography system to collect a series of images.

A further aspect example of an embodiment is a program configured to cause a computer to execute control of an ophthalmic apparatus that includes an illumination system configured to project slit illumination light onto a subject's eye, a photography system configured to perform photography of the subject's eye, and a movement mechanism configured to move the illumination system and the photography system, wherein the illumination system and the photography system are configured to satisfy a Scheimpflug condition, the illumination system includes a light source unit configured to output slit illumination light and an illumination polarizer configured to extract an illumination polarization component from the slit illumination light output by the light source unit, the illumination system is configured to project the illumination polarization component extracted by the illumination polarizer onto the subject's eye as the illumination light, and the photography system includes a photography polarizer configured to extract a photography polarization component from return light from the subject's eye with the slit illumination light projected and an image sensor configured to detect the photography polarization component extracted by the photography polarizer, the program including an instruction for causing the computer to perform at least control of the photography system and control of the movement mechanism to cause the photography system to collect a series of images.

A yet further aspect example of an embodiment is a computer-readable non-transitory recording medium storing a program configured to cause a computer to execute control of an ophthalmic apparatus that includes an illumination system configured to project slit illumination light onto a subject's eye, a photography system configured to perform photography of the subject's eye, and a movement mechanism configured to move the illumination system and the photography system, wherein the illumination system and the photography system are configured to satisfy a Scheimpflug condition, the illumination system includes a light source unit configured to output slit illumination light and an illumination polarizer configured to extract an illumination polarization component from the slit illumination light output by the light source unit, the illumination system is configured to project the illumination polarization component extracted by the illumination polarizer onto the subject's eye as the illumination light, and the photography system includes a photography polarizer configured to extract a photography polarization component from return light from the subject's eye with the slit illumination light projected and an image sensor configured to detect the photography polarization component extracted by the photography polarizer, the program stored in the computer-readable non-transitory recording medium including an instruction for causing the computer to perform at least control of the photography system and control of the movement mechanism to cause the photography system to collect a series of images.

Some embodiments are capable of providing an improvement in ophthalmic imaging.

BRIEF DESCRIPTION OF THE SEVERAL VIEWS OF THE DRAWING

FIG. 7B is a timing chart illustrating processing executed by an ophthalmic apparatus according to an aspect example of an embodiment.

DETAILED DESCRIPTION

Figure 1:
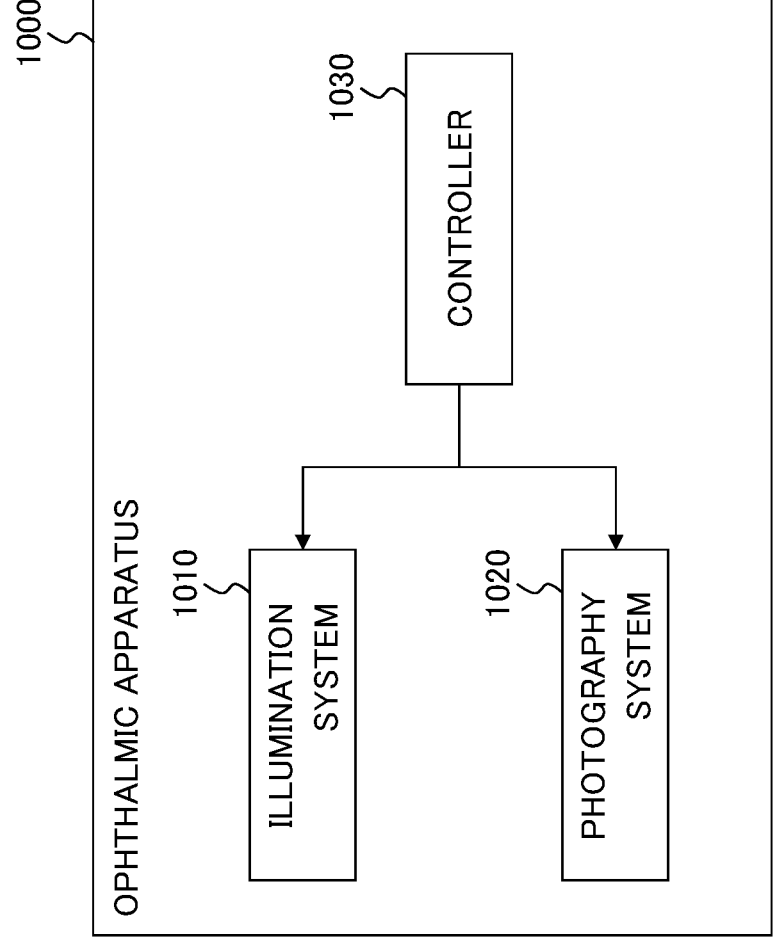
FIG. 1 is a diagram illustrating a configuration of an ophthalmic apparatus according to an aspect example of an embodiment.

Several non-limiting aspect examples of some embodiments according to the present disclosure will be described in detail with reference to the drawings.

Any known technologies or techniques may be incorporated with any aspect according to the present disclosure. For example, any of the matters and/or items disclosed in the literature cited herein may be incorporated and/or combined with any aspect according to the present disclosure. In addition, any known technologies or techniques in any kinds of technical fields related to the present disclosure may be incorporated and/or combined with any aspect according to the present disclosure.

All of the contents (any of the matters and/or items) disclosed in Patent Document 3 (Japanese Unexamined Patent Application Publication No. 2019-213733 (International Publication No. WO 2019/240149)) are incorporated herein by reference. In addition, any technical matters and/or items (e.g., any matters and/or items disclosed in patent applications, papers, etc.) disclosed by the applicant of the present application regarding technologies or techniques relating to the present disclosure may be incorporated and/or combined with any of the aspects according to the present disclosure.

It is also possible to combine, at least in part, any two or more of the various aspects according to the present disclosure.

At least one or more of the functions of the elements described in the present disclosure are implemented by using a circuit configuration (circuitry) or a processing circuit configuration (processing circuitry). The circuitry or the processing circuitry includes any of the followings, all of which are configured and/or programmed to execute at least one or more functions disclosed herein: a general purpose processor, a dedicated processor, an integrated circuit, a central processing unit (CPU), a graphics processing unit (GPU), an application specific integrated circuit (ASIC), a programmable logic device (e.g., a simple programmable logic device (SPLD), a complex programmable logic device (CPLD), or a field programmable gate array (FPGA)), an existing or conventional circuit configuration or circuitry, and any combination of these. A processor is considered to be processing circuitry or circuitry that includes a transistor and/or another circuitry. In the present disclosure, circuitry, a unit, a means, or a term similar to these is hardware that executes at least one or more functions disclosed herein, or hardware that is programmed to execute at least one or more functions disclosed herein. Hardware may be the hardware disclosed herein, or alternatively, known hardware that is programmed and/or configured to execute at least one or more functions described herein. In the case in which the hardware is a processor, which may be considered as a certain type or kind of circuitry, then circuitry, a unit, a means, or a term similar to these is a combination of hardware and software. In this case, the software is used to configure the hardware and/or the processor.

In the following embodiments, various aspects in the case of dealing with monochrome images, that is, in the case of using a monochrome camera, will be described; however, those skilled in the art will understand that the same or similar processing may also be employed in the case of dealing with color images, that is, in the case of using a color camera. As a non-limiting example of a case in which color images are processed, any one or more of the following methods may be employed considering an actuality that in general color cameras generate three color component images, namely, an R-component image, a G-component image, and a B-component image: a method of generating a high dynamic range image for each component image; a method of generating a high dynamic range image using a brightness signal value (Y signal) generated from the three color component images; a method of generating a high dynamic range image by converting a color image to a monochrome image; and a method of generating a high dynamic range image only from a selected color component image.

<Overview of Embodiment>

An embodiment according to the present disclosure aims to provide an improvement in ophthalmic imaging conducted by using an optical system configured to satisfy the Scheimpflug condition (Scheimpflug principle). As an application, some aspect examples of the embodiment of the present disclosure aim to provide an improvement in ophthalmic imaging in which image acquisition (image collection) is performed while moving an optical system configured to satisfy the Scheimpflug condition.

There are cases in which an image acquired by a conventional ophthalmic apparatus equipped with an optical system that satisfies the Scheimpflug condition contains noise caused by the specular reflection of illumination light projected onto the subject's eye. This noise is referred to as specular reflection noise. For example, an image of specular reflection from a tissue having high reflectivity, such as a cornea, may be mixed as noise.

Techniques or technologies for removing corneal specular reflection noise from an eye image obtained by a modality such as a fundus camera or an optical coherence tomography (OCT) apparatus are widely known. However, to the best of the applicant's knowledge, there is no publicly known ophthalmic apparatus with an optical system satisfying the Scheimpflug condition that has this function of noise removal (noise reduction, noise rejection, noise elimination, or the like).

In particular, an ophthalmic apparatus, which has the above function of noise removal, with an optical system configured to satisfy the Scheimpflug condition and further configured to project slit illumination light onto the subject's eye, has not been publicly known, and also there is no literature that teaches or suggests such an apparatus, to the best of the applicant's knowledge.

Furthermore, with a conventional ophthalmic apparatus equipped with an optical system that satisfies the Scheimpflug condition, relatively excessive reflection from a tissue having high reflectivity may impair the visibility of an image of another tissue. For example, strong reflection from a cornea may impair the visibility of an intraocular tissue such as a crystalline lens.

In addition, a conventional ophthalmic apparatus equipped with an optical system that satisfies the Scheimpflug condition could not provide the polarization characteristics of the subject's eye.

Embodiments according to the present disclosure have been made with at least these issues in mind. However, actions and effects of the embodiments according to the present disclosure, as well as objects to be achieved by the embodiments according to the present disclosure are not limited to matters and/or items related to these issues. The actions, effects, and objects of the embodiments according to the present disclosure may provide an improvement, from various points of views, in imaging performed by using an ophthalmic apparatus having an optical system configured to satisfy the Scheimpflug condition.

To this end, an embodiment according to the present disclosure has the following configuration. That is, an ophthalmic apparatus according to an embodiment includes an illumination system and a photography system, and the illumination system and the photography system are configured to satisfy the Scheimpflug condition.

The illumination system of the embodiment includes a light source unit and a polarizer. The light source unit is configured to output slit illumination light and the polarizer is configured to extract a predetermined polarization component from the slit illumination light output by the light source unit. The illumination system is further configured to project the polarization component extracted by the polarizer onto the subject's eye as illumination light.

In some aspect examples, the slit illumination light may be a light beam having a cross sectional shape that is formed roughly into a line shape in a macroscopic sense and into an elongated rectangular shape in a microscopic sense, such as a light beam whose cross sectional shape is formed by a slit.

The configuration of the light source unit that generates the slit illumination light may be freely determined. In some examples, the light source unit that generates the slit illumination light may be any of the followings: a light source unit that includes a light source (light emitting element) and a slit forming mechanism as in a standard slit lamp microscope; a light source unit that includes a light source and a one dimensional optical scanner; and a light source unit that includes a line light source that emits a light beam having a linear cross sectional shape (a one dimensional cross sectional shape) in a macroscopic sense.

The polarizer in the illumination system of the embodiment is referred to as an illumination polarizer, and the polarization component extracted from the slit illumination light by the illumination polarizer is referred to as an illumination polarization component. The illumination polarizer may be any types or kinds of polarizing element, for example, a polarizer of a transmission type or a polarizer of a reflection type.

The photography system of the embodiment includes a polarizer and an image sensor. This polarizer is configured to extract a predetermined polarization component from return light that returns from the subject's eye onto which the slit illumination light is projected. The image sensor is configured to detect the photography polarization component extracted by this polarizer.

Light that enters the photography system (the return light from the subject's eye with the slit illumination light projected) may include not only return light of the slit illumination light but also light of any other kinds such as ambient light.

The polarizer in the photography system of the embodiment is referred to as a photography polarizer, and the polarization component extracted from the return light by the photography polarizer is referred to as a photography polarization component. The photography polarizer may be any types or kinds of polarizing element, for example, a polarizer of a transmission type or a polarizer of a reflection type.

The image sensor in the photography system of the embodiment may be of any types or kinds, and the image sensor of some aspect examples may be any types or kinds of area sensor such as a CCD area sensor or a CMOS area sensor.

The optical system (the illumination system and the photography system) that satisfies the Scheimpflug condition may, for example, be a combinatory configuration of the illumination polarizer, the photography polarizer, and the optical system disclosed in Patent Document 3 (Japanese Unexamined Patent Application Publication No. 2019-213733 (International Publication No. WO 2019/240149)), but is not limited to this. Employing the optical system configured to satisfy the Scheimpflug condition allows the ophthalmic apparatus according to the embodiment to perform photography in such a manner that a wide area of the subject's eye is in focus. For example, in the case of anterior segment imaging, the ophthalmic apparatus is capable of performing photography with at least an area defined by the anterior surface of the cornea of the subject's eye and the posterior surface of the crystalline lens in focus. This makes it possible to provide representation, with high definition, of the entirety of the main observation target in the anterior segment.

Since the ophthalmic apparatus according to the embodiment includes the illumination polarizer and the photography polarizer, the ophthalmic apparatus according to the embodiment can provide an improvement in ophthalmic imaging by utilizing various operations and various processes related to polarization. For example, as will be described in detail later, one aspect of the embodiment is capable of removing specular reflection noise in an ocular image, another aspect is capable of solving the problem of deterioration in image visibility caused from reflectance differences between ocular tissues, and yet another aspect is capable of obtaining a polarization characteristic of the subject's eye.

Furthermore, in addition to being equipped with the illumination polarizer and the photography polarizer, the ophthalmic apparatus according to the embodiment is also equipped with the illumination system and the photography system that are configured to satisfy the Scheimpflug condition. As a result, the ophthalmic apparatus according to the embodiment can exhibit a novel and remarkable advantageous effect in which all of the following benefits are achieved: wideness (broadness) of an imaging area; high definition (high ability of visualization) over the entire imaging area; and improvement in ophthalmic imaging utilizing polarization.

For example, the ophthalmic apparatus according to the embodiment is capable of: generating an ocular image, of a wide area and with high definition, with specular reflection noise eliminated; generating an ocular image, of a wide area and with high definition, in which deterioration in image visibility caused from reflectance differences between ocular tissues is amended; and obtaining a polarization characteristic over a wide area of the subject's eye with high quality (any selected kinds of quality of information, such as accuracy, precision, reproducibility, etc.).

An ophthalmic apparatus according to some aspect examples may be configured to scan a three dimensional region of a subject's eye. The ophthalmic apparatus according to such aspects is capable of both imaging a wide three dimensional region of the subject's eye with high visualization ability, and providing an improvement in ophthalmic imaging that uses polarization.

For example, the ophthalmic apparatus according to such aspects is capable of generating with high definition a wide area three dimensional ocular image in which specular reflection noise is removed, generating with high definition a wide area three dimensional ocular image in which deterioration in image visibility caused from reflectance differences between ocular tissues is amended, and obtaining with high quality a distribution of a polarization characteristic in a wide three dimensional region of the subject's eye.

Several aspect examples of the embodiments outlined above will be described below. The present disclosure mainly describes several aspect examples of an ophthalmic apparatus, several aspect examples of a method of controlling an ophthalmic apparatus, several aspect examples of a computer program, and several aspect examples of a recording medium. However, aspects of the embodiments are not limited to these categories. For example, those skilled in the art will understand that the present disclosure may provide various aspects of a method of a medical process (medical practice, medical activity, or the like), various aspects of a method of imaging, various aspects of a method of data processing, and so forth.

It should be noted that, in another embodiment, the illumination system may include a light source (e.g., a semiconductor laser) configured to emit light having a linear polarization property, in place of the above-described combination of the light source unit configured to output slit illumination light and the illumination polarizer configured to extract the illumination polarization component from the slit illumination light output by the light source unit.

The illumination system of this another embodiment may not include a polarizer. In addition, the illumination system of this another embodiment may include any one or both of the following components: a mechanism for changing the polarization direction of illumination light by rotating a light source that emits light having a linear polarization property; and a means (e.g., optical element, mechanism, or the like) for changing the polarization direction of light having a linear polarization property output from a light source.

Accordingly, the present disclosure also includes an ophthalmic apparatus with the following elements: the ophthalmic apparatus includes an illumination system configured to project illumination light onto the subject's eye; the ophthalmic apparatus includes a photography system configured to perform photography of the subject's eye; the illumination system and the photography system are configured to satisfy the Scheimpflug condition; the illumination system includes a light source unit configured to output slit illumination light of linear polarization; the illumination system is configured to project the slit illumination light of linear polarization onto the subject's eye as the illumination light; the photography system includes a photography polarizer configured to extract a photography polarization component from return light from the subject's eye onto which the slit illumination light of linear polarization is projected; and the photography system includes an image sensor configured to detect the photography polarization component extracted by the photography polarizer.

Any of the matters and/or items in any of the various aspect examples described in the present disclosure may be combined with the ophthalmic apparatus according to this another embodiment having the configuration described above. In addition, the present disclosure also includes embodiments in other categories corresponding to the ophthalmic apparatus according to this another embodiment. Examples of the embodiments in other categories include an embodiment relating to a method of controlling an ophthalmic apparatus, an embodiment relating to a computer program, an embodiment relating to a recording medium, an embodiment relating to a method of a medical process (medical practice, medical activity, or the like), an embodiment relating to a method of imaging, and an embodiment relating to a method of data processing.

More generally, the present disclosure includes an ophthalmic apparatus with the following elements: the ophthalmic apparatus includes an illumination system configured to project illumination light onto the subject's eye; the ophthalmic apparatus includes a photography system configured to perform photography of the subject's eye; the illumination system and the photography system are configured to satisfy the Scheimpflug condition; the illumination system is configured to project slit illumination light of linear polarization onto the subject's eye as the illumination light; the photography system includes a photography polarizer configured to extract a photography polarization component from return light from the subject's eye to which the slit illumination light of linear polarization is projected; and the photography system includes an image sensor configured to detect the photography polarization component extracted by the photography polarizer.

Any of the matters and/or items in any of the various aspect examples described in the present disclosure may be combined with the ophthalmic apparatus according to such more general embodiments including the configuration described above. In addition, the present disclosure also includes embodiments in other categories corresponding to the ophthalmic apparatus according to the more general embodiments. Examples of the embodiments in other categories include an embodiment relating to a method of controlling an ophthalmic apparatus, an embodiment relating to a computer program, an embodiment relating to a recording medium, an embodiment relating to a method of a medical process (medical practice, medical activity, or the like), an embodiment relating to a method of imaging, and an embodiment relating to a method of data processing.

<Ophthalmic Apparatus>

Several aspect examples of the ophthalmic apparatus according to an embodiment will be provided.

Figure 2:
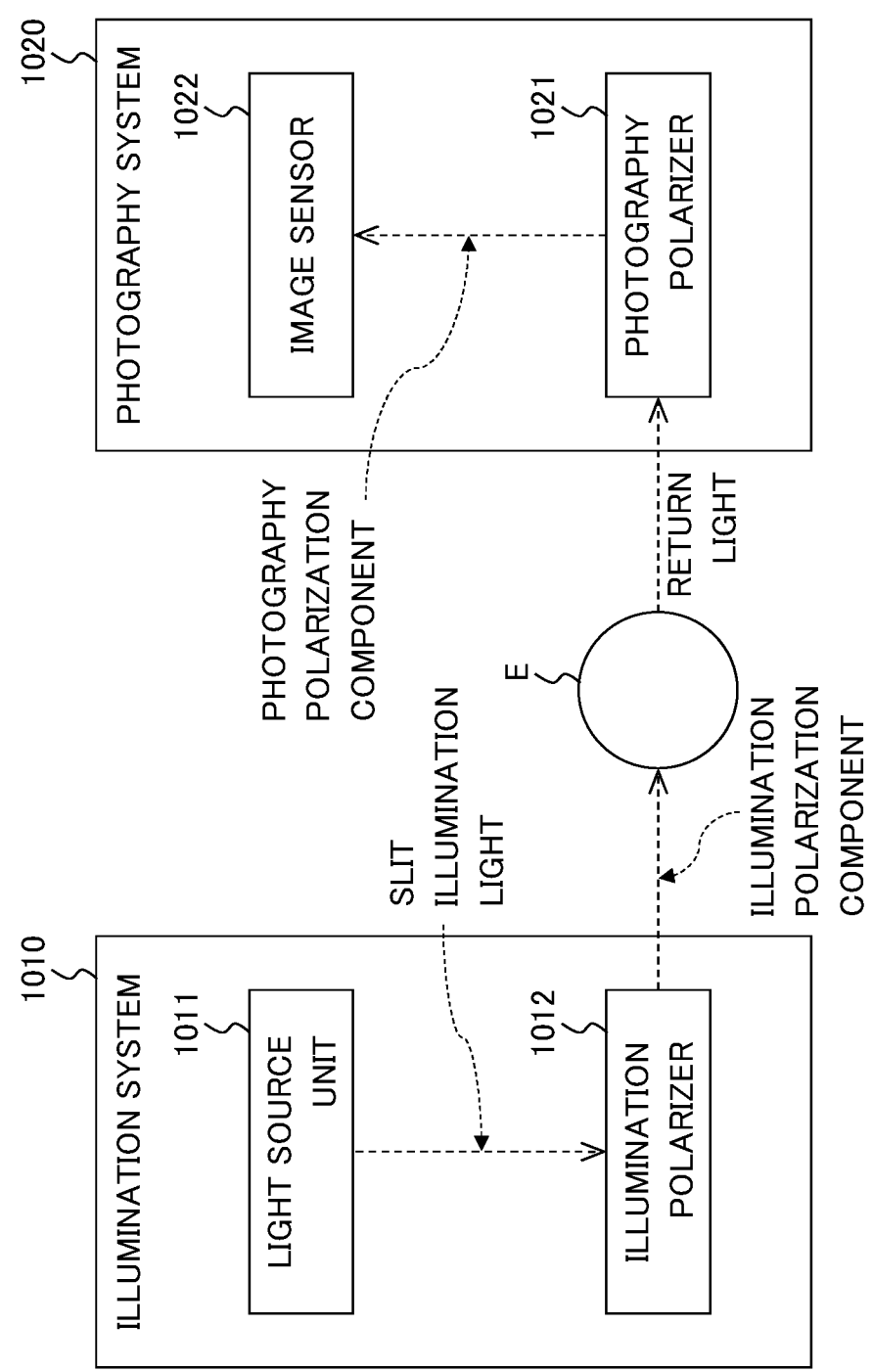
FIG. 2 is a diagram illustrating a configuration and an operation of an ophthalmic apparatus according to an aspect example of an embodiment.

FIG. 1 and FIG. 2 show a configuration of an ophthalmic apparatus according to one aspect of the embodiment. The ophthalmic apparatus 1000 according to the present aspect includes the illumination system 1010, the photography system 1020, and the controller 1030.

The illumination system 1010 is configured to project illumination light onto the subject's eye E. The illumination system 1010 includes the light source unit 1011 and the illumination polarizer 1012. The light source unit 1011 is configured to output slit illumination light, and the illumination polarizer 1012 is configured to extract an illumination polarization component from the slit illumination light output by the light source unit 1011. Although not shown in the drawings, the illumination system 1010 further includes other elements such as an objective lens.

The photography system 1020 is configured to perform photography of the subject's eye E to generate a digital image. The photography system 1020 includes the photography polarizer 1021 and the image sensor 1022. The photography polarizer 1021 is configured to extract a photography polarization component from return light from the subject's eye E with the slit illumination light projected by the illumination system 1010. The image sensor 1022 is configured to detect the photography polarization component extracted by the photography polarizer 1021. Although not shown in the drawings, the photography system 1020 further includes other elements such as an objective lens.

The illumination system 1010 and the photography system 1020 are configured to satisfy the Scheimpflug condition. More specifically, the illumination system 1010 and the photography system 1020 are configured in such a manner that a plane passing through the optical axis of the optical system of the illumination system 1010 (the illumination optical system) (the plane that contains the subject plane), the principal plane of the optical system of the photography system 1020 (the photography optical system), and the light detecting plane of the image sensor 1022 all intersect on the same straight line.

the illumination system 1010 and the photography system 1020 are included in a photography unit for performing photography of the subject's eye E. The photography unit functions as a Scheimpflug camera, and can perform photography of the subject's eye E in a state in which the photography system 1020 is in focus at all positions in the subject plane, that is, at all positions in the direction along the optical axis of the illumination system 1010. An image generated by the photography unit is sometimes referred to as a Scheimpflug image. Several non-limiting specific examples of an optical system (the illumination optical system and the photography optical system) configured to satisfy the Scheimpflug condition, will be described later.

The controller 1030 is configured to execute control of the illumination system 1010 and control of the photography system 1020. The illumination system 1010 and the photography system 1020 generate a Scheimpflug image by conducting photography of the subject's eye E under the control executed by the controller 1030.

The controller 1030 includes hardware elements such as a processor and a storage device. The storage device stores computer programs such as a control program. One or more of the functions of the controller 1030 are implemented by cooperation of software such as the control program and hardware such as the processor.

The ophthalmic apparatus of some aspect examples may not include the controller 1030. If this is the case, the control of the illumination system 1010 and the control of the photography system 1020 are executed, for example, by a computer (processor) exterior to the ophthalmic apparatus.

As shown in FIG. 2, the ophthalmic apparatus 1000 of the present aspect outputs slit illumination light by the light source unit 1011, extracts an illumination polarization component from the slit illumination light by the illumination polarizer 1012, and projects the illumination polarization component onto the subject's eye E as illumination light by the illumination system 1010. Part of return light of the illumination light projected onto the subject's eye E enters the photography system 1020. The ophthalmic apparatus 1000 of the present aspect extracts, by the photography polarizer 1021, a photography polarization component from the return light incident on the photography system 1020, and detects the photography polarization component by the image sensor 1022.

The data output from the image sensor 1022 that has detected the photography polarization component is image data. This image data is a Scheimpflug image of the subject's eye E. This Scheimpflug image contains information representing the polarization state of the return light of the illumination light projected onto the subject's eye E. The return light of the illumination light projected onto the subject's eye E is affected by the polarization property of the subject's eye E, and the Scheimpflug image therefore contains information representing the polarization characteristics of the subject's eye E.

According to the ophthalmic apparatus 1000 of the present aspect configured in this way, it becomes possible to generate a high-quality image in which the polarization characteristics of the subject's eye E over a wide area are reflected, and therefore to provide an improvement in ophthalmic imaging.

Figure 3:
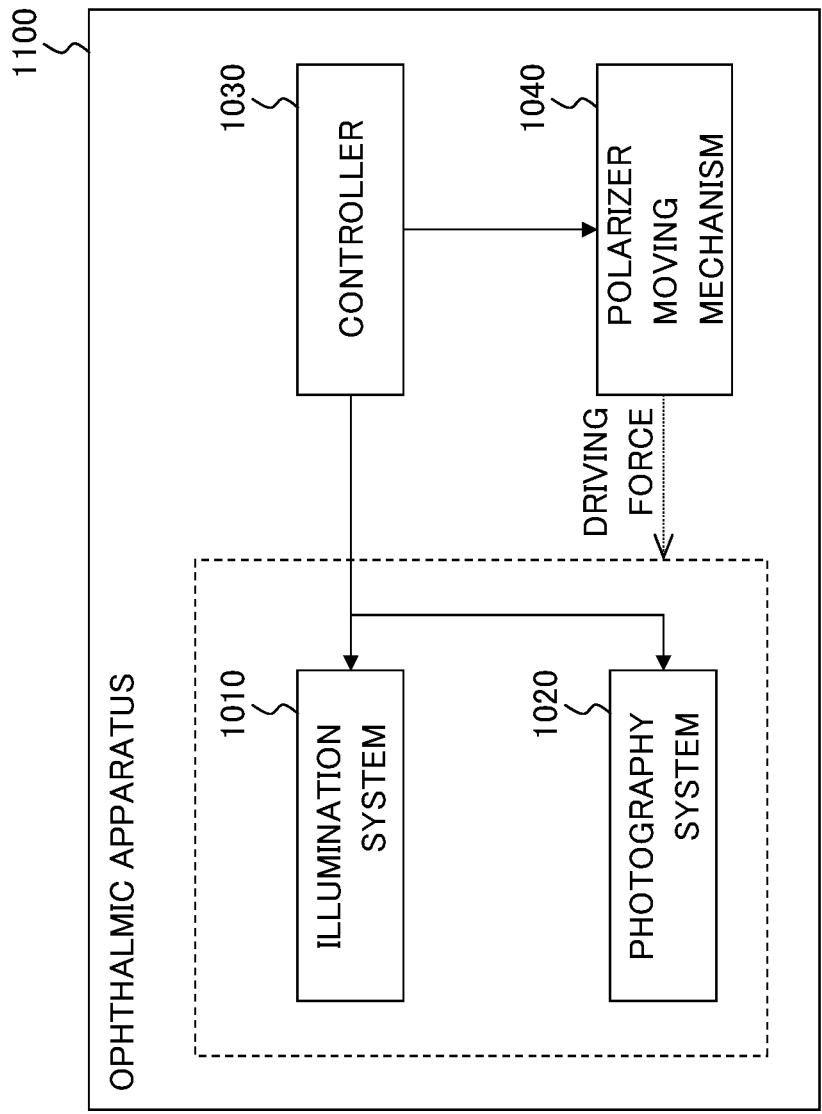
FIG. 3 is a diagram illustrating a configuration of an ophthalmic apparatus according to an aspect example of an embodiment.
Figure 4A:
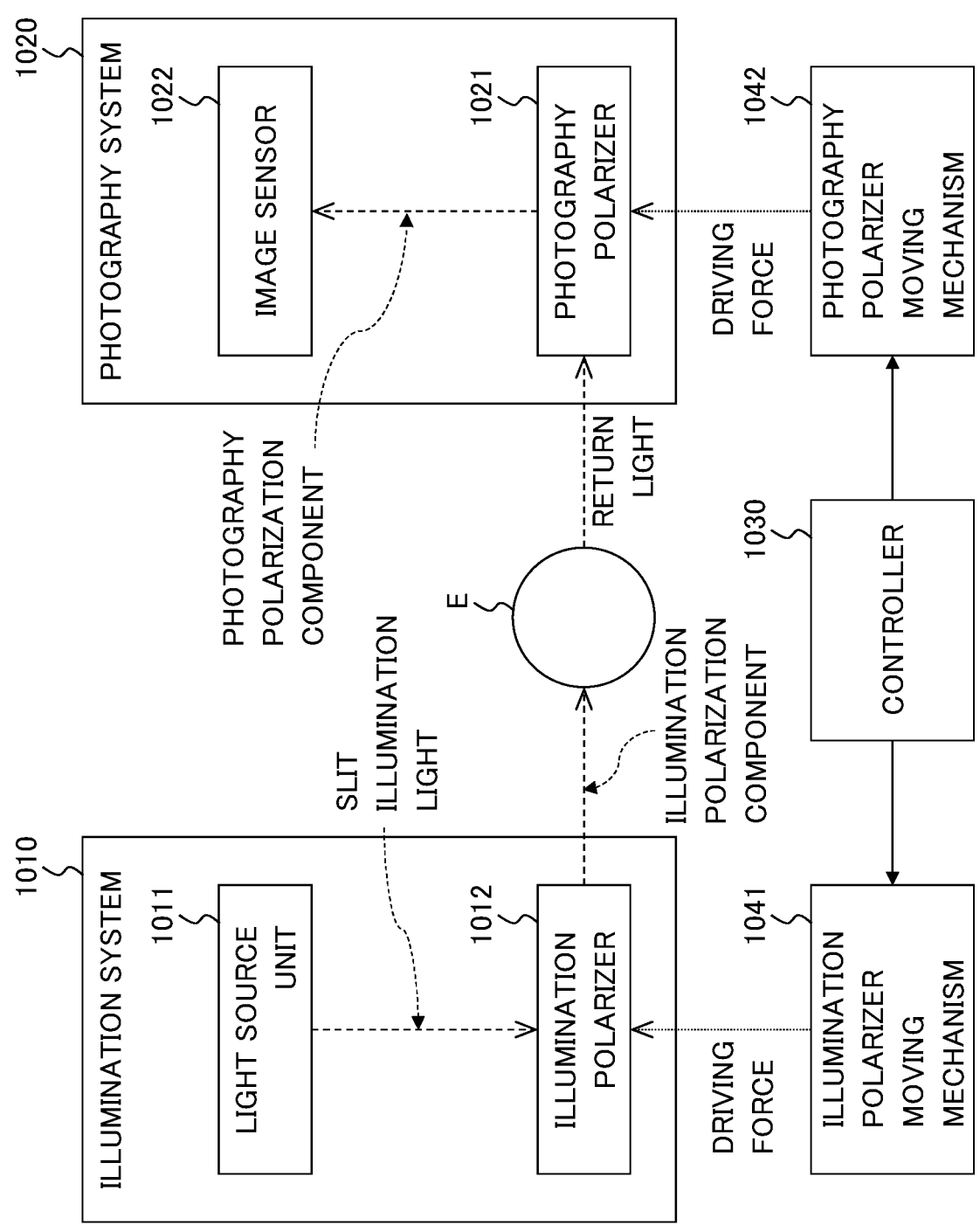
FIG. 4A is a diagram illustrating a configuration and an operation of an ophthalmic apparatus according to an aspect example of an embodiment.
Figure 4B:
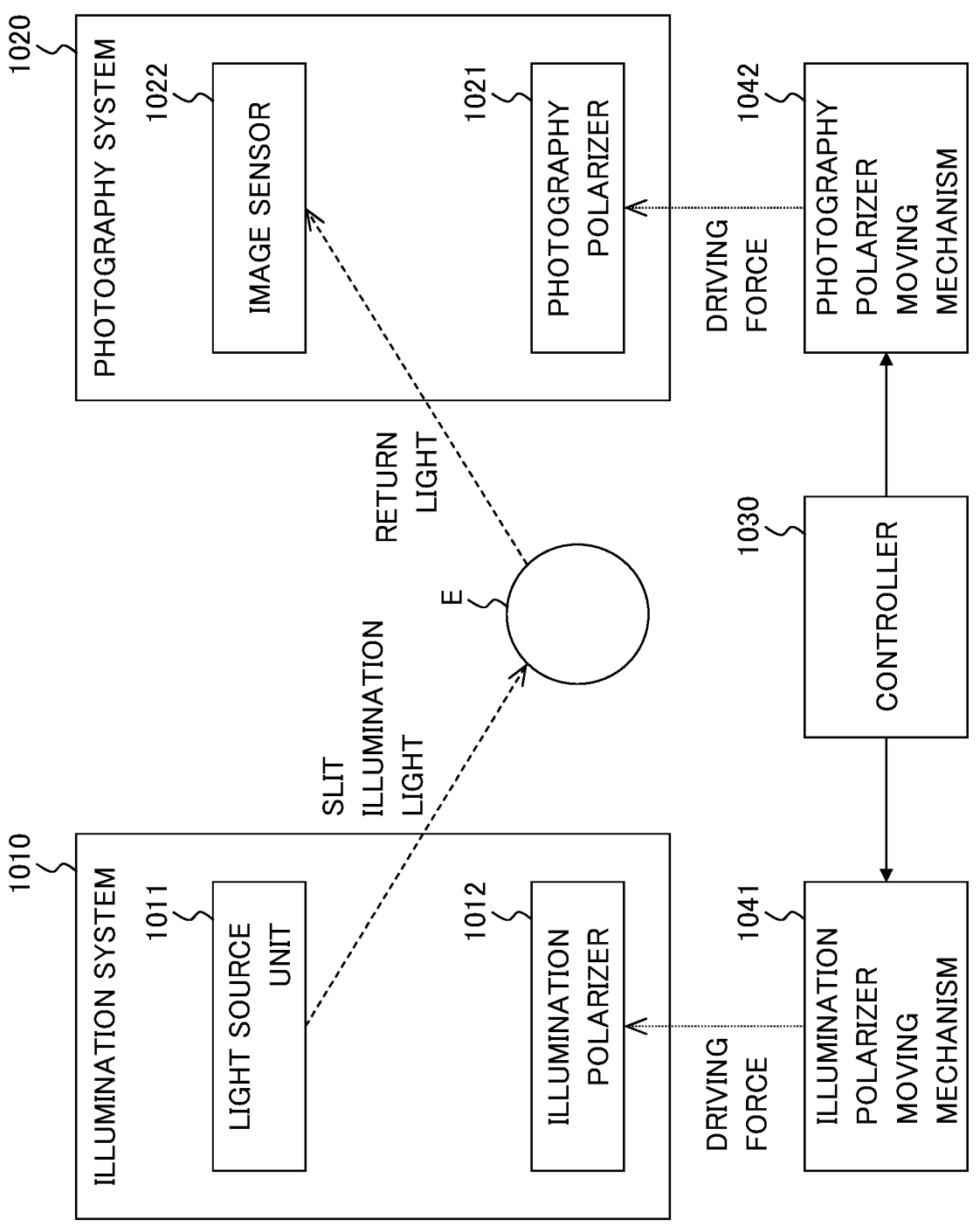
FIG. 4B is a diagram illustrating a configuration and an operation of an ophthalmic apparatus according to an aspect example of an embodiment.

FIG. 3, FIG. 4A and FIG. 4B show a configuration of an ophthalmic apparatus according to one aspect of the embodiment. The ophthalmic apparatus 1100 according to the present aspect includes the polarizer moving mechanism 1040, in addition to the illumination system 1010, the photography system 1020, and the controller 1030 which have the same or similar configurations as or to the corresponding components of the ophthalmic apparatus 1000.

The polarizer moving mechanism 1040 is configured to move a polarizer with respect to an optical path. The polarizer moving mechanism 1040 includes an actuator configured to generate driving force and a mechanism configured to transmit the generated driving force to the polarizer. The polarizer moving mechanism 1040 operates under control executed by the controller 1030.

As shown in FIG. 4A and FIG. 4B, the polarizer moving mechanism 1040 of the present aspect includes the illumination polarizer moving mechanism 1041 and the photography polarizer moving mechanism 1042. The illumination polarizer moving mechanism 1041 is configured to insert and remove the illumination polarizer 1012 into and from an optical path of the illumination system 1010. The optical path of the illumination system 1010 is referred to as an illumination optical path. In other words, the illumination polarizer moving mechanism 1041 is configured to perform an operation of inserting the illumination polarizer 1012 into the illumination optical path and an operation of removing the illumination polarizer 1012 from the illumination optical path. Likewise, the photography polarizer moving mechanism 1042 is configured to insert and remove the photography polarizer 1021 into and from an optical path of the photography system 1020. The optical path of the photography system 1020 is referred to as a photography optical path.

The controller 1030 is configured to perform control of the illumination polarizer moving mechanism 1041 and control of the photography polarizer moving mechanism 1042. As shown in FIG. 4A and FIG. 4B, the controller 1030 may perform the control of the illumination polarizer moving mechanism 1041 and the control of the photography polarizer moving mechanism 1042 in an interlocking manner.

In the present example, the controller 1030 is configured to perform the control of the illumination polarizer moving mechanism 1041 for inserting the illumination polarizer 1012 into the illumination optical path and the control of the photography polarizer moving mechanism 1042 for inserting the photography polarizer 1021 into the photography optical path in an interlocking manner, and further the control of the illumination polarizer moving mechanism 1041 for removing the illumination polarizer 1012 from the illumination optical path and the control of the photography polarizer moving mechanism 1042 for removing the photography polarizer 1021 from the photography optical path in an interlocking manner.

The present example allows to selectively conduct an imaging (photography) operation with consideration of polarization and an ordinary imaging (photography) operation without consideration of polarization.

In the case where only the illumination polarizer moving mechanism 1041 is provided, or in the case where both the illumination polarizer moving mechanism 1041 and the photography polarizer moving mechanism 1042 are provided and the illumination polarizer moving mechanism 1041 can be selectively controlled, the controller 1030 may place the illumination polarizer 1012 in the illumination optical path without the use of the photography polarizer 1021 for the photography optical path.

According to the present example, the ophthalmic apparatus 1100 can perform photography of the subject's eye E using the illumination polarization component of the slit illumination light as illumination light.

Conversely, in the case where only the photography polarizer moving mechanism 1042 is provided, or in the case where both the illumination polarizer moving mechanism 1041 and the photography polarizer moving mechanism 1042 are provided and the photography polarizer moving mechanism 1042 can be selectively controlled, the controller 1030 may place the photography polarizer 1021 in the photography optical path without the use of the illumination polarizer 1012 for the illumination optical path.

According to the present example, the ophthalmic apparatus 1100 can detect the photography polarization component of the return light from the subject's eye E in a selective manner.

Figure 5:
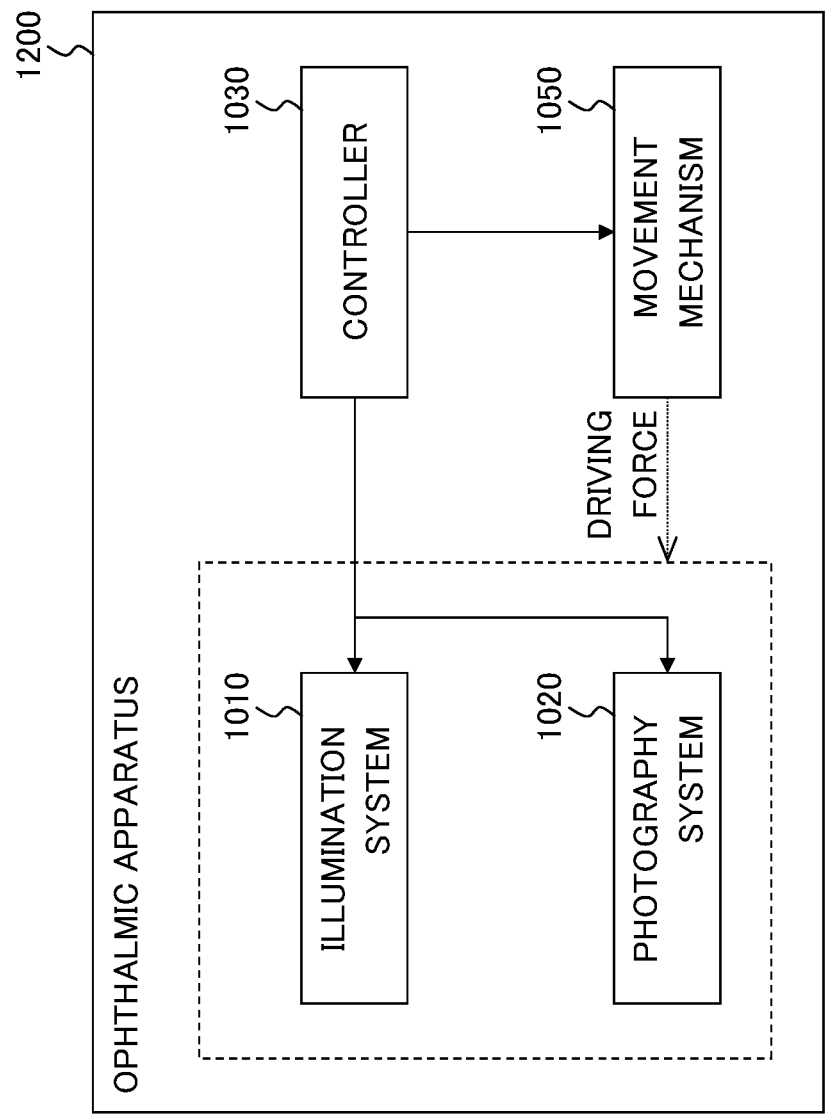
FIG. 5 is a diagram illustrating a configuration of an ophthalmic apparatus according to an aspect example of an embodiment.

FIG. 5 shows a configuration of an ophthalmic apparatus according to one aspect of the embodiment. The ophthalmic apparatus 1200 according to the present aspect includes the movement mechanism 1050, in addition to the illumination system 1010, the photography system 1020, and the controller 1030 which have the same or similar configurations as or to the corresponding components of the ophthalmic apparatus 1000.

The movement mechanism 1050 is configured to move the illumination system 1010 and the photography system 1020. The movement mechanism 1050 includes an actuator configured to generate driving force and a mechanism configured to transmit the generated driving force to the illumination system 1010 and the photography system 1020. The movement mechanism 1050 operates under control executed by the controller 1030.

The movement mechanism 1050 may include a mechanism that has any kinds of alternative functions equivalent to the function of moving the illumination system 1010 and the photography system 1020. Examples of such an alternative mechanism include a mechanism configured to move an illumination position (a projection position of illumination light onto the subject's eye E) by deflecting illumination light such as an illumination scanner or a movable illumination mirror, and a mechanism configured to move an imaging position by deflecting return light from the subject's eye E such as an imaging scanner or a movable imaging mirror.

According to the present aspect, the ophthalmic apparatus 1200 can perform scanning of the subject's eye E using the illumination system 1010 and the photography system 1020 configured to satisfy the Scheimpflug condition. In other words, the ophthalmic apparatus 1200 can conduct image acquisition (image collection) while moving the illumination system 1010 and the photography system 1020 that satisfy the Scheimpflug condition. With this, the ophthalmic apparatus 1200 can acquire a plurality of images (Scheimpflug image group) from a three dimensional region of the subject's eye E. In addition, the ophthalmic apparatus 1200 may construct a three dimensional image from the Scheimpflug image group acquired, and further create a rendered image of the three dimensional image constructed.

Figure 6A:
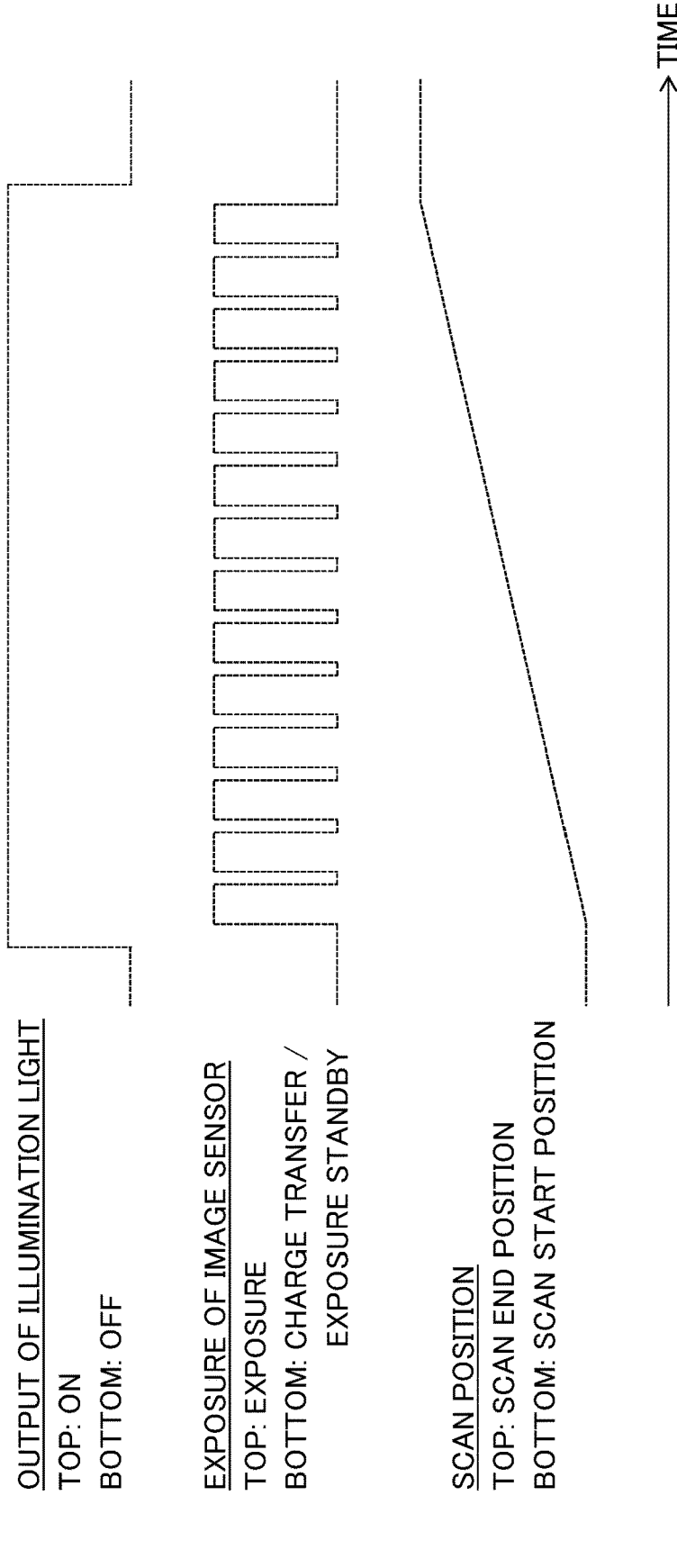
FIG. 6A is a timing chart illustrating processing executed by an ophthalmic apparatus according to an aspect example of an embodiment.
Figure 6B:
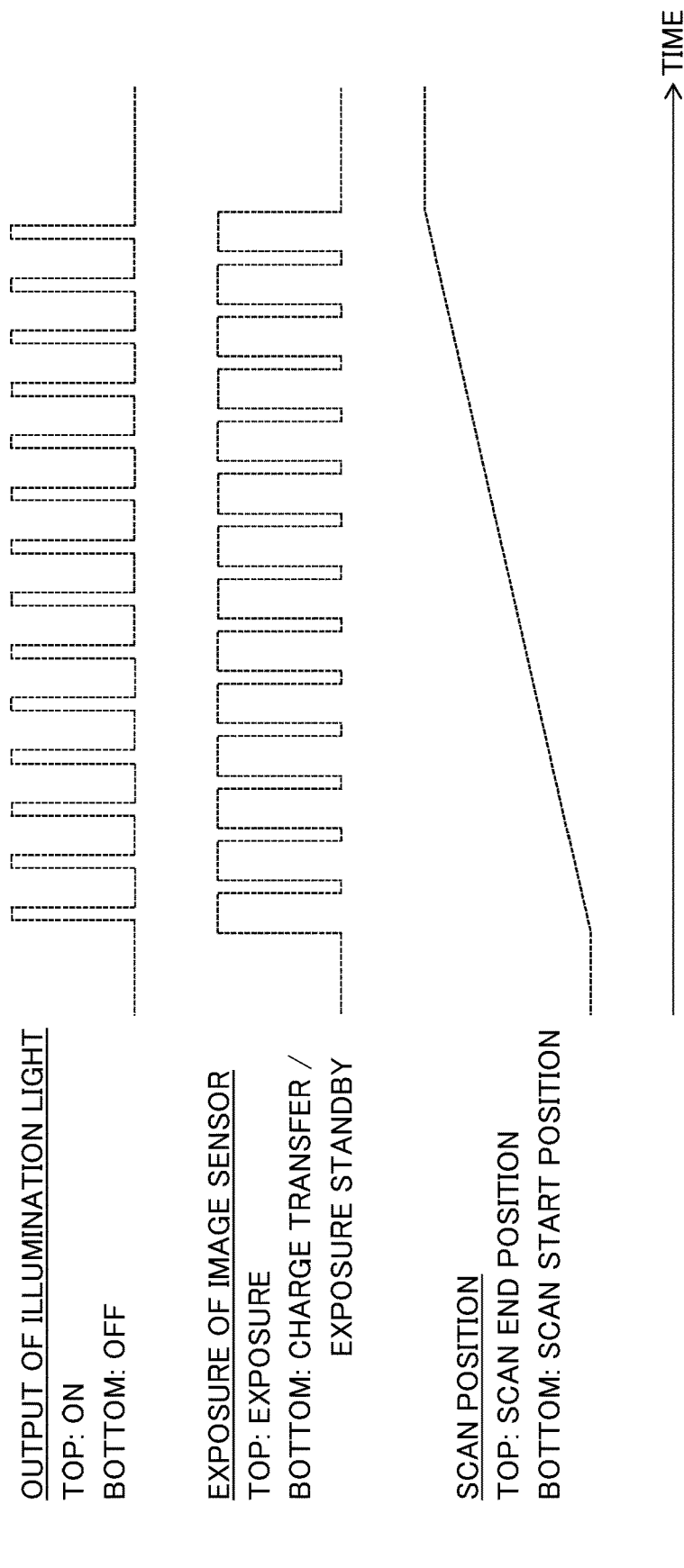
FIG. 6B is a timing chart illustrating processing executed by an ophthalmic apparatus according to an aspect example of an embodiment.

FIG. 6A and FIG. 6B show two examples of the scanning operation conducted by the present aspect.

The scanning operation shown in FIG. 6A is implemented by interlocking control (synchronous control) between the followings: the output of the illumination light by the illumination system 1010 (the projection of the illumination light onto the subject's eye E); the exposure of the image sensor 1022 of the photography system 1020 (the photographing by the photography system 1020); and the position of the illumination system 1010 and the photography system 1020 moved by the movement mechanism 1050 (scan position).

More specifically, the scanning of the present example is implemented by combining continuous output of the illumination light, repetitive photographing (repetitive exposure) by the image sensor 1022, and continuous movement of the illumination system 1010 and the photography system 1020 from the scan start position to the scan end position. The repetitive exposure of the image sensor 1022 is implemented by alternatingly performing exposure and electric charge transfer (and exposure standby).

The scanning operation shown in FIG. 6A has an advantage of being simple and easy to control, but also has a disadvantage that a blurred image may be obtained due to the movement of the scan position and/or the eye movement of the subject's eye E during exposure. In order to address this drawback, shortening the exposure time (exposure period, exposure duration) of the image sensor 1022 may be considered as a solution. However, in the case where the exposure time is shortened, the illumination light is then continuously projected onto the subject's eye E even during the non-exposure period, which may impose a burden on the subject. The scanning operation shown in FIG. 6B can be achieved by taking these issues into consideration.

In the scanning operation shown in FIG. 6B, control is executed in such a manner that the projection time (projection period, projection duration) of the illumination light onto the subject's eye E is shorter than the exposure time (exposure period, exposure duration) of the image sensor 1022. This control is implemented by combining control of the illumination system 1010, control of the photography system 1020, and control of the movement mechanism 1050.

The control of the illumination system 1010 may be a freely selected method of control such as electrical control, mechanical control, or a combination of electrical control and mechanical control. Here, the electrical control may be control of a light source (i.e., turning the power on and off of the light source) or control of an electronic shutter, and the mechanical control may be control of a mechanical shutter or control of a rotary shutter. The light source is provided in the light source unit 1011. The shutters are also provided in the light source unit 1011 and configured to switch between passing and blocking light output from the light source. In other words, the shutters are configured to switch between a state in which the illumination light is projected onto the subject's eye E and a state in which not projected. The shutters may be placed at a position on the downstream side than the illumination polarizer 1012.

The control of the illumination system 1010 is not limited to control for switching between the state in which the illumination light is projected onto the subject's eye E and the state in which not projected, that is, between the projection state and the non-projection state. The control of the illumination system 1010 may be control for modulating the intensity (light amount) of illumination light projected onto the subject's eye E.

The control of the photography system 1020 may be a freely selected method of control such as electrical control, mechanical control, or a combination of electrical control and mechanical control. Here, the electrical control may be control of the image sensor 1022 or control of an electronic shutter, and the mechanical control may be control of a mechanical shutter or control of a rotary shutter.

In the scanning operation shown in FIG. 6B, control is executed in such a manner not only that the length (projection time, projection duration) of the period (projection period) during which the illumination light is projected onto the subject's eye E becomes shorter than the length (exposure time, exposure duration) of the period (exposure period) during which the image sensor 1022 can receive light, but also that at least a part of the projection period and at least a part of the exposure period coincide with one another through synchronization control between the sequence of the output of the illumination light (a plurality of times of outputs arranged in time series) and the sequence of the exposure of the image sensor 1022 (a plurality of times of exposures arranged in time series).

In the scanning operation shown in FIG. 6B, for each exposure period in the exposure sequence, a partial period of this exposure period matches one projection period of the illumination light. In other words, for each exposure period in the exposure sequence, the length of the corresponding illumination light projection period (projection time, projection duration) is shorter than the length of this exposure period (exposure time, exposure duration), and a partial period of this exposure period and the entirety of the corresponding projection period coincide with one another.

According to the scanning operation shown in FIG. 6B, in each exposure period of the exposure sequence, exposure (light reception and electric charge accumulation by the image sensor 1022) is substantially performed only during a projection period shorter than this exposure period. Therefore, image blurring caused by movement of the scan position and/or eye movement during exposure can be reduced compared to the scanning operation shown in FIG. 6A.

In the scanning operation shown in FIG. 6B, the scan position is continuously moved. Although it is possible to move the scan position in a stepwise (intermittent, discontinuous) manner, this would increase the complexity of control as well as cause vibration from repetition of sudden starts and stops of the illumination system 1010 and the photography system 1020 which may adversely affect the quality of photography. Taking these risks into account, it is considered better to continuously move the scan position as in the scanning operation shown in FIG. 6B. However, the embodiment according to the present disclosure does not exclude an aspect of stepwise movement of the scan position.

Figure 7A:
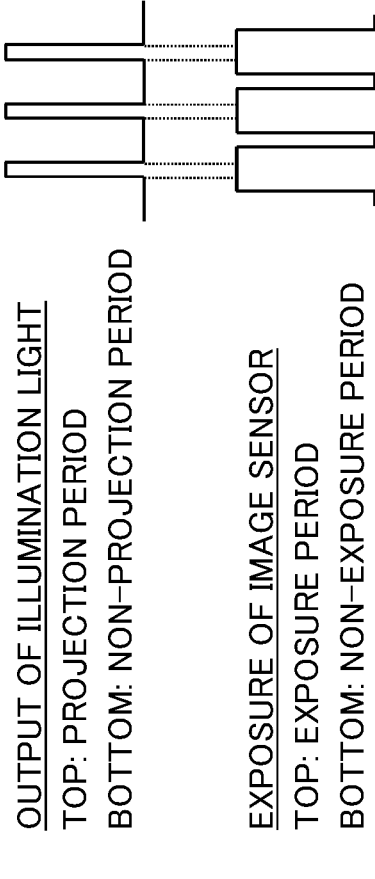
FIG. 7A is a timing chart illustrating processing executed by an ophthalmic apparatus according to an aspect example of an embodiment.

In the scanning operation shown in FIG. 6B, as shown in FIG. 7A, the entirety of each projection period of the illumination light coincides with a partial period of a corresponding exposure period of the image sensor 1022. In other words, the entirety of each projection period of the illumination light temporally coincides with (temporally in parallel with) a partial period of a corresponding exposure period of the image sensor 1022. However, the condition (scanning condition) for obtaining the above advantageous effects of the scanning operation shown in FIG. 6B, is that the projection time or duration of the illumination light onto the subject's eye E is shorter than the exposure time or duration of the image sensor 1022 and that at least a part of the projection period of the illumination light onto the subject's eye E and at least a part of the exposure period of the image sensor 1022 coincide with each other.

A method of scanning that satisfies this scanning condition is not limited to the scanning operation shown in FIG. 6B. The scanning operation shown in FIG. 7B provides another example of the method of scanning that satisfies this scanning condition. In the scanning operation shown in FIG. 7B, a partial period of each projection period of the illumination light corresponds to a partial period of one exposure period of the image sensor 1022.

Figure 8:
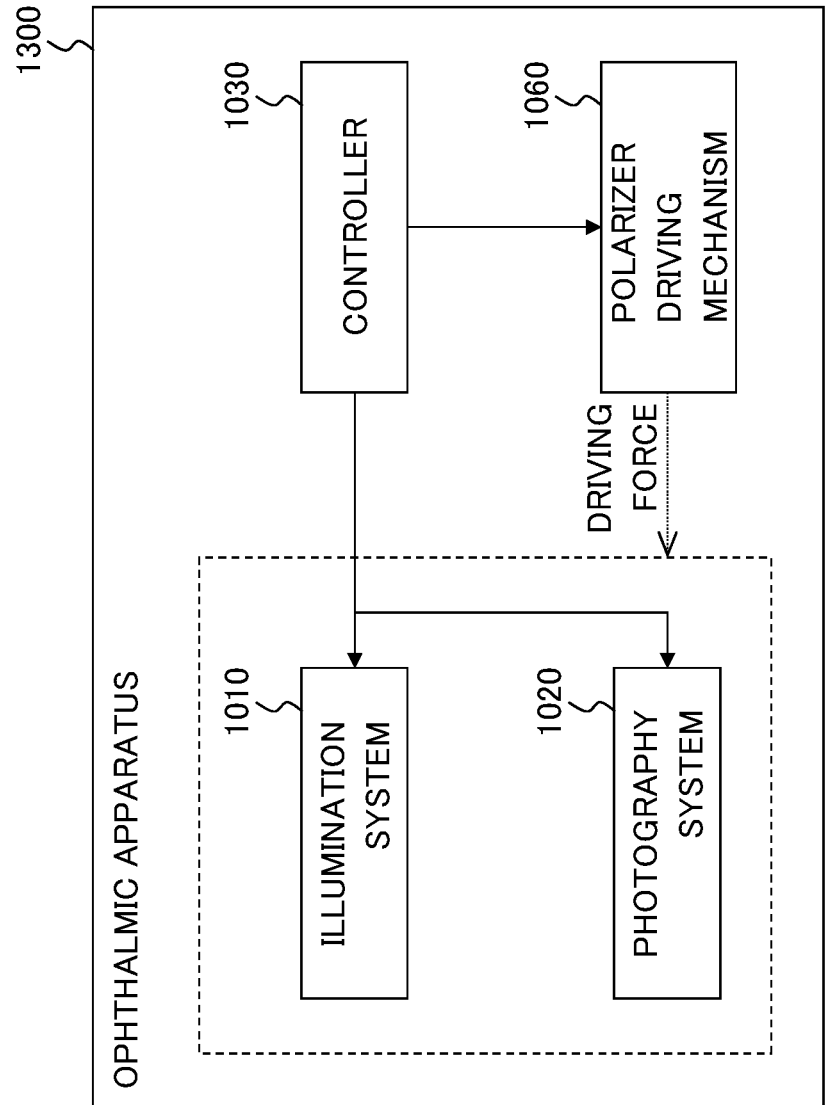
FIG. 8 is a diagram illustrating a configuration of an ophthalmic apparatus according to an aspect example of an embodiment.
Figure 9A:
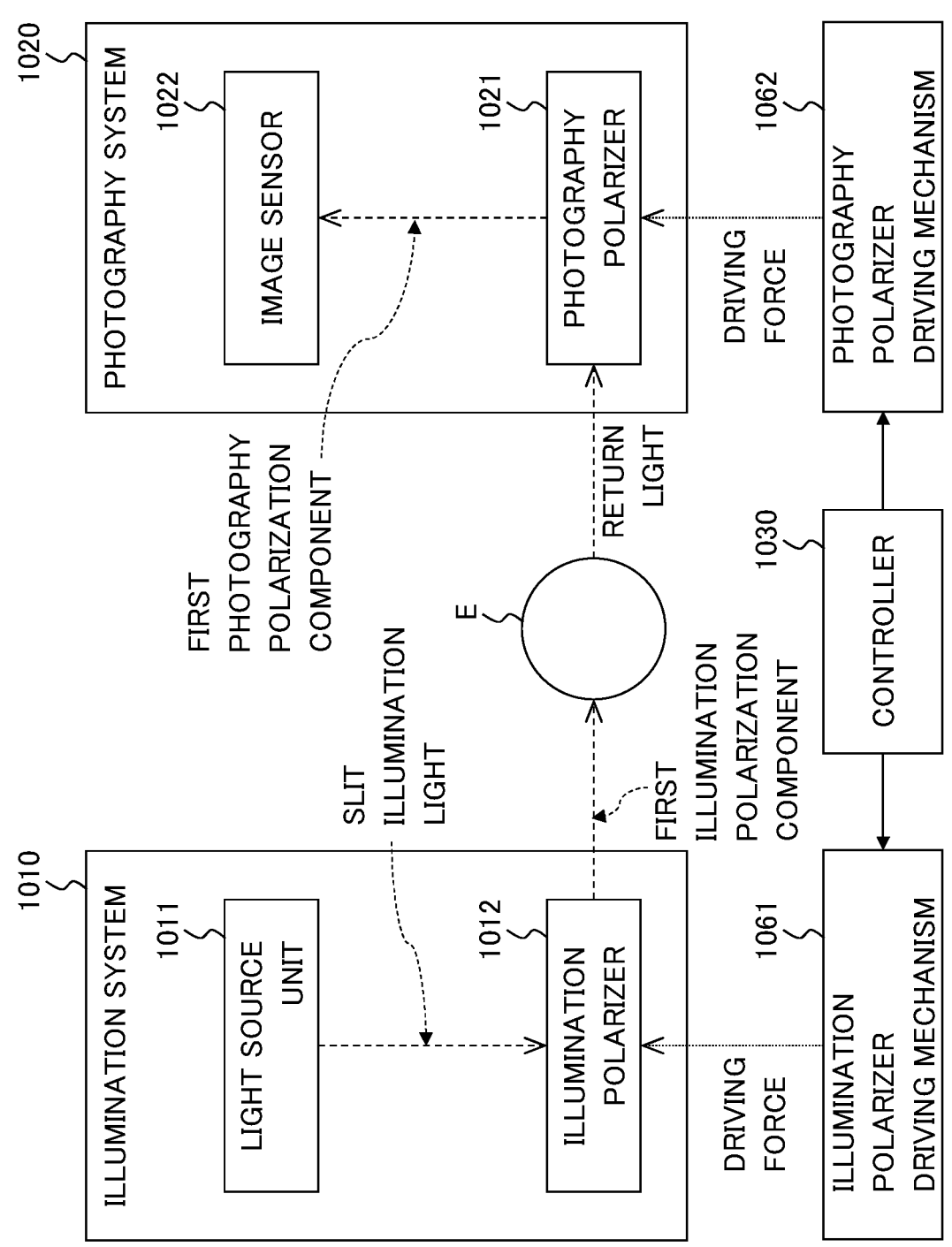
FIG. 9A is a diagram illustrating a configuration and an operation of an ophthalmic apparatus according to an aspect example of an embodiment.
Figure 9B:
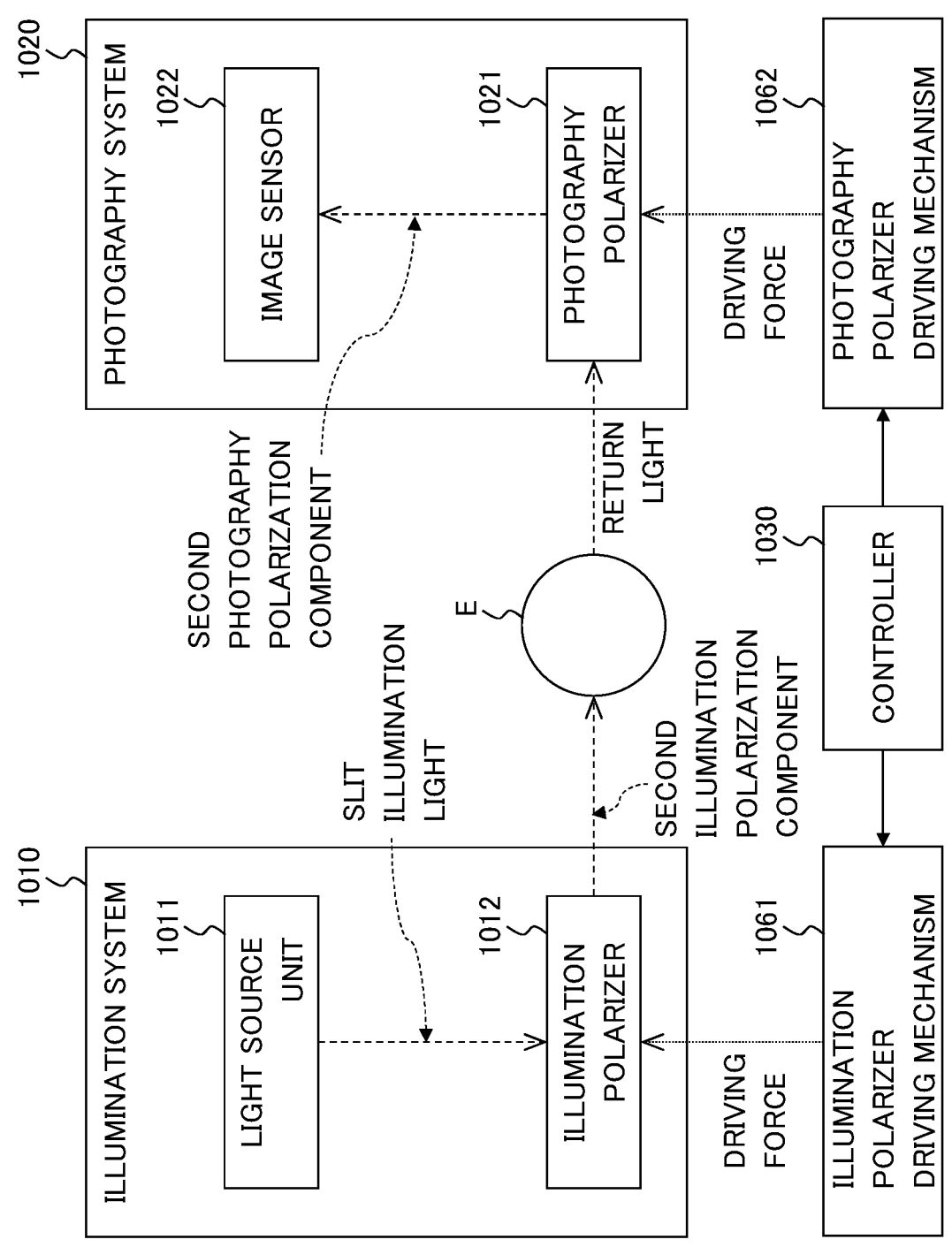
FIG. 9B is a diagram illustrating a configuration and an operation of an ophthalmic apparatus according to an aspect example of an embodiment.

FIG. 8, FIG. 9A, and FIG. 9B show a configuration of an ophthalmic apparatus according to one aspect of the embodiment. The ophthalmic apparatus 1300 according to the present aspect includes the polarizer driving mechanism 1060, in addition to the illumination system 1010, the photography system 1020, and the controller 1030 which have the same or similar configurations as or to the corresponding components of the ophthalmic apparatus 1000.

The polarizer driving mechanism 1060 is configured to change the orientation of the polarization component to be extracted by a polarizer, that is, to change the polarization direction. In other words, the polarizer driving mechanism 1060 is configured to perform driving of the illumination polarizer 1012 and/or driving of the photography polarizer 1021. Here, the driving of the illumination polarizer 1012 is for changing the polarization direction of the illumination polarization component to be extracted from slit illumination light, and the driving of the photography polarizer 1021 is for changing the polarization direction of the photography polarization component to be extracted from return light from the subject's eye E. The polarizer driving mechanism 1060 includes an actuator configured to generate driving force and a mechanism configured to transmit the generated driving force to the polarizer. The polarizer driving mechanism 1060 operates under control executed by the controller 1030.

In some aspect examples, the polarizer is a polarizing plate. The polarizing plate is an optical element that allows only light having polarization in a specific direction to pass through. In these aspect examples, the polarizer driving mechanism 1060 is configured to rotate the polarizing plate. Rotating the polarizing plate changes the polarization direction of light to pass through the polarizing plate.

FIG. 9A and FIG. 9B show an example of the polarizer driving mechanism 1060. The polarizer driving mechanism 1060 of the present example includes the illumination polarizer driving mechanism 1061 and the photography polarizer driving mechanism 1062. The illumination polarizer driving mechanism 1061 is configured to perform driving of the illumination polarizer 1012 for changing the polarization direction of the illumination polarization component to be extracted from slit illumination light. The photography polarizer driving mechanism 1062 is configured to perform the driving of the photography polarizer 1021 for changing the polarization direction of the photography polarization component to be extracted from return light from the subject's eye E.

The operation examples shown in FIG. 9A and FIG. 9B represent the following two operations (1) and (2) of the polarizer driving mechanism 1060.

(1) The illumination polarizer driving mechanism 1061 changes the polarization direction of the light to pass through the illumination polarizer 1012 to two mutually different polarization directions. With this, the illumination polarization component to be extracted from the slit illumination light is changed to the first illumination polarization component and the second illumination polarization component. Here, the first illumination polarization component corresponds to one of the two polarization directions and the second illumination polarization component corresponds to the other.

(2) The photography polarizer driving mechanism 1062 changes the polarization direction of the light to pass through the photography polarizer 1021 to two mutually different polarization directions. With this, the photography polarization component to be extracted from the return light from the subject's eye E is changed to the first photography polarization component and the second photography polarization component. Here, the first photography polarization component corresponds to one of the two polarization directions and the second photography polarization component corresponds to the other.

In the example shown in FIG. 9A and FIG. 9B, the polarizer driving mechanism 1060 includes both the illumination polarizer driving mechanism 1061 and the photography polarizer driving mechanism 1062. However, in another example, the polarizer driving mechanism 1060 may include either one of the illumination polarizer driving mechanism 1061 or the photography polarizer driving mechanism 1062.

To put it differently, any of the following cases may be possible: both the polarization direction of the illumination polarization component to be extracted from the slit illumination light and the polarization direction of the photography polarization component to be extracted from the return light from the subject's eye E are variable; the polarization direction of the illumination polarization component to be extracted from the slit illumination light is fixed and the polarization direction of the photography polarization component to be extracted from the return light from the subject's eye E is variable; and the polarization direction of the illumination polarization component to be extracted from the slit illumination light is variable and the polarization direction of the photography polarization component to be extracted from the return light from the subject's eye E is fixed.

In the example shown in FIG. 9A and FIG. 9B, the illumination polarizer driving mechanism 1061 changes the polarization direction of the light to pass through the illumination polarizer 1012 to two mutually different polarization directions. However, in another example, the illumination polarizer driving mechanism 1061 may be configured to change the polarization direction of the light to pass through the illumination polarizer 1012 to three or more mutually different polarization directions.

In this way, the number of polarization directions selectively set by the illumination polarizer driving mechanism 1061 may be freely determined. In addition, the manner of change in the polarization direction carried out by the illumination polarizer driving mechanism 1061 is not limited to such stepwise (discrete) changes, but may be continuous changes.

Likewise, the number of polarization directions selectively set by the photography polarizer driving mechanism 1062 may be freely determined, and the manner of change in the polarization direction carried out by the photography polarizer driving mechanism 1062 may be either stepwise changes or continuous changes.

In the example shown in FIG. 9A and FIG. 9B, the controller 1030 executes control of the illumination polarizer driving mechanism 1061 and control of the photography polarizer driving mechanism 1062. The controller 1030 may execute the control of the illumination polarizer driving mechanism 1061 and the control of the photography polarizer driving mechanism 1062 in an interlocking manner. Also, the controller 1030 may execute the control of the illumination polarizer driving mechanism 1061 and the control of the photography polarizer driving mechanism 1062 independently of each other. In the case where only one of the illumination polarizer driving mechanism 1061 and the photography polarizer driving mechanism 1062 is provided, the controller 1030 executes control of this one polarizer driving mechanism.

The polarizer driving mechanism 1060 (the illumination polarizer driving mechanism 1061 and/or the photography polarizer driving mechanism 1062) may be configured to produce a relative change between the polarization direction of the illumination polarization component to be extracted from the slit illumination light by the illumination polarizer 1012 and the polarization direction of the photography polarization component to be extracted from the return light from the subject's eye E by the photography polarizer 1021. The polarizer driving mechanism 1060 configured in this manner is an example of the first polarizer driving mechanism.

In the case where the polarizer driving mechanism 1060 includes only the illumination polarizer driving mechanism 1061, the polarizer driving mechanism 1060 performs driving of the illumination polarizer 1012. By doing so, the polarizer driving mechanism 1060 may produce a relative change between the polarization direction of the illumination polarization component to be extracted from the slit illumination light by the illumination polarizer 1012 and the polarization direction of the photography polarization component to be extracted from the return light from the subject's eye E by the photography polarizer 1021.

Conversely, in the case where the polarizer driving mechanism 1060 includes only the photography polarizer driving mechanism 1062, the polarizer driving mechanism 1060 performs driving of the photography polarizer 1021. By doing so, the polarizer driving mechanism 1060 may produce a relative change between the polarization direction of the illumination polarization component to be extracted from the slit illumination light by the illumination polarizer 1012 and the polarization direction of the photography polarization component to be extracted from the return light from the subject's eye E by the photography polarizer 1021.

In the case where the polarizer driving mechanism 1060 includes both the illumination polarizer driving mechanism 1061 and the photography polarizer driving mechanism 1062, the polarizer driving mechanism 1060 performs either the driving of the illumination polarizer 1012 or the driving of the photography polarizer 1021. By doing so, the polarizer driving mechanism 1060 may produce a relative change between the polarization direction of the illumination polarization component to be extracted from the slit illumination light by the illumination polarizer 1012 and the polarization direction of the photography polarization component to be extracted from the return light from the subject's eye E by the photography polarizer 1021.

In addition to or in place of the above, the polarizer driving mechanism 1060 may perform both the driving of the illumination polarizer 1012 and the driving of the photography polarizer 1021, thereby producing a relative change between the polarization direction of the illumination polarization component to be extracted from the slit illumination light by the illumination polarizer 1012 and the polarization direction of the photography polarization component to be extracted from the return light from the subject's eye E by the photography polarizer 1021.

Since the ophthalmic apparatus 1300 of the present aspect is configured to perform the driving of the illumination polarizer 1012 for changing the polarization direction of the illumination polarization component to be extracted from the slit illumination light and/or the driving of the photography polarizer 1021 for changing the polarization direction of the photography polarization component to be extracted from the return light from the subject's eye E, the ophthalmic apparatus 1300 can perform photography and/or measurement using polarization under various conditions.

Further, since the ophthalmic apparatus 1300 of the present aspect is configured to produce a relative change between the polarization direction of the illumination polarization component to be extracted from the slit illumination light and the polarization direction of the photography polarization component to be extracted from the return light from the subject's eye E, the ophthalmic apparatus 1300 can change the combination of the polarization state of the light to be projected onto the subject's eye E and the polarization state of the light to be detected by the image sensor 1022 in various ways, and therefore photography and/or measurement can be conducted using polarization under various conditions.

Figure 10:
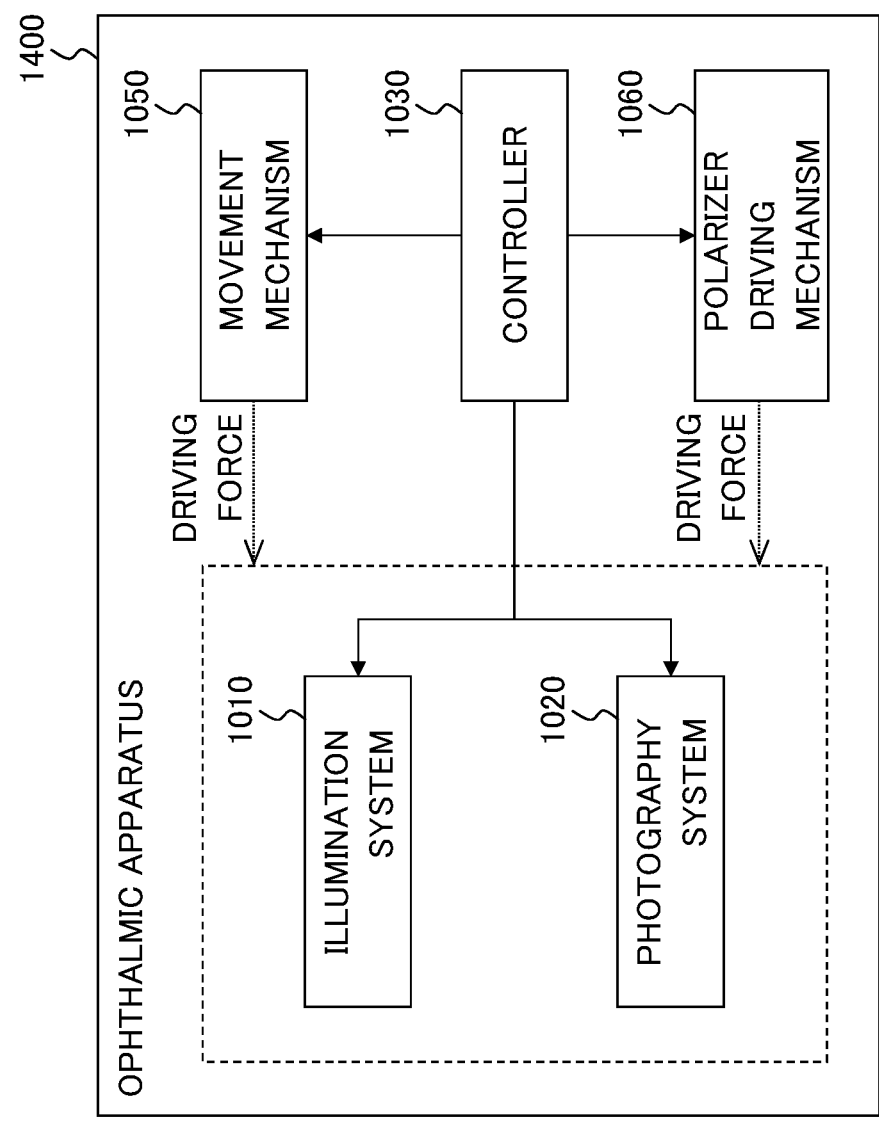
FIG. 10 is a diagram illustrating a configuration of an ophthalmic apparatus according to an aspect example of an embodiment.

FIG. 10 shows a configuration of an ophthalmic apparatus according to one aspect of the embodiment. The ophthalmic apparatus 1400 according to the present aspect includes the movement mechanism 1050 and the polarizer driving mechanism 1060, in addition to the illumination system 1010, the photography system 1020, and the controller 1030 which have the same or similar configurations as or to the corresponding components of the ophthalmic apparatus 1000.

The movement mechanism 1050 of the present aspect may have the same or a similar configuration as or to the movement mechanism 1500 included in the ophthalmic apparatus 1200 described in conjunction with FIG. 5 to FIG. 7B. Further, the polarizer driving mechanism 1060 of the present aspect may have the same or a similar configuration as or to the polarizer driving mechanism 1060 included in the ophthalmic apparatus 1300 described in conjunction with FIG. 8 to FIG. 9B. In this way, the ophthalmic apparatus 1400 of the present aspect may have, although not limited to this, a hardware configuration that combines the two ophthalmic apparatuses 1200 and 1300 described above.

The ophthalmic apparatus 1400 of the present aspect, which includes the movement mechanism 1050 and the polarizer driving mechanism 1060, can collect a series of Scheimpflug images (a Scheimpflug image group) from a three dimensional region of the subject's eye E, and also perform photography and/or measurement using polarization under various conditions. In other words, the ophthalmic apparatus 1400 of the present aspect can apply photography and/or measurement under various conditions using polarization to a three dimensional region of the subject's eye E.

The movement mechanism 1050 is configured to move the illumination system 1010 and the photography system 1020 in a predetermined direction (scanning direction). The scanning direction may be fixed or variable. In the case where the scanning direction is variable, the controller 1030 performs control of the movement mechanism 1050 to move the illumination system 1010 and the photography system 1020 in a scanning direction designated in advance.

The scanning direction is typically the lateral direction (horizontal direction) or the longitudinal direction (vertical direction). The lateral direction is oriented to be the direction from the inner corner to the outer corner of the subject's eye E, or the direction opposite thereto. The longitudinal direction is oriented to be the direction from the upper eyelid to the lower eyelid of the subject's eye E, or the direction opposite thereto. In some aspect examples, scanning may be conducted by rotating slit light about the optical axis of the subject's eye E or about an axis near the optical axis of the subject's eye E.

The scanning direction may be freely determined as described above, and further the relationship between the scanning direction and the polarization direction may also be freely determined. In other words, the relationship between the movement direction of the illumination system 1010 and the photography system 1020 produced by the movement mechanism 1050 and the polarization direction of the illumination polarization component to be extracted from the slit illumination light by the illumination polarizer 1012 may be freely determined. Likewise, the relationship between the movement direction of the illumination system 1010 and the photography system 1020 produced by the movement mechanism 1050 and the polarization direction of the photography polarization component to be extracted from the return light from the subject's eye E by the photography polarizer 1021 may be freely determined.

In some examples, the polarization direction of the illumination polarization component may be arranged to be perpendicular to the scanning direction and the polarization direction of the photography polarization component may be arranged to be parallel to the scanning direction.

Figure 11:
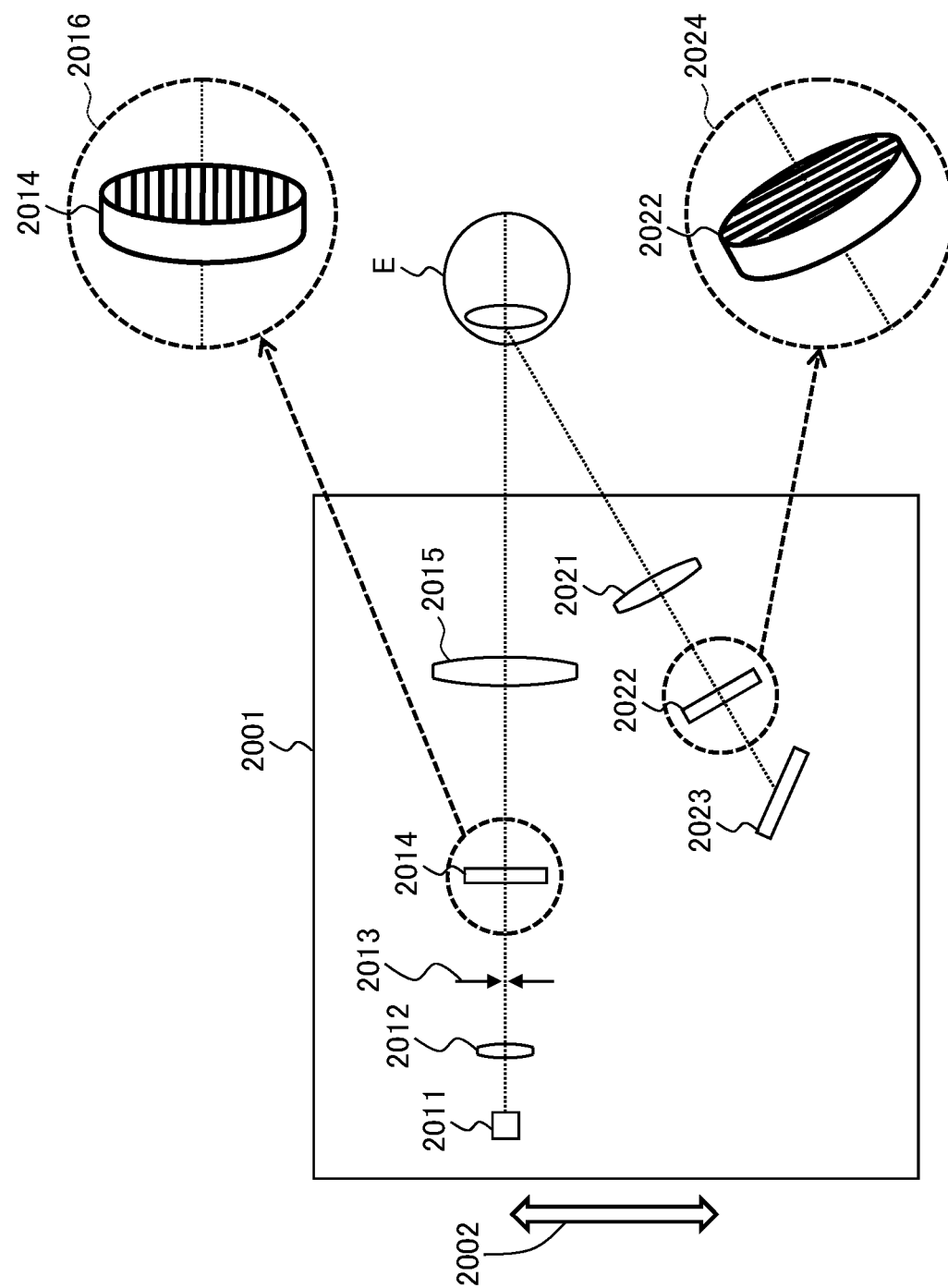
FIG. 11 is a diagram illustrating a configuration of an ophthalmic apparatus according to an aspect example of an embodiment.

FIG. 11 shows a specific example. In the present example, the photography unit 2001 that includes the illumination system and the photography system is moved in the scanning direction 2002 by the movement mechanism 1050. The illumination system and the photography system provided in the photography unit 2001 are configured to satisfy the Scheimpflug condition. FIG. 11 will be referred to for a purpose of giving a description of the relationship between the scanning direction and the polarization direction, and therefore some elements such as the controller 1030, the movement mechanism 1050, and the polarizer driving mechanism 1060 are not shown in FIG. 11.

The illumination system provided in the photography unit 2001 includes the following elements: the light source 2011 configured to emit light; the collimator lens 2012 configured to convert the light emitted from the light source 2011 into parallel light; the slit forming mechanism 2013 configured to generate slit illumination light from the parallel light generated by the collimator lens 2012; the polarizing plate 2014 configured to extract an illumination polarization component from the slit illumination light generated by the slit forming mechanism 2013; and the objective lens 2015 configured to project the illumination polarization component (parallel light) that has passed through the polarizing plate 2014 onto the subject's eye E. Note that the illumination system may include elements other than these.

The polarizing plate 2014 (polarizer) in the present example is arranged in such a manner as to extract a polarization component of parallel light, but the arrangement of the polarizer is not limited to this. The polarizer may be arranged in such a manner as to extract a polarization component of converging light or a polarization component of diverging light.

The photography system provided in the photography unit 2001 includes the following elements: the objective lens 2021 configured to convert return light from the subject's eye E with the illumination light (illumination polarization component) projected, into converging light; the polarizing plate 2022 configured to extract a photography polarization component from the converging return light generated by the objective lens 2021; and the image sensor 2023 configured to detect the photography polarization component extracted by the polarizing plate 2022. Note that the photography system may include elements other than these.

The polarizing plate 2014 of the illumination system, as shown in its enlarged perspective view 2016, is placed to selectively pass light oscillating in a direction perpendicular to the scanning direction 2002. In contrast, the polarizing plate 2022 of the photography system, as shown in its enlarged perspective view 2024, is placed to selectively pass light oscillating in a direction parallel to the scanning direction 2002.

Contrary to the above example, the polarization direction of the illumination polarization component may be oriented to be parallel to the scanning direction and the polarization direction of the photography polarization component may be oriented to be perpendicular to the scanning direction. Although illustration of the present example is omitted, the configuration of the present example may be achieved by rotating the polarizing plate 2014 of the illumination system in FIG. 11 by 90 degrees about the illumination optical axis, and rotating the polarizing plate 2022 of the photography system by 90 degrees about the photography optical axis.

By arranging the polarization direction of the illumination polarization component and the polarization direction of the photography polarization component in such a manner as to be perpendicular to each other as in the above examples, that is, by arranging the polarization direction of the illumination polarization component and the polarization direction of the photography polarization component in crossed nicols, diffuse reflection light from the subject's eye E can be selectively detect, and therefore a series of diffuse reflection images can be collected from a three dimensional region of the subject's eye E. Note that a diffuse reflection image is an image of light components whose polarization information has changed between before and after reflection at the subject's eye E.

In another example, both the polarization direction of the illumination polarization component and the polarization direction of the photography polarization component may be arranged to be perpendicular to the scanning direction. Conversely, both the polarization direction of the illumination polarization component and the polarization direction of the photography polarization component may be arranged to be parallel to the scanning direction. By arranging, as in these examples, the polarization direction of the illumination polarization component and the polarization direction of the photography polarization component parallel to each other, that is, by arranging the polarization direction of the illumination polarization component and the polarization direction of the photography polarization component in parallel nicols, specular reflection light can be selectively detected by the subject's eye E, and therefore a series of specular reflection images can be collected from a three dimensional region of the subject's eye E. Note that a specular reflection image is an image of light components whose polarization information has not changed between before and after reflection at the subject's eye E.

According to the ophthalmic apparatus 1400 of the present aspect, it becomes possible to change the relationship between the movement direction of the illumination system 1010 and the photography system 1020 produced by the movement mechanism 1050, and the polarization direction of the illumination polarization component to be extracted from the slit illumination light by the illumination polarizer 1012.

Likewise, the ophthalmic apparatus 1400 of the present aspect is also capable of changing the relationship between the movement direction of the illumination system 1010 and the photography system 1020 produced by the movement mechanism 1050, and the polarization direction of the photography polarization component to be extracted from the return light from the subject's eye E by the photography polarizer 1021.

In some examples, the ophthalmic apparatus 1400 may be configured to combine the operation of changing the polarization direction of the illumination polarization component and/or the polarization direction of the photography polarization component, and the operation of scanning a three dimensional region of the subject's eye E. According to such examples, two or more pieces of Scheimpflug image groups corresponding to two or more different polarization directions can be collected.

Figure 12:
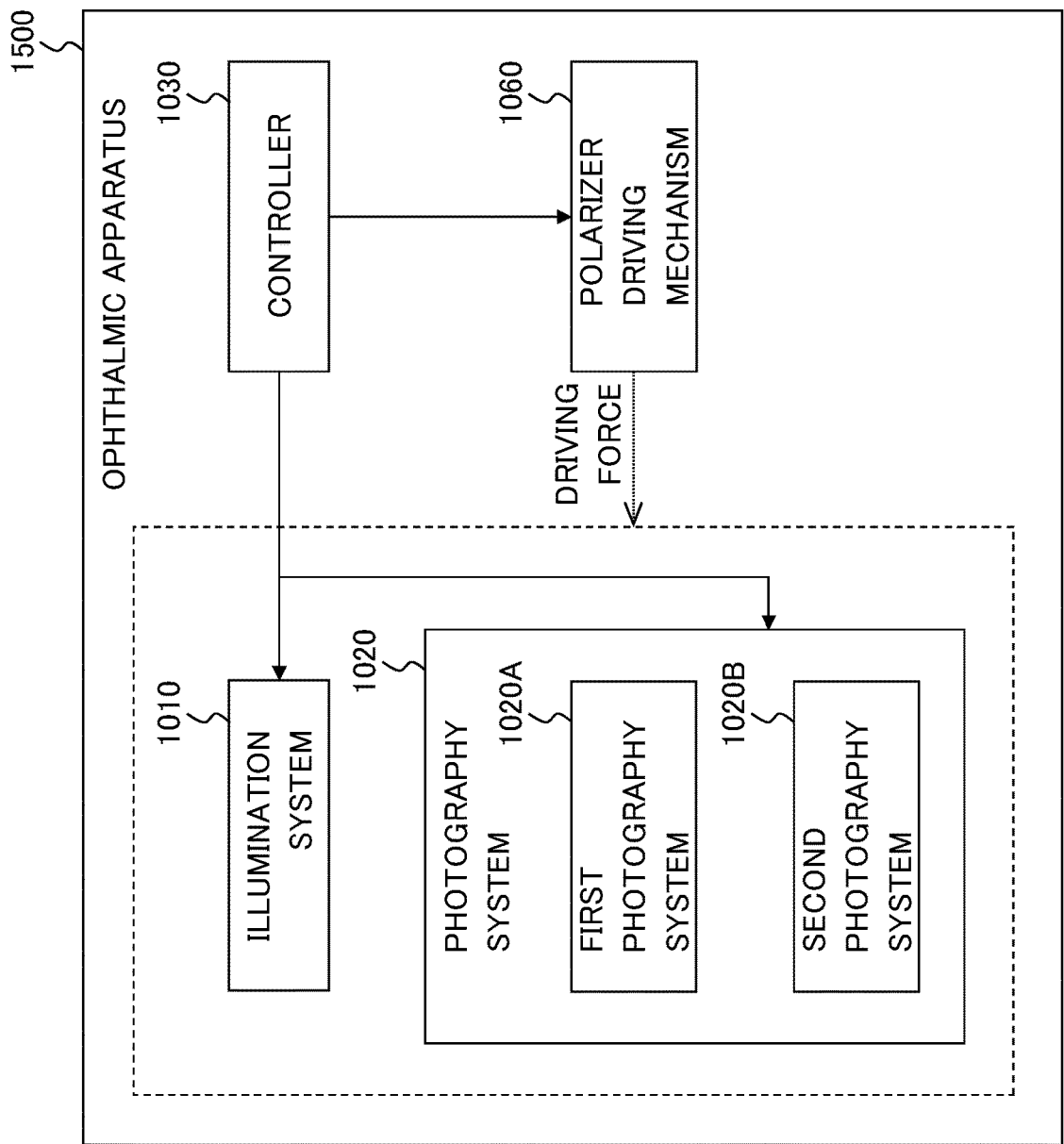
FIG. 12 is a diagram illustrating a configuration of an ophthalmic apparatus according to an aspect example of an embodiment.
Figure 13:
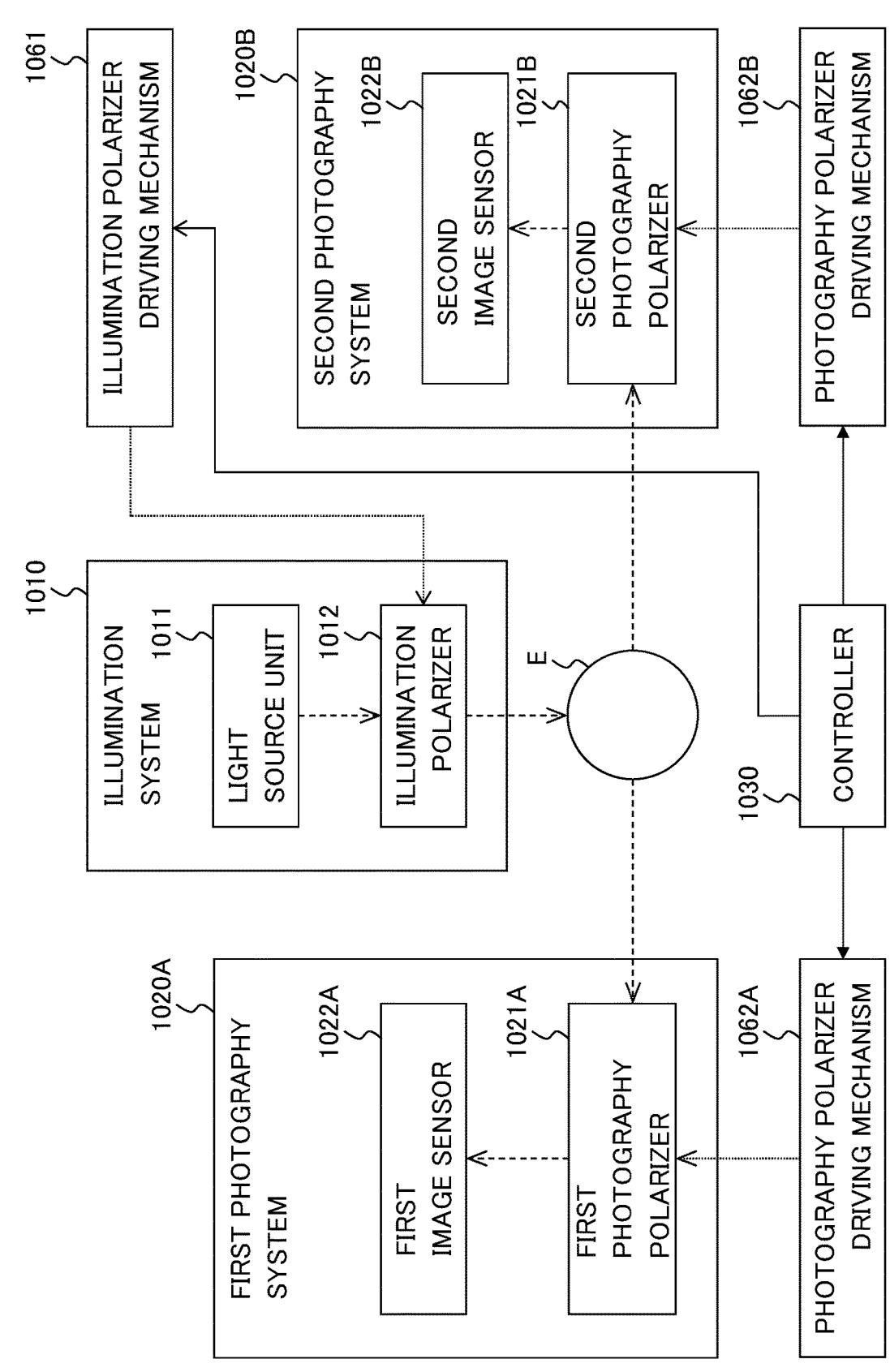
FIG. 13 is a diagram illustrating a configuration and an operation of an ophthalmic apparatus according to an aspect example of an embodiment.

FIG. 12 and FIG. 13 show a configuration of an ophthalmic apparatus according to one aspect of the embodiment. The ophthalmic apparatus 1500 according to the present aspect includes the illumination system 1010, the photography system 1020, and the controller 1030, and the polarizer driving mechanism 1060 which have the same or similar configurations as or to the corresponding components of the ophthalmic apparatus 1300.

The photography system 1020 of the present aspect includes the first photography system 1020A and the second photography system 1020B. The illumination system 1010 and the first photography system 1020A are configured to satisfy the Scheimpflug condition, and the illumination system 1010 and the second photography system 1020B are configured to satisfy the Scheimpflug condition. Note that the number of photography systems is not limited to two pieces, and may be three or more pieces.

The first photography system 1020A and the second photography system 1020B are arranged in mutually different directions with respect to the subject's eye E. In other words, the first photography system 1020A and the second photography system 1020B are arranged to conduct photography of the subject's eye E from mutually different directions.

In some aspect examples, the first photography system 1020A and the second photography system 1020B are positioned in opposite directions to each other with respect to the illumination system 1010. In this case, the relative position of the first photography system 1020A with respect to the illumination system 1010 and the relative position of the second photography system 1020B with respect to the illumination system 1010 may be symmetrical or asymmetrical. For example, the angle formed by the optical axis of the first photography system 1020A (the first photography optical axis) with respect to the optical axis of the illumination system 1010 (the illumination optical axis) and the angle formed by the optical axis of the second photography system 1020B (the second photography optical axis) with respect to the illumination optical axis, may be equal to or different from one another.

A more detailed description of the configuration and the operation of the ophthalmic apparatus 1500 will be given with reference to FIG. 13. The first photography system 1020A includes the first photography polarizer 1021A and the first image sensor 1022A. The first photography polarizer 1021A is configured to extract a photography polarization component (the first photography polarization component) from return light (the first return light) from the subject's eye E to which the slit illumination light is projected. The first image sensor 1022A is configured to detect the first photography polarization component extracted by the first photography polarizer 1021A.

Similarly, the second photography system 1020B includes the second photography polarizer 1021B and the second image sensor 1022B. The second photography polarizer 1021B is configured to extract a photography polarization component (the second photography polarization component) from return light (the second return light) from the subject's eye E to which the slit illumination light is projected. The second image sensor 1022B is configured to detect the second photography polarization component extracted by the second photography polarizer 1021B.

In other words, the photography polarizer of the present aspect includes the first photography polarizer 1021A provided in the first photography system 1020A and the second photography polarizer 1021B provided in the second photography system 1020B. Further, the image sensor of the present aspect includes the first image sensor 1022A provided in the first photography system 1020A and the second image sensor 1022B provided in the second photography system 1020B.

Here, the first return light is the light that has entered the first photography system 1020A, and the second return light is the light that has entered the second photography system 1020B. In addition, the polarization direction of the first photography polarization component and the polarization direction of the second photography polarization component may be the same as or different from each other.

The polarizer driving mechanism 1060 of the present example includes the illumination polarizer driving mechanism 1061, the first photography polarizer driving mechanism 1062A, and the second photography polarizer driving mechanism 1062B.

The illumination polarizer driving mechanism 1061 is configured to perform driving of the illumination polarizer 1012 for changing the polarization direction of the illumination polarization component extracted from the slit illumination light.

The first photography polarizer driving mechanism 1062A is configured to perform driving of the first photography polarizer 1021A for changing the polarization direction of the first photography polarization component extracted from the first return light from the subject's eye E.

Likewise, the second photography polarizer driving mechanism 1062B is configured to perform driving of the second photography polarizer 1021B for changing the polarization direction of the second photography polarization component extracted from the second return light from the subject's eye E.

In the example shown in FIG. 13, the polarizer driving mechanism 1060 includes the illumination polarizer driving mechanism 1061 and the two pieces of photography polarizer driving mechanisms, namely, the photography polarizer driving mechanisms 1062A and 1062B. In another example, however, the polarizer driving mechanism 1060 may only include the two photography polarizer driving mechanisms 1062A and 1062B without including the illumination polarizer driving mechanism 1061.

In the example shown in FIG. 13, the polarizer driving mechanism 1060 includes the two photography polarizer driving mechanisms 1062A and 1062B. In another example, however, the polarizer driving mechanism 1060 may include a single photography polarizer driving mechanism 1062. In the case of having only a single photography polarizer driving mechanism 1062, one of the polarization direction of the first photography polarization component and the polarization direction of the second photography polarization component is fixed and the other is variable.

In some aspect examples, three or more pieces of photography systems are provided. In such aspects, the polarizer driving mechanism 1060 may include three or more pieces of photography polarizer driving mechanisms corresponding to the three or more pieces of photography systems. Alternatively, the polarizer driving mechanism 1060 may include one or more pieces of photography polarizer driving mechanisms corresponding to one or more pieces of photography systems out of the three or more pieces of photography systems.

In the example shown in FIG. 13, the controller 1030 is configured to perform control of the illumination polarizer driving mechanism 1061, control of the first photography polarizer driving mechanism 1062A, and control of the second photography polarizer driving mechanism 1062B. The controller 1030 may perform the control of the illumination polarizer driving mechanism 1061 and one of or both the control of the first photography polarizer driving mechanism 1062A and the control of the second photography polarizer driving mechanism 1062B, in an interlocking manner or independently of each other. Further, the controller 1030 may perform the control of the first photography polarizer driving mechanism 1062A and the control of the second photography polarizer driving mechanism 1062B in an interlocking manner or independently of each other.

The polarizer driving mechanism 1060 (the first photography polarizer driving mechanism 1062A and/or the second photography polarizer driving mechanism 1062B) of the present aspect may be configured to produce a relative change between the polarization direction of the first photography polarization component and the polarization direction of the second photography polarization component. Here, the first photography polarization component is extracted by the first photography polarizer 1021A from the first return light from the subject's eye E, and the second photography polarization component is extracted by the second photography polarizer 1021B from the second return light from the subject's eye E. The polarizer driving mechanism 1060 configured in this manner is an example of the second polarizer driving mechanism.

Furthermore, the polarizer driving mechanism 1060 according to the example shown in FIG. 13 may be configured to produce a relative change between the polarization direction of the illumination polarization component extracted from the slit illumination light by the illumination polarizer 1012 and the polarization direction of the first photography polarization component extracted from the first return light from the subject's eye E by the first photography polarizer 1021A, and/or, to produce a relative change between the polarization direction of the illumination polarization component extracted from the slit illumination light by the illumination polarizer 1012 and the polarization direction of the second photography polarization component extracted from the second return light from the subject's eye E by the second photography polarizer 1021B. The polarizer driving mechanism 1060 configured in this way is an example of a combination of the first polarizer driving mechanism and the second polarizer driving mechanism.

According to the ophthalmic apparatus 1500 of the present aspect, photography and/or measurement using polarization can be conducted with two or more pieces of photography systems. This can provide an improvement in the efficiency of the photography and/or measurement. For example, the time required for photographing and/or measurement can be shortened by means of simultaneous execution of two or more times of polarization-based photography and/or measurement using two or more pieces of photography systems.

According to the ophthalmic apparatus 1500 of the present aspect, it becomes possible to produce a relative change between the polarization direction of the first photography polarization component extracted from the first return light from the subject's eye E by the first photography polarizer 1021A and the polarization direction of the second photography polarization component extracted from the second return light from the subject's eye E by the second photography polarizer 1021B. As a consequence, the ophthalmic apparatus 1500 can perform photography and/or measurement using polarization efficiently and under various conditions.

According to the ophthalmic apparatus 1500 of the present aspect, one or both of the following operations can be performed: the operation of driving the illumination polarizer 1012 for changing the polarization direction of the illumination polarization component extracted from the slit illumination light; and the operation of driving the first photography polarizer 1021A and/or the operation of driving the second photography polarizer 1021B for changing the polarization direction of the photography polarization component extracted from the return light from the subject's eye E. As a result of this, the ophthalmic apparatus 1500 can perform photography and/or measurement using polarization under various conditions.

According to the ophthalmic apparatus 1500 of the present aspect, it becomes possible to produce a relative change between the polarization direction of the illumination polarization component extracted from the slit illumination light and the polarization direction of the polarization component extracted from the return light from the subject's eye E (the first photography polarization component and/or the second photography polarization component). With this, the ophthalmic apparatus 1500 can change the combination of the polarization state of the light projected onto the subject's eye E and the polarization state of the light detected by the image sensor 1022 (the first image sensor 1022A and/or the second image sensor 1022B) in various ways. As a result, the ophthalmic apparatus 1500 can perform photography and/or measurement using polarization under various conditions.

Figure 14:
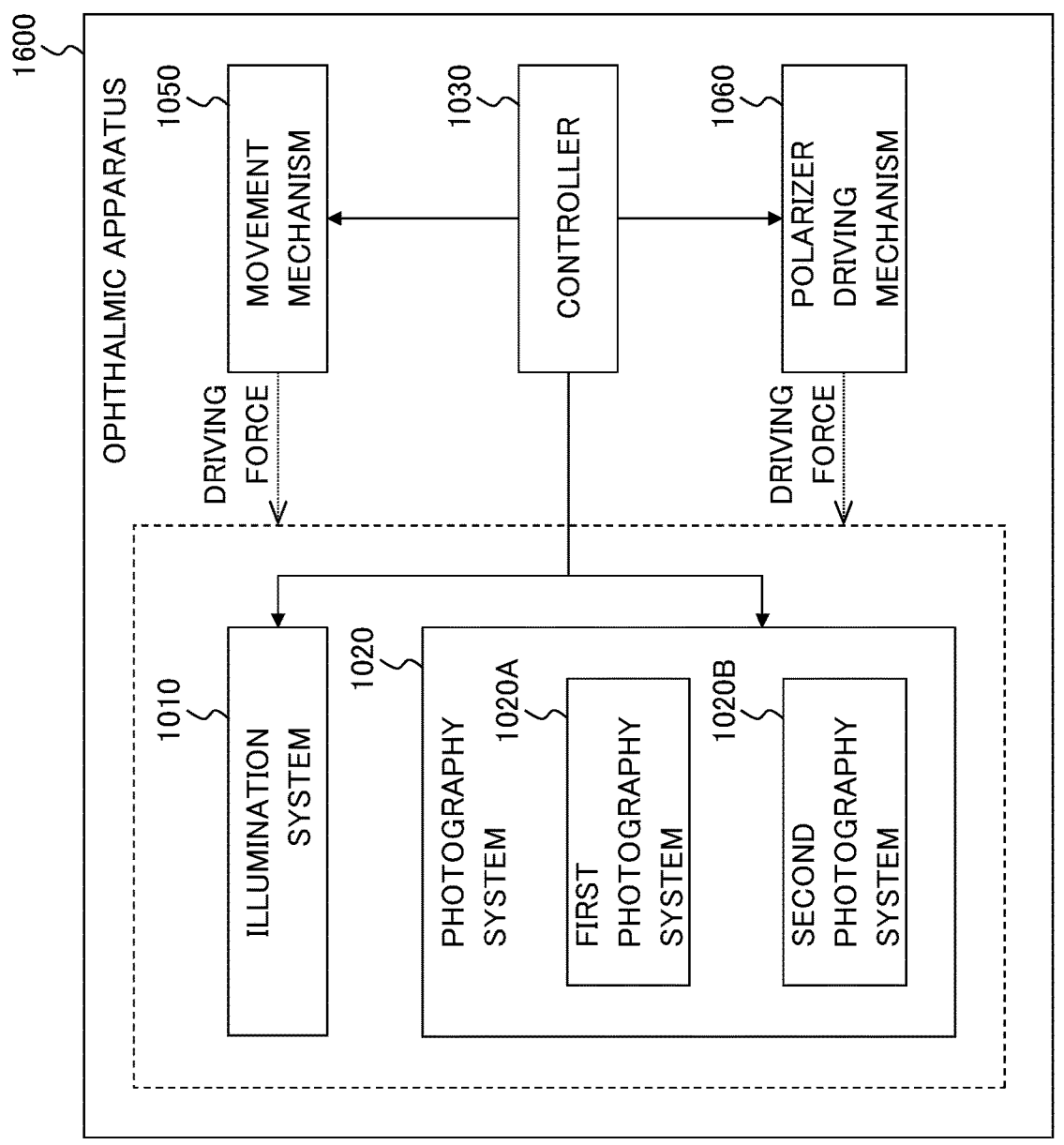
FIG. 14 is a diagram illustrating a configuration of an ophthalmic apparatus according to an aspect example of an embodiment.

FIG. 14 shows a configuration of an ophthalmic apparatus according to one aspect of the embodiment. The ophthalmic apparatus 1600 according to the present aspect includes the movement mechanism 1050, in addition to the illumination system 1010, the photography system 1020 (the first photography system 1020A and the second photography system 1020B), the controller 1030, and the polarizer driving mechanism 1060 which have the same or similar configurations as or to the corresponding components of the ophthalmic apparatus 1500. The ophthalmic apparatus 1600 of the present aspect can also be regarded as a combination of the ophthalmic apparatus 1400 that includes the movement mechanism 1050 and the polarizer driving mechanism 1060, and the ophthalmic apparatus 1500 that includes the first photography system 1020A and the second photography system 1020B.

Since the ophthalmic apparatus 1600 of the present aspect includes the movement mechanism 1050 and the polarizer driving mechanism 1060, the ophthalmic apparatus 1600 can perform photography and/or measurement of a three dimensional region of the subject's eye E under various conditions using polarization. Furthermore, since the ophthalmic apparatus 1600 of the present aspect includes two or more pieces of photography systems, it becomes possible to provide an improvement in the efficiency of photographing and/or measurement. Therefore, the ophthalmic apparatus 1600 of the present aspect can efficiently perform photography and/or measurement of a three dimensional region of the subject's eye E based on various conditions using polarization.

In the present aspect, the movement direction of the illumination system 1010 and the photography system 1020 produced by the movement mechanism 1050 (the scanning direction) may be freely determined. In addition to this, the relationship between the scanning direction and the polarization direction of the photography polarization component extracted from the return light from the subject's eye E by the photography polarizer 1021 may also be freely determined. Here, the photography polarizer 1021 includes the first photography polarizer 1021A and/or the second photography polarizer 1021B, and the photography polarization component correspondingly includes the first photography polarization component and/or the second photography polarization component.

For example, the polarization direction of the illumination polarization component may be arranged to be perpendicular to the scanning direction, and the polarization direction of the first photography polarization component and the polarization direction of the second photography polarization component both may be arranged to be parallel to the scanning direction.

Figure 15:
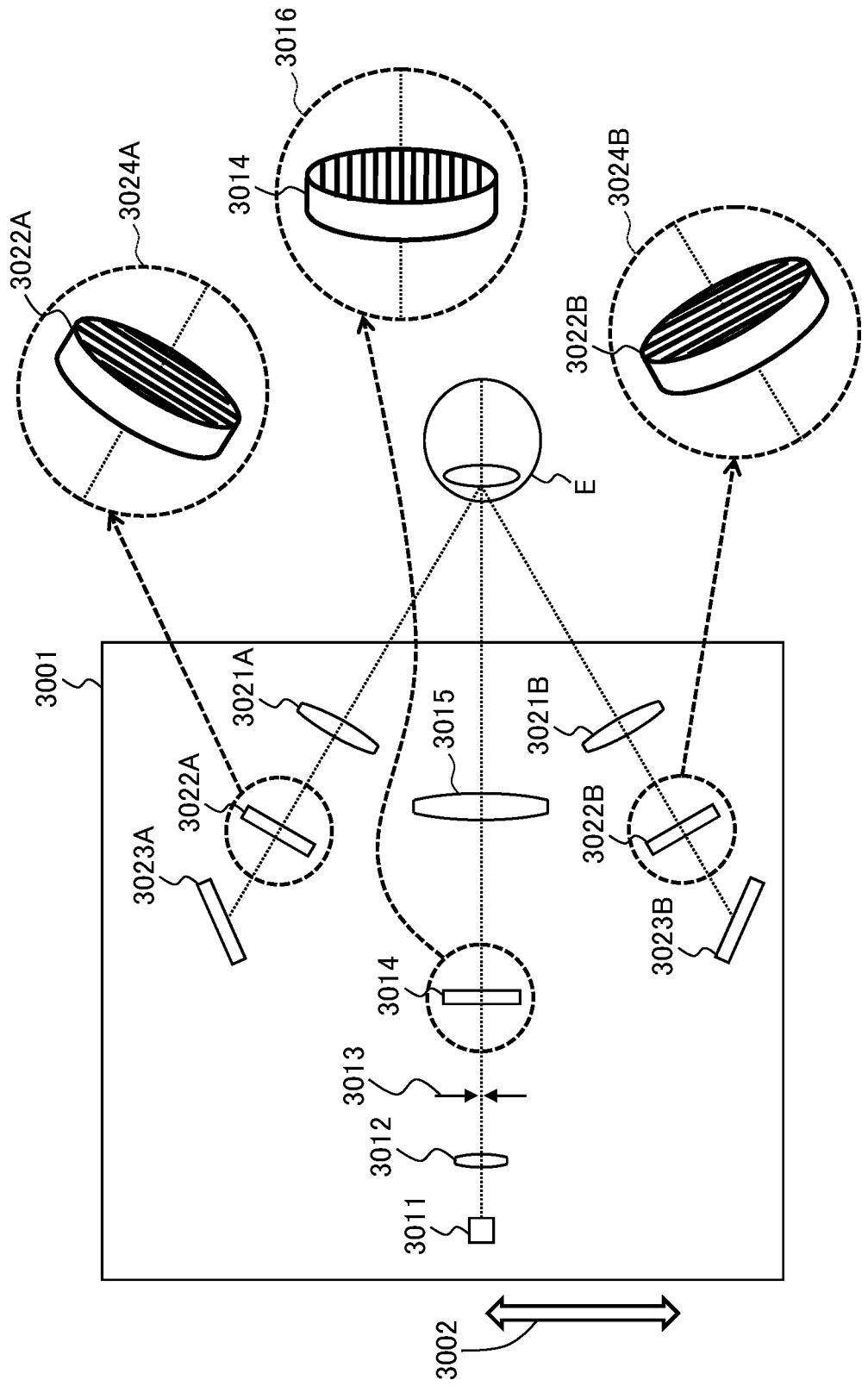
FIG. 15 is a diagram illustrating a configuration of an ophthalmic apparatus according to an aspect example of an embodiment.

FIG. 15 shows a specific example. In the present example, the photography unit 3001 that includes the illumination system and the photography system, is moved in the scanning direction 3002 by the movement mechanism 1050. The illumination system and the photography system provided in the photography unit 3001 are configured to satisfy the Scheimpflug condition. FIG. 15 will be referred to for a purpose of giving a description of the relationship between the scanning direction and the polarization direction, and therefore some elements such as the controller 1030, the movement mechanism 1050, the polarizer driving mechanism 1060 are not shown in FIG. 15.

The illumination system provided in the photography unit 3001 includes the following elements: the light source 3011 configured to emit light; the collimator lens 3012 configured to convert the light emitted from the light source 3011 into parallel light; the slit forming mechanism 3013 configured to generate slit illumination light from the parallel light generated by the collimator lens 3012; the polarizing plate 3014 configured to extract an illumination polarization component from the slit illumination light generated by the slit forming mechanism 3013; and the objective lens 3015 configured to project the illumination polarization component (parallel light) that has passed through the polarizing plate 3014 onto the subject's eye E. Note that the illumination system may include elements other than these.

The polarizing plate 3014 (polarizer) in the present example is arranged in such a manner as to extract the polarization component of parallel light, but the arrangement of the polarizer is not limited to this. The polarizer may be arranged in such a manner as to extract a polarization component of converging light or a polarization component of diverging light.

The photography unit 3001 includes the first photography system and the second photography system.

The first photography system includes the following elements: the first objective lens 3021A configured to convert first return light from the subject's eye E with the illumination light (illumination polarization component) projected, into converging light; the first polarizing plate 3022A configured to extract the first photography polarization component from the first converging return light generated by the first objective lens 3021A; and the first image sensor 3023A configured to detect the first photography polarization component extracted by the first polarizing plate 3022A.

Likewise, the second photography system includes the following elements: the second objective lens 3021B configured to convert second return light from the subject's eye E with the illumination light (illumination polarization component) projected, into converging light; the second polarizing plate 3022B configured to extract the second photography polarization component from the second converging return light generated by the second objective lens 3021B, and the second image sensor 3023B configured to detect the second photography polarization component extracted by the second polarizing plate 3022B.

It should be noted that the first photography system and the second photography system may include elements other than those described above.

The polarizing plate 3014 of the illumination system, as shown in its enlarged perspective view 3016, is placed to selectively pass light oscillating in a direction perpendicular to the scanning direction 3002. In contrast, the first polarizing plate 3022A, as shown in its enlarged perspective view 3024A, is placed to selectively pass light oscillating in a direction parallel to the scanning direction 3002. Likewise, the second polarizing plate 3022B, as shown in its enlarged perspective view 3024B, is placed to selectively pass light oscillating in a direction parallel to the scanning direction 3002.

Contrary to the above example, the polarization direction of the illumination polarization component may be oriented to be parallel to the scanning direction, and the polarization direction of the first photography polarization component and/or the polarization direction of the second photography polarization component may be oriented to be perpendicular to the scanning direction. Although illustration of the present example is omitted, the configuration of the present example may be achieved by rotating the polarizing plate 3014 of the illumination system in FIG. 15 by 90 degrees about the illumination optical axis, and rotating the first polarizing plate 3022A by 90 degrees about the first photography optical axis (and/or rotating the second polarizing plate 3022B by 90 degrees about the second photography optical axis).

In another example, both the polarization direction of the illumination polarization component and the polarization direction of the photography polarization component (the first photography polarization component and/or the second photography polarization component) may be arranged to be perpendicular to the scanning direction. Conversely, both the polarization direction of the illumination polarization component and the polarization direction of the photography polarization component (the first photography polarization component and/or the second photography polarization component) may be arranged to be parallel to the scanning direction.

The types or kinds of images that can be obtained by various combinations of the polarization direction of the illumination polarization component and the polarization direction of the photography polarization component have been described above. For example, a diffuse reflection image is obtained in the case of crossed nicols, and a specular reflection image is obtained in the case of parallel nicols.

According to the ophthalmic apparatus 1600 of the present aspect, different types or kinds of images can be acquired simultaneously by making the polarization direction of the first photography polarization component and the polarization direction of the second photography polarization component different from each other. For example, generation of a specular reflection image by the first photography system 1020A and generation of a diffuse reflection image by the second photography system 1020B can be carried out at the same time by performing photography of the subject's eye E in the state where the polarization direction of the illumination polarization component and the polarization direction of the first photography polarization component are parallel to each other and where the polarization direction of the illumination polarization component and the polarization direction of the second photography polarization component are perpendicular to each other.

It should be noted that combinations of the types or kinds of images acquired at the same time are not limited to the combination of a specular reflection image and a diffuse reflection image.

Figure 16:
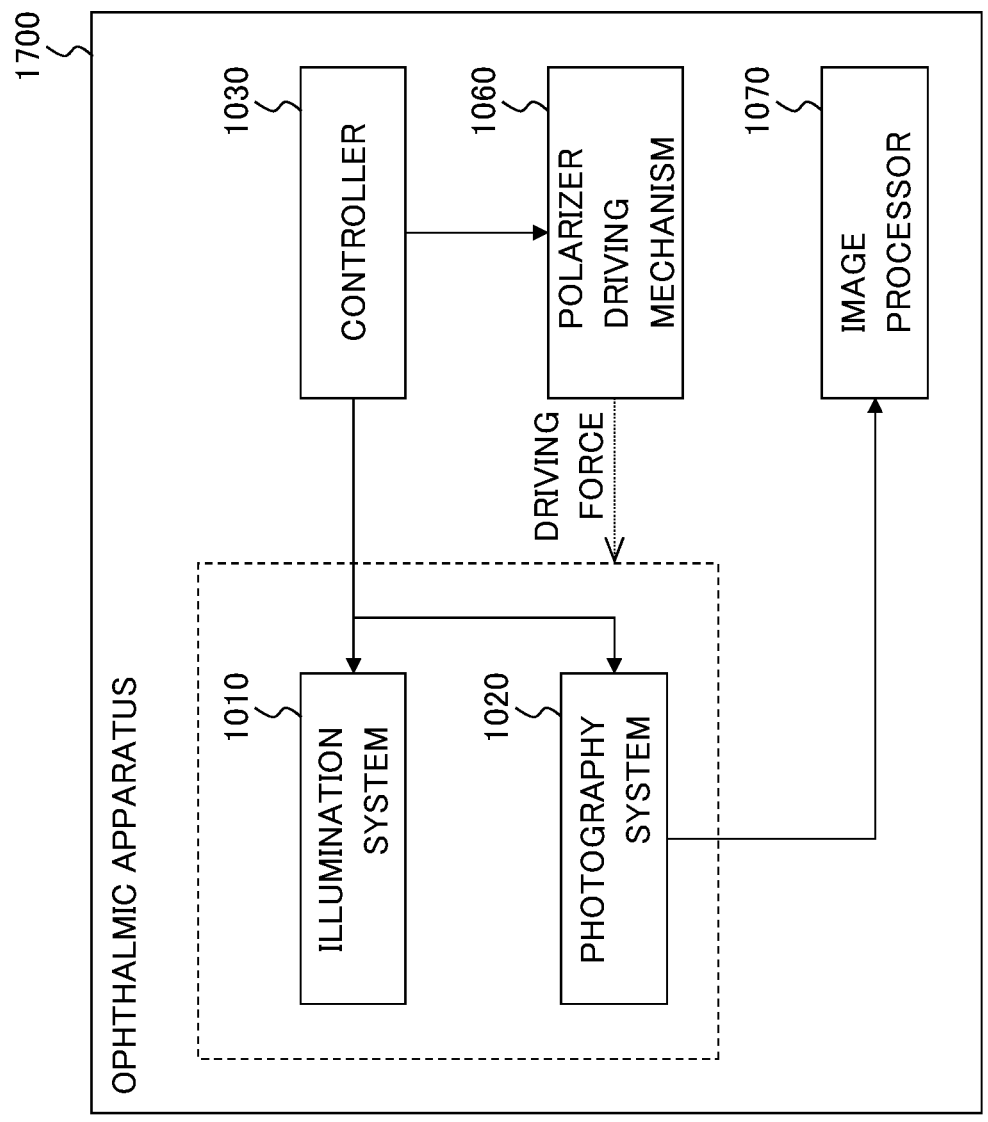
FIG. 16 is a diagram illustrating a configuration of an ophthalmic apparatus according to an aspect example of an embodiment.

FIG. 16 shows a configuration of an ophthalmic apparatus according to one aspect of the embodiment. The ophthalmic apparatus 1700 according to the present aspect includes the image processor 1070 in addition to the illumination system 1010, the photography system 1020, the controller 1030, and the polarizer driving mechanism 1060 which have the same or similar configurations as or to the corresponding components of the ophthalmic apparatus 1300.

The image processor 1070 is configured to process an image of the subject's eye E generated by the ophthalmic apparatus 1700. The image processor 1070 includes hardware elements such as a processor and a storage device. The storage device retains a computer program such as an image processing program. One or more of the functions of the image processor 1070 are implemented by cooperation of software such as the image processing program and hardware such as the processor.

Figure 17:
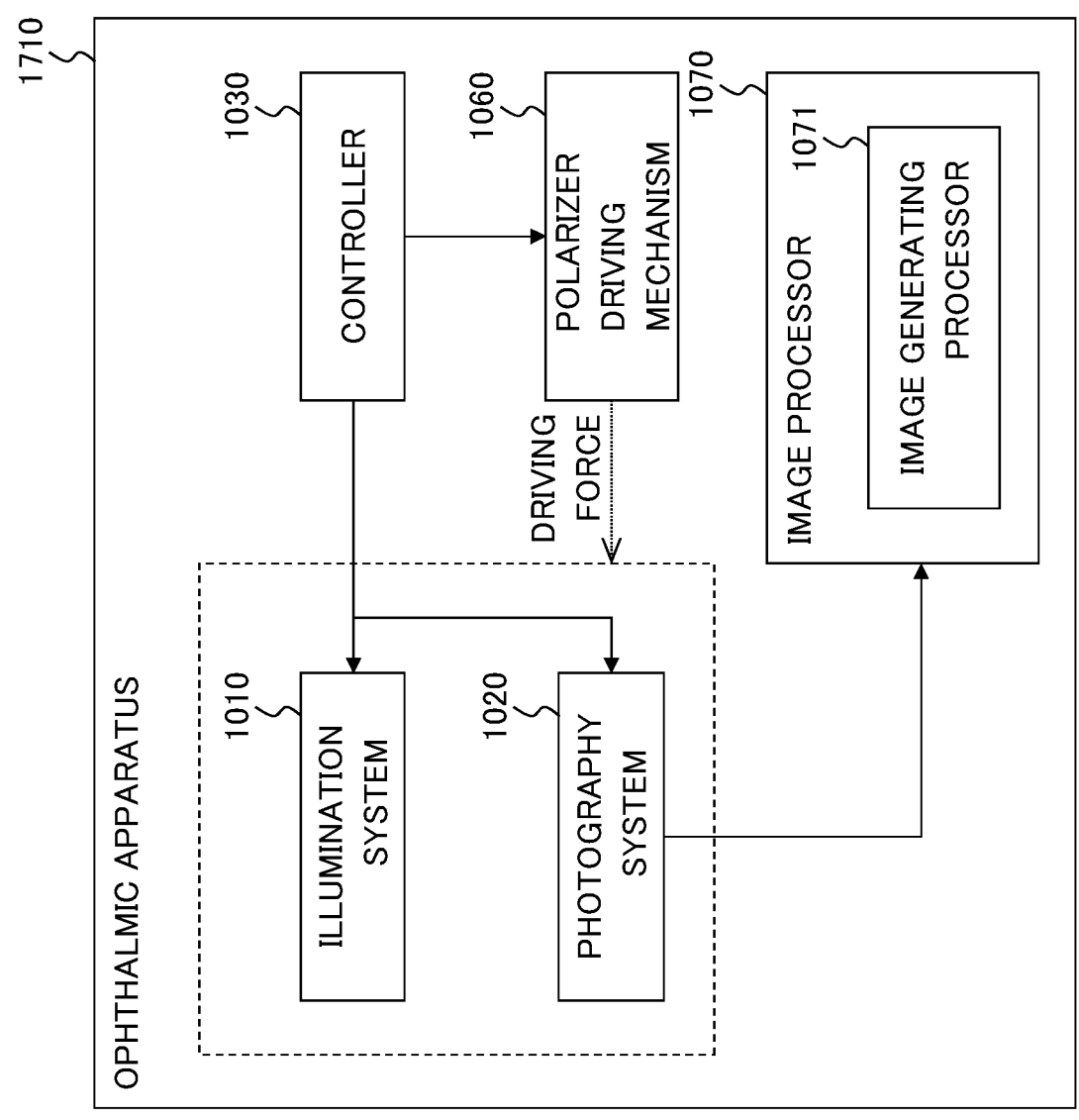
FIG. 17 is a diagram illustrating a configuration of an ophthalmic apparatus according to an aspect example of an embodiment.

The types or kinds of processing applied to an image of the subject's eye E by the image processor 1070 may be freely selected. FIG. 17 shows one example of the image processor 1070. The image processor 1070 of the ophthalmic apparatus 1710 of the present example includes the image generating processor 1071.

The image generating processor 1071 is configured to generate another image (a new image) from an image of the subject's eye E generated by the ophthalmic apparatus 1710. The image generating processor 1071 includes hardware elements such as a processor and a storage device. The storage device retains a computer program such as an image generating program. One or more of the functions of the image generating processor 1071 are implemented by cooperation of software such as the image generating program and hardware such as the processor.

One example of the operation performed by the ophthalmic apparatus 1710 will be described with further reference to FIG. 18. To begin with, the controller 1030 executes control of the polarizer driving mechanism 1060 to arrange the illumination polarizer 1012 and the photography polarizer 1021 in a state of crossed nicols. The illumination system 1010 and the photography system 1020 perform photography of the subject's eye E in this state of crossed nicols (S1). This photography generates a diffuse reflection image of the subject's eye E.

Further, the controller 1030 executes control of the polarizer driving mechanism 1060 to arrange the illumination polarizer 1012 and the photography polarizer 1021 in a state of parallel nicols. The illumination system 1010 and the photography system 1020 perform photography of the subject's eye E in this state of parallel nicols (S2). This photography generates a specular reflection image of the subject's eye E.

In another operation example, the step of acquiring a diffuse reflection image may be performed after the step of acquiring a specular reflection image. In yet another operation example, the step of acquiring a specular reflection image and the step of acquiring a diffuse reflection image may be performed in parallel by employing the first photography system 1020A and the second photography system 1020B.

Furthermore, the image generating processor 1071 generates an image containing no specular reflection noise on the basis of the diffuse reflection image acquired in the step S1 and the specular reflection image acquired in the step S2 (S3).

Figure 19:
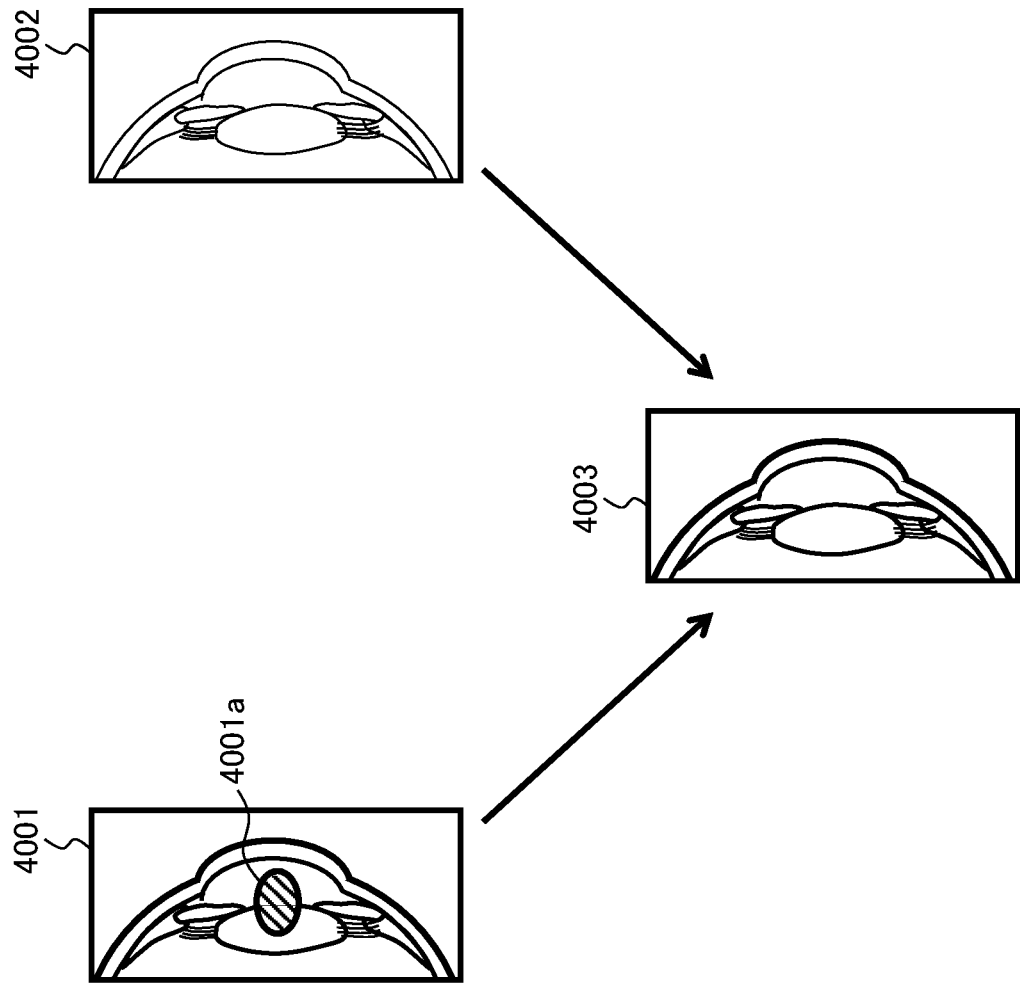
FIG. 19 is a diagram used for explaining processing executed by an ophthalmic apparatus according to an aspect example of an embodiment.

A specific example of the processing of the step S3 will be described with further reference to FIG. 19. In the present example, the ophthalmic apparatus 1710 performs anterior segment imaging on the subject's eye E. The reference character 4001 denotes the specular reflection image acquired in the step S2 and the reference character 4002 denotes the diffuse reflection image acquired in the step S1. Generally, in anterior segment imaging, Scheimpflug imaging is conducted using a relatively large amount of illumination light. Therefore, the specular reflection image 4001 contains the image 4001a of strong reflection from the anterior segment. The reflection image 4001a is specular reflection noise. On the other hand, the diffuse reflection image 4002 does not contain any specular reflection noise.

In the step S3, the image generating processor 1071 first analyzes the specular reflection image 4001 to identify an image region (specular reflection noise region) corresponding to the specular reflection noise 4001a. This specular reflection noise region identification process may include, for example, any known image segmentation, any known anterior segment shape analysis, or the like.

The specular reflection noise region identification process may be executed using an inference model constructed by machine learning. For example, this inference model may be constructed by applying machine learning using training data that includes a set of ocular images to a neural network (e.g., a convolutional neural network). Here, the set of ocular images may include Scheimpflug images of eyes and/or ocular images acquired with other modalities. The constructed inference model functions to receive an input of a Scheimpflug image of an eye and to output information indicating a specular reflection noise region in this Scheimpflug image. The information to be output may be, for example, a specular reflection noise region itself, a coordinate indicating the area of a specular reflection noise region, a figure (shape, geometric shape) representing the area of a specular reflection noise region (e.g., a figure obtained by tracing the contour of a specular reflection noise), or the like.

Next, the image generating processor 1071 identifies an image region in the diffuse reflection image that positionally corresponds to the specular reflection noise region identified from the specular reflection image 4001. The image region identified is referred to as a corresponding region. This corresponding region identifying process may include, for example, registration between the specular reflection image 4001 and the diffuse reflection image 4002.

In the case where the ophthalmic apparatus 1710 includes two (or more) photography systems and also the specular reflection image 4001 and the diffuse reflection image 4002 are acquired at the same time, the image generating processor 1071 of some examples may perform registration between the specular reflection image 4001 and the diffuse reflection image 4002 based on the (known) positional relationship between the two photography systems.

On the other hand, in the case where the specular reflection image 4001 and the diffuse reflection image 4002 are acquired at mutually different times, the image generating processor 1071 of some examples may execute detection of a feature point from the specular reflection image 4001, detection of a feature point from the diffuse reflection image 4002, and registration between the specular reflection image 4001 and the diffuse reflection image 4002 using the feature point detected from the specular reflection image 4001 and the feature point detected from the diffuse reflection image 4002.

Subsequently, the image generating processor 1071 executes processing of the specular reflection noise region in the specular reflection image 4001 on the basis of the corresponding region identified from the diffuse reflection image 4002. As an example, this processing may include a process of replacing the specular reflection noise region with a corresponding region. As another example, the processing may include a process of enhancing the image quality of the corresponding region and a process of replacing the specular reflection noise region with the corresponding region having the enhanced image quality. As yet another example, the processing may include a process of synthesizing (composing) the specular reflection noise region and the corresponding region. As still another example, the processing may include a process of enhancing the image quality of the corresponding region and a process of synthesizing (composing) the corresponding region with the enhanced image quality and the specular reflection noise region.

The image generating processor 1071 generates another image (new image) 4003 that contains no specular reflection noise, from the specular reflection image 4001 containing specular reflection noise and the diffuse reflection image 4002 containing no specular reflection noise.

While having the same advantages, such as good brightness and high definition, as the specular reflection image 4001, the image 4003 generated in this way does not contain specular reflection noise. These advantages make the image 4003 appropriate and useful for diagnosis (e.g., observation, analysis, evaluation, etc.) of the subject's eye E.

Figure 20:
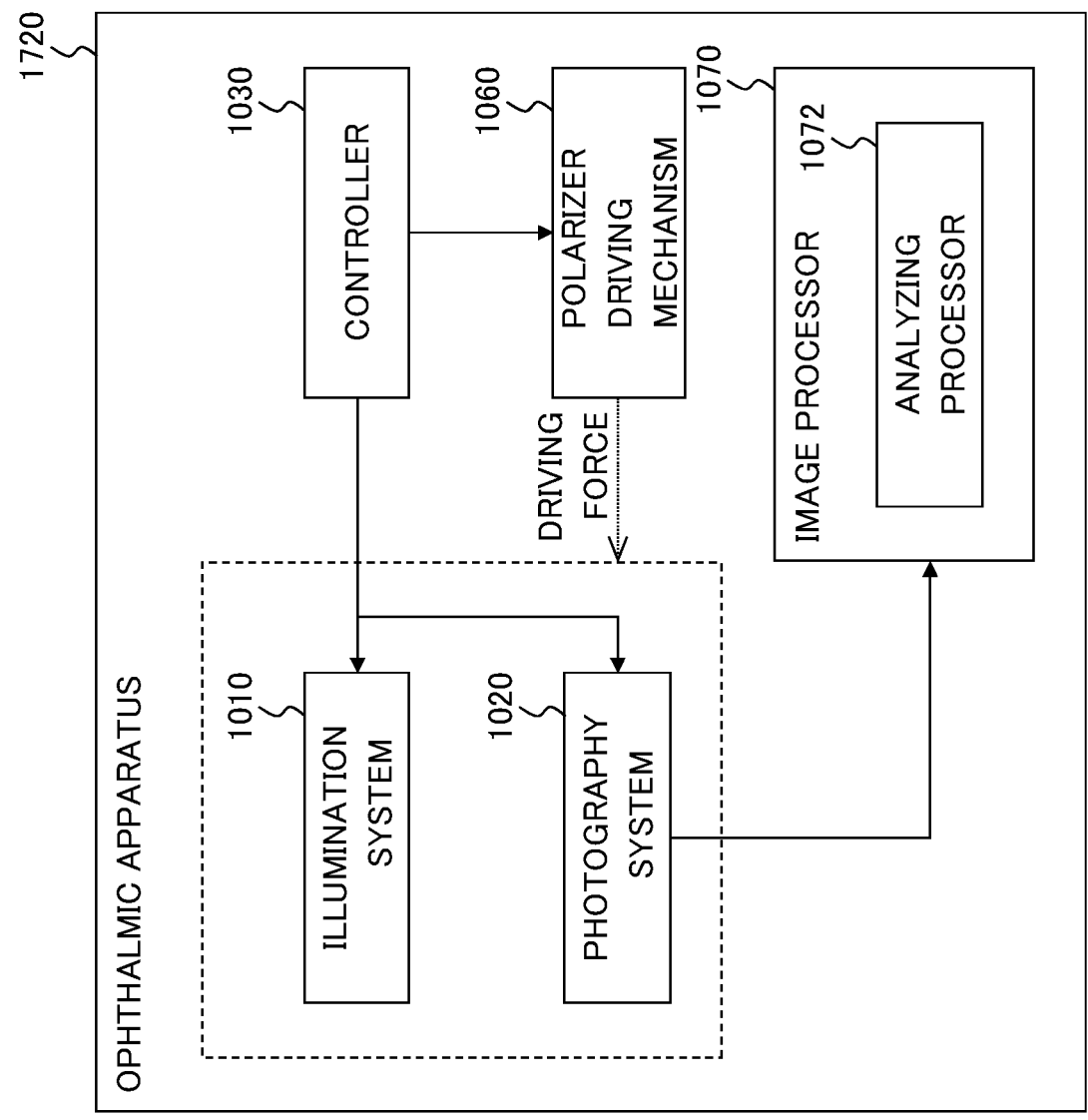
FIG. 20 is a diagram illustrating a configuration of an ophthalmic apparatus according to an aspect example of an embodiment.

FIG. 20 shows another example of the image processor 1070. The image processor 1070 of the ophthalmic apparatus 1720 of the present example includes the analyzing processor 1072.

The analyzing processor 1072 is configured to apply predetermined analysis processing to an image of the subject's eye E generated by the ophthalmic apparatus 1720. The analyzing processor 1072 includes hardware elements such as a processor and a storage device. The storage device retains a computer program such as an analysis program. One or more of the functions of the analyzing processor 1072 are implemented by cooperation of software such as the analysis program and hardware such as the processor.

Figure 21:
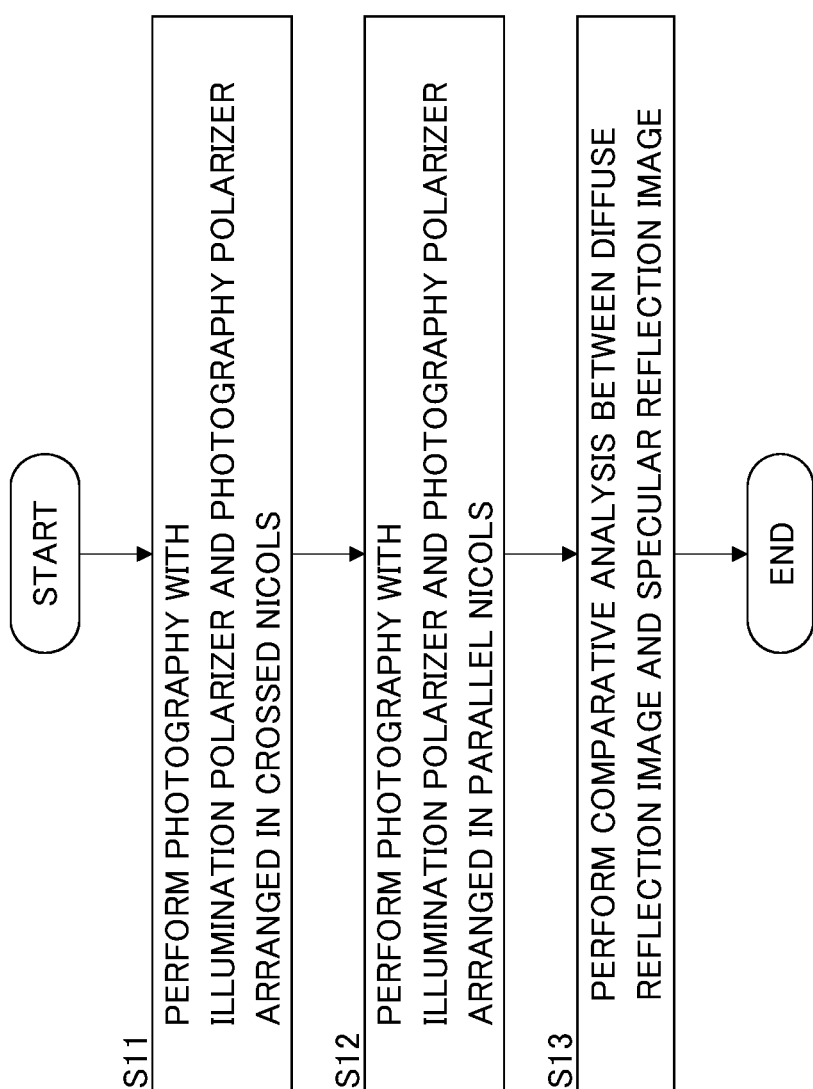
FIG. 21 is a flowchart illustrating processing executed by an ophthalmic apparatus according to an aspect example of an embodiment.

One example of the operation performed by the ophthalmic apparatus 1720 will be described with further reference to FIG. 21. In the present example, the analyzing processor 1072 is configured to perform a comparative analysis between a diffuse reflection image and a specular reflection image.

To begin with, the controller 1030 performs control of the polarizer driving mechanism 1060 thereby arranging the illumination polarizer 1012 and the photography polarizer 1021 in a state of crossed nicols. The illumination system 1010 and the photography system 1020 perform photography of the subject's eye E in this state of crossed nicols (S11). This photography generates a diffuse reflection image of the subject's eye E.

Further, the controller 1030 performs control of the polarizer driving mechanism 1060 thereby arranging the illumination polarizer 1012 and the photography polarizer 1021 in a state of parallel nicols. The illumination system 1010 and the photography system 1020 perform photography of the subject's eye E in this state of parallel nicols (S12). This photography generates a specular reflection image of the subject's eye E.

Figure 18:
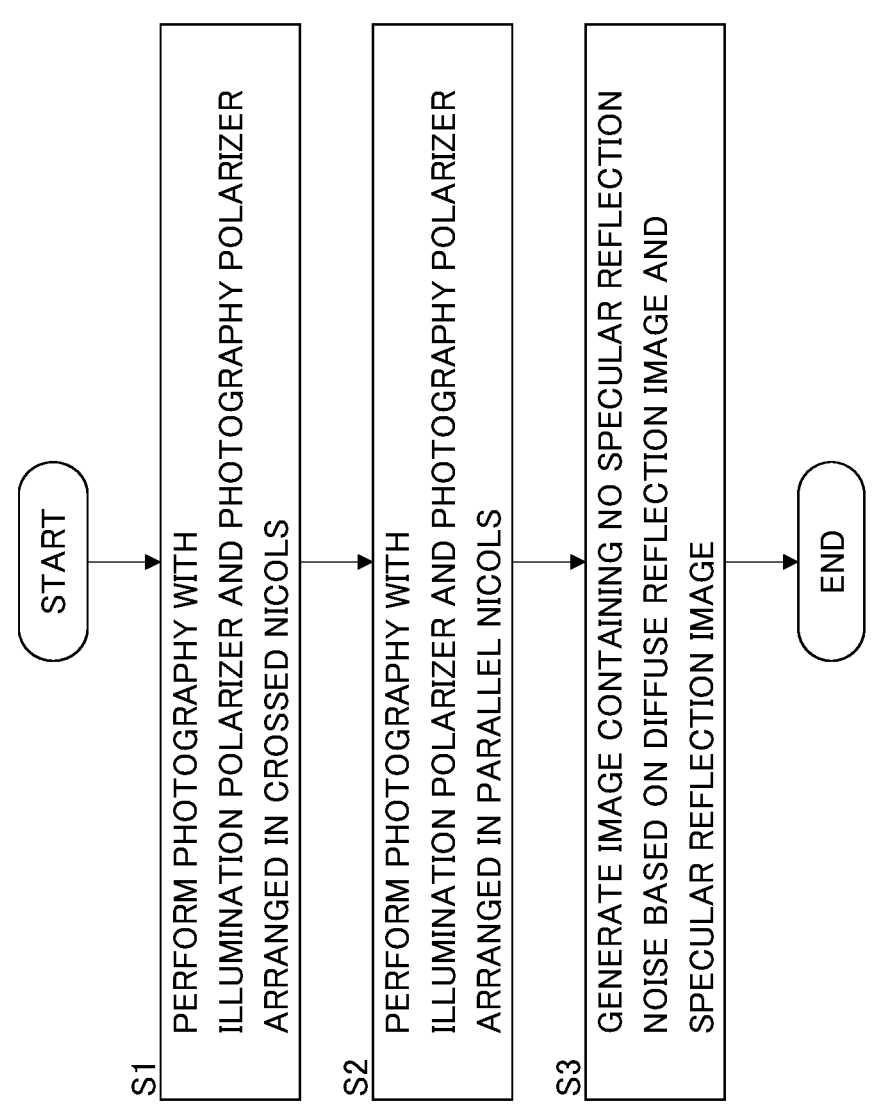
FIG. 18 is a flowchart illustrating processing executed by an ophthalmic apparatus according to an aspect example of an embodiment.

As in the case of the operation shown in FIG. 18, the step of acquiring a diffuse reflection image may be performed after the step of acquiring a specular reflection image. Alternatively, the step of acquiring a specular reflection image and the step of acquiring a diffuse reflection image may be performed simultaneously.

Furthermore, the analyzing processor 1072 executes a comparative analysis between the diffuse reflection image acquired in the step S11 and the specular reflection image acquired in the step S12 (S13). The comparative analysis performed in the step S13 may include any types or kinds of processing. Below, a description of an examination of floating objects (or floaters) that are present in an eye will be given as an example of a comparative analysis.

Examples of the types or kinds of intraocular floaters include floaters in the anterior chamber such as inflammatory cells (anterior chamber cells) and proteins (anterior chamber flare), and floaters in the vitreous body such as vitreous fibers and detached retinal cells. Since intraocular floaters move, it is considered to be desirable to reduce blurring of images of floaters by using intermittent illumination light as shown in FIG. 6B. However, continuous illumination light such as that shown in FIG. 6A may also be used.

In addition, photography of intraocular floaters uses illumination light having a relatively large amount of light in consideration of the small sizes of the floaters and the small light reflection from the floaters. Thus, specular reflection noise is highly likely to occur, and adverse effects of the specular reflection noise are relatively large. Therefore, the present aspect, which takes into account both a specular reflection image and a diffuse reflection image, is considered to be highly useful and effective.

Information generated by the analyzing processor 1072 in the present example may be any types or kinds of information relating to a freely selected type or kind of floaters that are present in the subject's eye E. Examples of this information include the identification of the type or kind of floaters (discrimination of floaters), the density of floaters, the number of floaters, the positions of floaters, the distribution of floaters, presence or absence of a specific disease, a state or condition of a specific disease, the duration of a specific disease, a state of the progress of a specific disease, and a state of the activity of a specific disease.

The analyzing processor 1072 of some examples may be configured to identify the type or kind of floaters on the basis of the intensity ratio between a specular reflection image and a diffuse reflection image. To do so, the analyzing processor 1072 first applies image segmentation to the specular reflection image to identify an image region(s) corresponding to floaters (floater region(s)), and also applies image segmentation to the diffuse reflection image to identify an image region(s) corresponding to floaters (floater region(s)).

Subsequently, the analyzing processor 1072 performs registration between the specular reflection image and the diffuse reflection image. From the result of this registration, the analyzing processor 1072 determines an association between the positions (coordinates) of one or more floater regions identified from the specular reflection image and the positions (coordinates) of one or more floater regions identified from the diffuse reflection image. As a result of this, an image region in the specular reflection image corresponding to a floater and an image region in the diffuse reflection image corresponding to the same floater, are identified and associated with each other.

Next, the analyzing processor 1072 calculates an intensity value of a floater region in the specular reflection image corresponding to a floater, and also calculates an intensity value of a floater region in the diffuse reflection image corresponding to the same floater. An intensity value is determined on the basis of a pixel value.

For example, an intensity value of a floater region may be a freely selected statistic calculated from pixel values in this floater region. This statistic may be, for example, the mean value, the variance, the standard deviation, the maximum value, the minimum value, the mode, the median, or the like.

Next, the analyzing processor 1072 compares the intensity value of a floater region in the specular reflection image corresponding to a floater (the first floater region) with the intensity value of a floater region in the diffuse reflection image corresponding to the same floater (the second floater region).

In some aspect examples, the analyzing processor 1072 calculates the ratio T1/T2 between the intensity T1 of the first floater region and the intensity T2 of the second floater region, and then compares the ratio T1/T2 with a predetermined threshold value TH. For example, the analyzing processor 1072 may be configured to infer that this floater is a macrophage if the absolute value of the ratio T1/T2 "abs(T1/T2)" is equal to or greater than the threshold value TH, and infer that this floater is a lymphocyte if the absolute value of the ratio T1/T2 "abs(T1/T2)" is less than the threshold value TH.

In the case of obtaining the density of floaters, the analyzing processor 1072 of some examples executes a process of setting an image region of a predetermined size or dimensions (e.g., an image region of 1 mm square), and a process of counting the number of floaters included in this image region.

Here, the size of the image region (e.g., the size in real space, such as "1 mm") may be defined on the basis of, for example, the design specification of the optical system of the ophthalmic apparatus 1720 and is typically defined to be the correspondence between a pixel (image element) and a size in real space (e.g., dot pitch). Here, the design specification of the optical system of the ophthalmic apparatus 1720 may include, for example, design data of the optical system and/or actual measurement data of the optical system.

Information on the density of floaters obtained in this way can be used, for example, for the evaluation (classification) of uveitis.

The number of floaters, the positions of floaters, and the distribution of floaters may be obtained in the same manner as the density of floaters. In addition, information on a specific disease targeted may be obtained by using a known evaluation method for this specific disease as in the evaluation of uveitis, for example.

According to the present aspect, it becomes possible to utilize polarization to conduct medical evaluations relating to floaters in an eye.

Note that a method of identifying floaters on the basis of the evaluation of reflection wavelength characteristics using optical coherence tomography (OCT) is known. However, to the best of the applicant's knowledge, it is not publicly known, and further there have not been any literature suggesting it, to conduct evaluation of intraocular floaters by combining polarization technology or technique with an illumination system and a photography system that satisfy the Scheimpflug condition as in the present aspect. Here, the method for identifying floaters on the basis of the evaluation of reflection wavelength characteristics using OCT is disclosed in the following paper: RUOBING QIAN, RYAN P. MCNABB, KEVIN C. ZHOU, HAZEM M. MOUSA, DANIEL R. SABAN, VICTOR L. PEREZ, ANTHONY N. KUO, AND JOSEPH A. IZATT, "In vivo quantitative analysis of anterior chamber white blood cell mixture composition using spectroscopic optical coherence tomography", Vol. 12, No. 4/1 Apr. 2021/Biomedical Optics Express, pp. 2134-2148.

Figure 22:
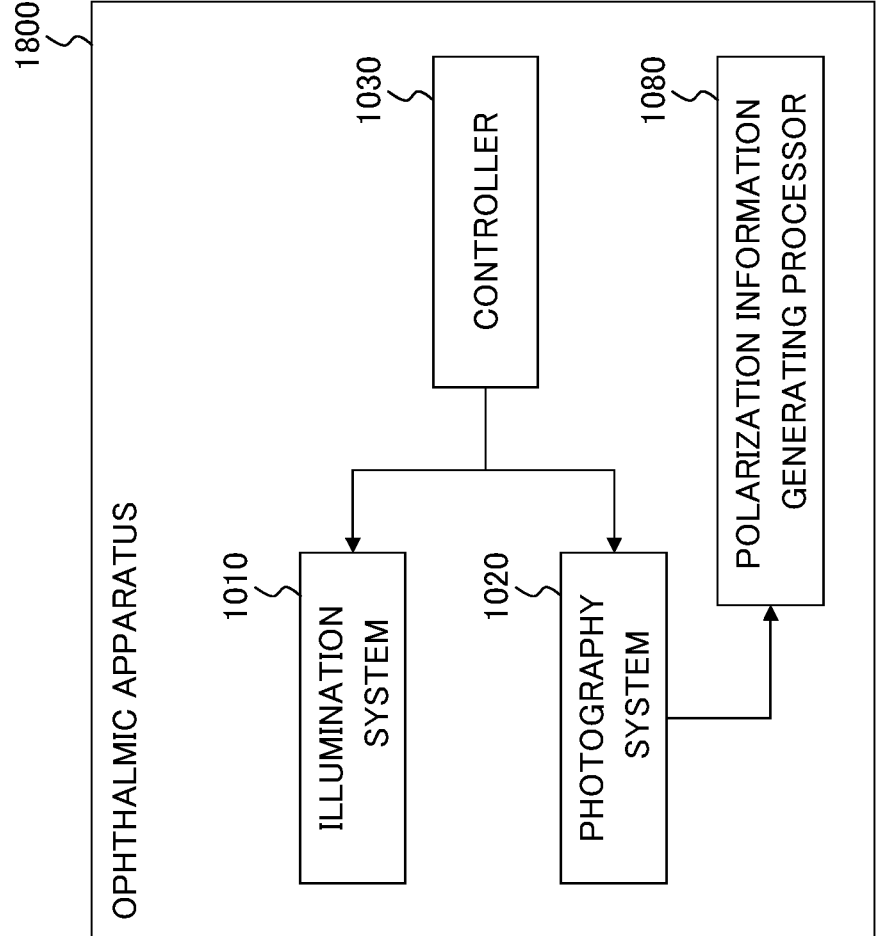
FIG. 22 is a diagram illustrating a configuration of an ophthalmic apparatus according to an aspect example of an embodiment.

FIG. 22 shows a configuration of an ophthalmic apparatus according to one aspect of the embodiment. The ophthalmic apparatus 1800 according to the present aspect includes the polarization information generating processor 1080, in addition to the illumination system 1010, the photography system 1020, and the controller 1030 which have the same or similar configurations as or to the corresponding components of the ophthalmic apparatus 1000.

The polarization information generating processor 1080 is configured to generate polarization information that represents a polarization state of return light from the subject's eye E to which illumination light is projected by the illumination system 1010, on the basis of an image generated by the photography system 1020.

More specifically, in the present aspect, as shown in FIG. 2 described above, the illumination system 1010 outputs slit illumination light by using the light source unit 1011, extracts an illumination polarization component from the slit illumination light by using the illumination polarizer 1012, and projects the extracted illumination polarization component onto the subject's eye E.

Furthermore, the photography system 1020 extracts a photography polarization component of return light from the subject's eye E with the illumination polarization component projected, by using the photography polarizer 1021, and detects the extracted photography polarization component by using the image sensor 1022.

In addition, the polarization information generating processor 1080 generates polarization information that represents a polarization state of the return light from the subject's eye E, based on the photography polarization component detected by the photography system 1022. The polarization information is information that represents a polarization characteristic of the subject's eye E.

The polarization information generating processor 1080 includes hardware elements such as a processor and a storage device. The storage device retains a computer program such as a polarization information generating program. One or more of the functions of the polarization information generating processor 1080 are implemented by cooperation of software such as the polarization information generating program and hardware such as the processor.

The type or kind of polarization information generated by the polarization information generating processor 1080 may be freely determined. For example, the type or kind of polarization information may be a value of a freely selected type or kind of polarization parameter, such as the Stokes parameters (Stokes vector), degree of polarization, degree of circular polarization, degree of elliptical polarization, surface normal, retardation, average intensity, intensity in each polarization direction, or the like.

Figure 23:
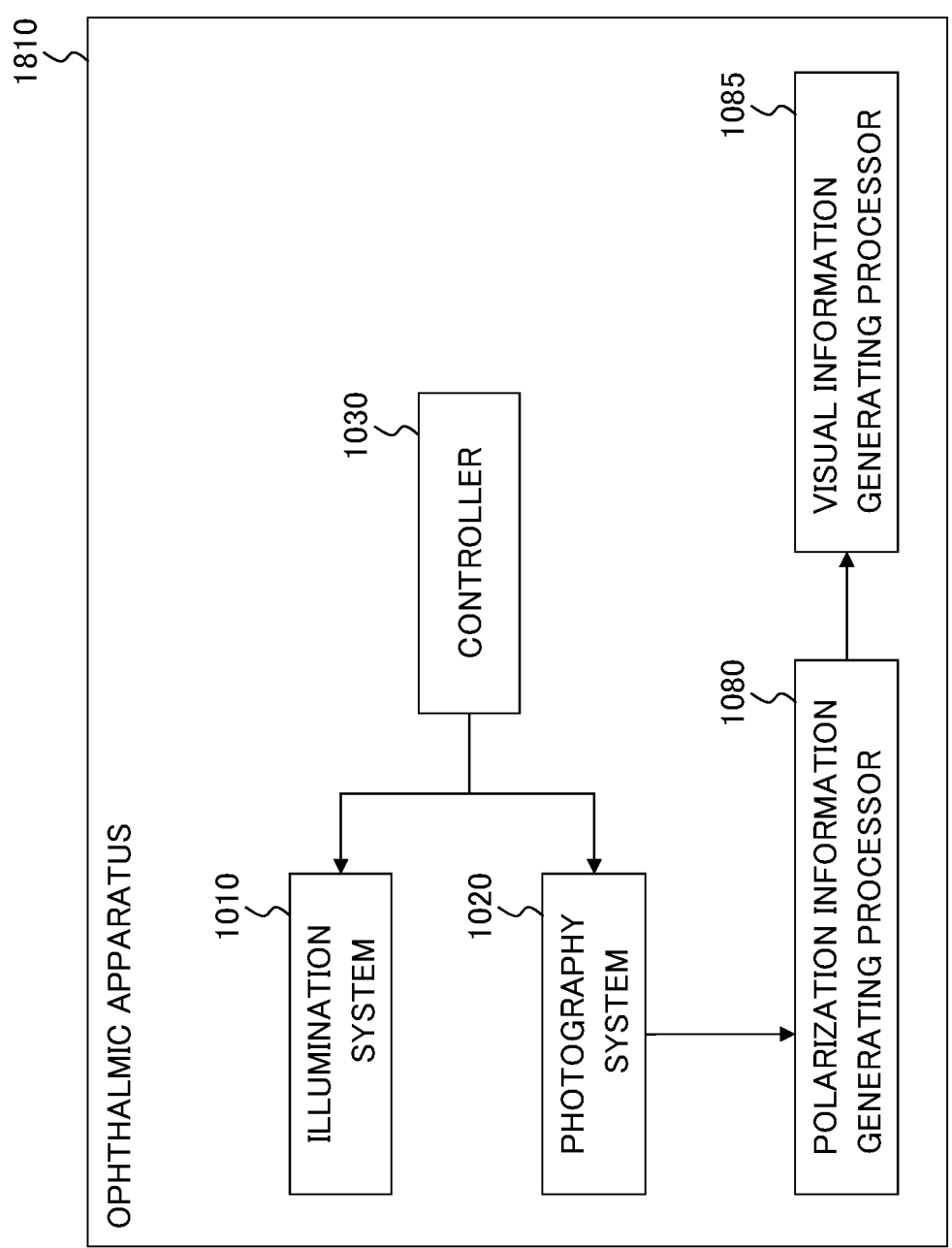
FIG. 23 is a diagram illustrating a configuration of an ophthalmic apparatus according to an aspect example of an embodiment.

FIG. 23 shows a configuration of an ophthalmic apparatus according to one aspect of the embodiment. The ophthalmic apparatus 1810 according to the present aspect includes the visual information generating processor 1085, in addition to the illumination system 1010, the photography system 1020, the controller 1030, and the polarization information generating processor 1080 which have the same or similar configurations as or to the corresponding components of the ophthalmic apparatus 1800.

The visual information generating processor 1085 is configured to generate visual information based on polarization information generated by the polarization information generating processor 1080. Visual information is information that is perceived using vision. In other words, visual information is a representation that stimulate vision (visual representation, visualization). Examples of visual information include images, charts, maps, tables, lists, and so forth. For example, the visual information generating processor 1085 generates visual information on the basis of a value of a polarization parameter determined by the polarization information generating processor 1080.

Examples of visual information include the following visual representations: a visual representation showing a characteristic area (an area that is characteristic in terms of a specific polarization parameter) of a Scheimpflug image, such as a highlighting representation of an area of an engrafted part (fixed part, surviving part) of a graft (doner tissue) in an eye after corneal transplantation; a visual representation showing an area of a Scheimpflug image that is presumed to be a lesion, such as a highlighting representation of a possible lesion of a cornea; a visual representation showing a distribution of values of a polarization parameter, such as a color map showing a state of a flow of filtering blebs; and a visual representation showing a result of evaluation conducted on the basis of a value of a polarization parameter, such as a color map showing the severity of a specific disease.

Figure 24:
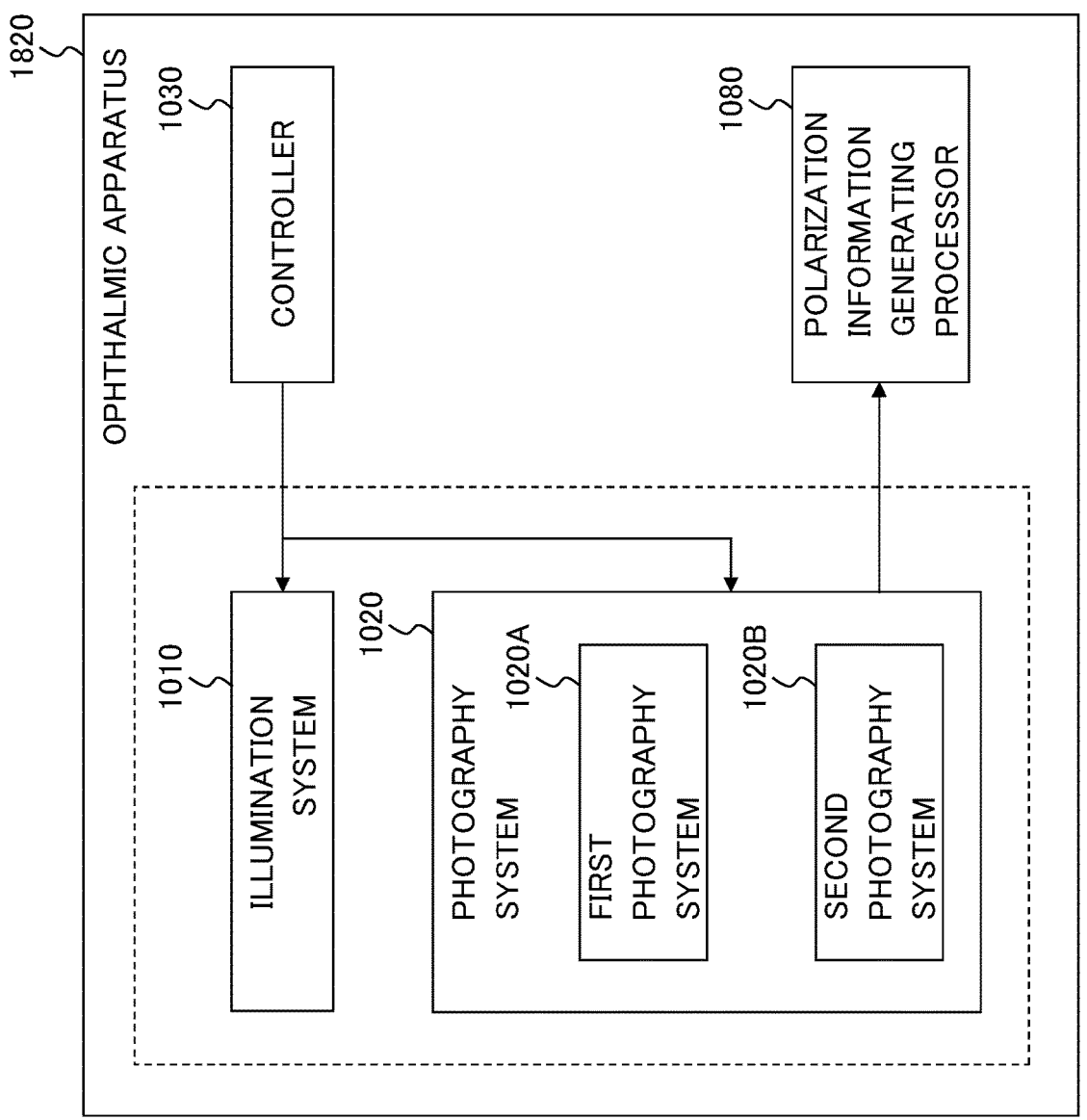
FIG. 24 is a diagram illustrating a configuration of an ophthalmic apparatus according to an aspect example of an embodiment.

FIG. 24 shows a configuration of an ophthalmic apparatus according to one aspect of the embodiment. The ophthalmic apparatus 1820 according to the present aspect includes the illumination system 1010, the photography system 1020, and the controller 1030, and the polarization information generating processor 1080 which have the same or similar configurations as or to the corresponding components of the ophthalmic apparatus 1800.

The photography system 1020 of the ophthalmic apparatus 1820 includes the first photography system 1020A and the second photography system 1020B that have the same or similar configurations as or to the photography system 1020 of the ophthalmic apparatus 1500 shown in FIG. 12. In the present aspect as well, the illumination system 1010 and the first photography system 1020A are configured to satisfy the Scheimpflug condition, and the illumination system 1010 and the second photography system 1020B are configured to satisfy the Scheimpflug condition.

Further, as in the configuration shown in FIG. 13, the photography polarizer 1021 of the present aspect includes the first photography polarizer 1021A provided in the first photography system 1020A and the second photography polarizer 1021B provided in the second photography system 1020B.

In addition, the image sensor 1022 of the present aspect includes the first image sensor 1022A provided in the first photography system 1020A and the second image sensor 1022B provided in the second photography system 1020B.

The polarization information generating processor 1080 of the present aspect may generate polarization information, based on the first photography polarization component and the second photography polarization component. Here, the first photography polarization component is extracted by the first photography polarizer 1021A from the first return light from the subject's eye E and then detected by the first image sensor 1022A. Similarly, the second photography polarization component is extracted by the second photography polarizer 1021B from the second return light from the subject's eye E and then detected by the second image sensor 1022B.

According to the ophthalmic apparatus 1820 of the present aspect, the operation for generating polarization information can be carried out using two or more pieces of photography systems. This makes it possible to provide an improvement in the efficiency of the process of generating polarization information.

The polarizer driving mechanism 1060 may be combined with the ophthalmic apparatus 1820 of the present aspect. With this combination, the resulting ophthalmic apparatus 1820 can produce a relative change between the polarization direction of the first photography polarization component and the polarization direction of the second photography polarization component. Here, the first photography polarization component is a polarization component extracted by the first photography polarizer 1021A from the first return light from the subject's eye E. Similarly, the second photography polarization component is a polarization component extracted by the second photography polarizer 1021B from the second return light from the subject's eye E. By being able to produce this relative change, the resulting ophthalmic apparatus 1820 can perform generation of polarization information efficiently and under various conditions.

Figure 25:
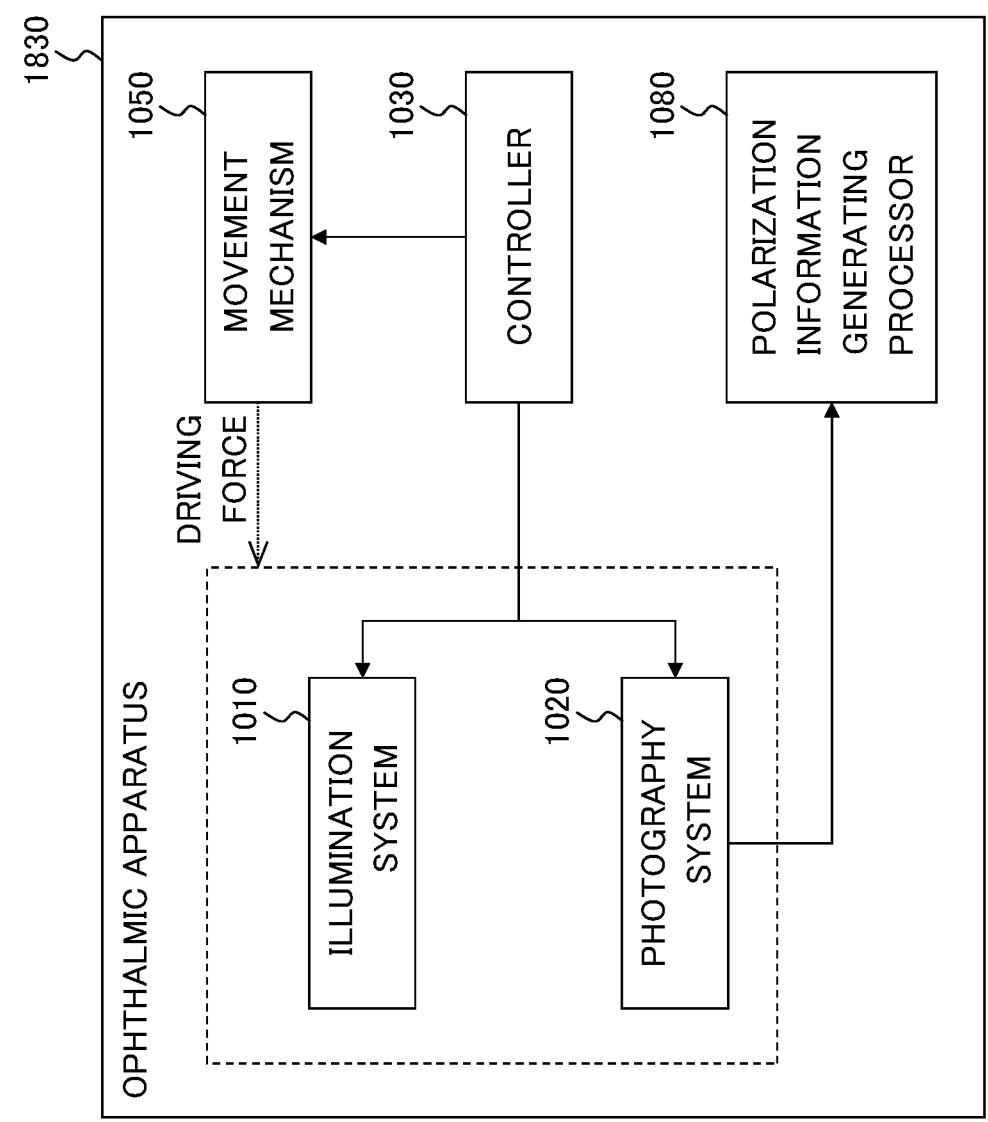
FIG. 25 is a diagram illustrating a configuration of an ophthalmic apparatus according to an aspect example of an embodiment.

FIG. 25 shows a configuration of an ophthalmic apparatus according to one aspect of the embodiment. The ophthalmic apparatus 1830 according to the present aspect includes the movement mechanism 1050, in addition to the illumination system 1010, the photography system 1020, the controller 1030, and the polarization information generating processor 1080 which have the same or similar configurations as or to the corresponding components of the ophthalmic apparatus 1800.

The movement mechanism 1050 of the ophthalmic apparatus 1830 is configured to move the illumination system 1010 and the photography system 1020 in the same or similar manner as or to the movement mechanism 1050 of the ophthalmic apparatus 1200 of FIG. 15. The movement mechanism 1050 operates under control executed by the controller 1030. With this configuration, the ophthalmic apparatus 1830 of some examples can apply scanning, such as any of those shown in FIG. 6A to 7B, to a three dimensional region of the subject's eye E, thereby collecting a series of Scheimpflug images.

The polarization information generating processor 1080 of the present aspect may generate polarization information based on a Scheimpflug image group collected from a three dimensional region of the subject's eye. Here, the polarization information generating processor 1080 may be configured to generate polarization information directly from the Scheimpflug image group collected from the three dimensional region of the subject's eye. Alternatively, the polarization information generating processor 1080 may be configured to generate polarization information from data obtained by processing the Scheimpflug image group collected from the three dimensional region of the subject's eye. For example, the polarization information generating processor 1080 may be configured to generate polarization information on the basis of a three dimensional image constructed from the Scheimpflug image group and/or a rendered image of this three dimensional image.

According to the present aspect, the ophthalmic apparatus 1830 can generate polarization information based on a series of Scheimpflug images collected by scanning the subject's eye E using the illumination system 1010 and the photography system 1020 that satisfy the Scheimpflug condition. Therefore, the ophthalmic apparatus 1830 can acquire polarization information for a three dimensional region of the subject's eye E. As a result, the ophthalmic apparatus 1830 can obtain a three dimensional distribution of a polarization characteristic of the subject's eye E, and conduct three dimensional evaluation of the subject's eye E.

Figure 26:
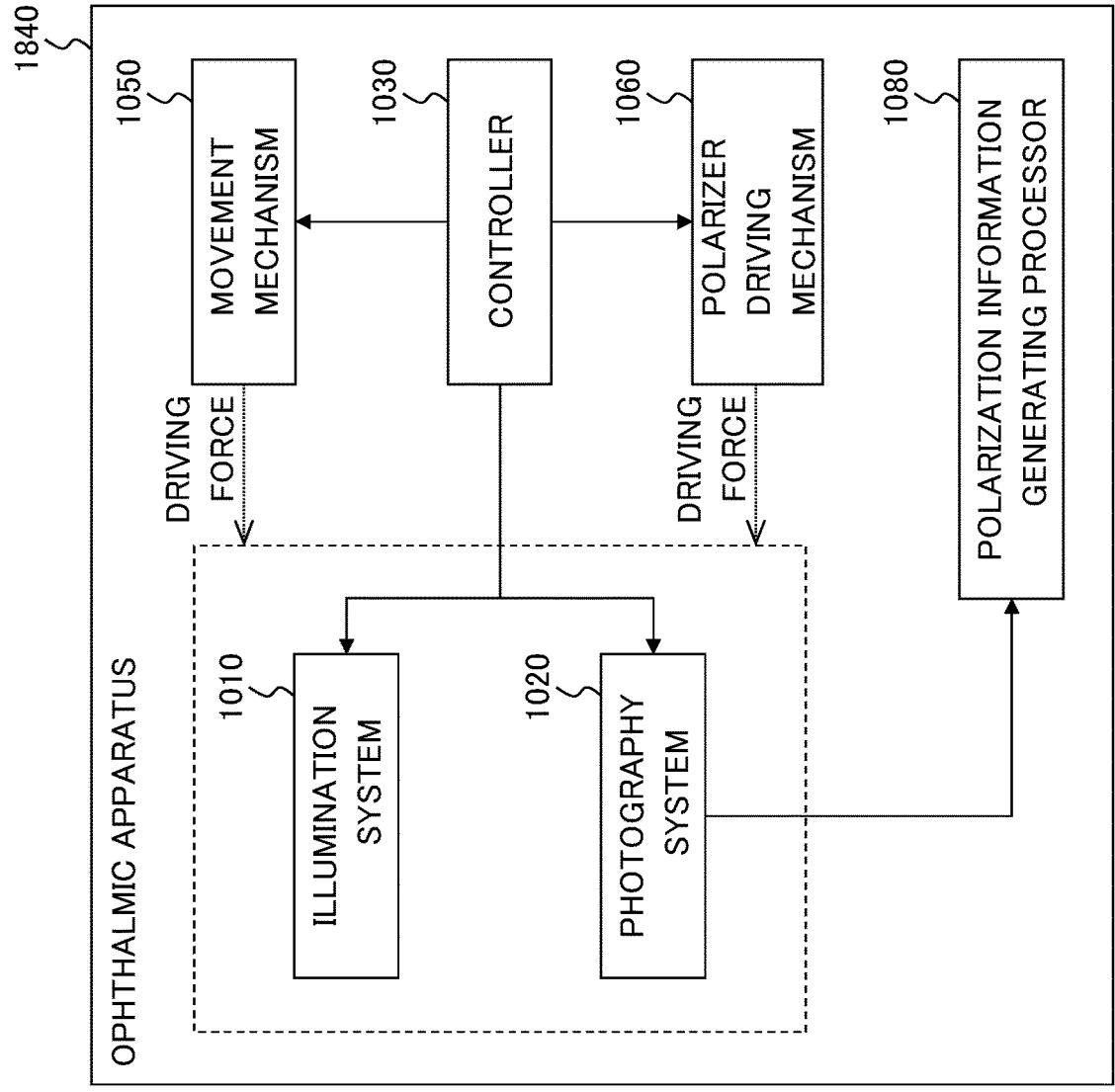
FIG. 26 is a diagram illustrating a configuration of an ophthalmic apparatus according to an aspect example of an embodiment.

FIG. 26 shows a configuration of an ophthalmic apparatus according to one aspect of the embodiment. The ophthalmic apparatus 1840 according to the present aspect includes the movement mechanism 1050 and the polarizer driving mechanism 1060, in addition to the illumination system 1010, the photography system 1020, the controller 1030, and the polarization information generating processor 1080 which have the same or similar configurations as or to the corresponding components of the ophthalmic apparatus 1800.

The movement mechanism 1050 of the ophthalmic apparatus 1840 is configured to move the illumination system 1010 and the photography system 1020 in the same or similar way as or to the movement mechanism 1050 of the ophthalmic apparatus 1200 of FIG. 5. The controller 1030 performs control of the movement mechanism 1050. With this configuration, the ophthalmic apparatus 1840 of some examples can apply scanning, such as any of those shown in FIG. 6A to 7B, to a three dimensional region of the subject's eye E thereby collecting a series of Scheimpflug images.

The polarizer driving mechanism 1060 of the ophthalmic apparatus 1840 is configured to perform driving of the illumination polarizer 1012 and/or driving of the photography polarizer 1021 in the same or similar way as or to the polarizer driving mechanism 1060 of the ophthalmic apparatus 1300 of FIG. 8. Here, the driving of the illumination polarizer 1012 is for changing the polarization direction of an illumination polarization component extracted from slit illumination light, and the driving of the photography polarizer 1021 is for changing the polarization direction of a photography polarization component extracted from return light from the subject's eye E. The controller 1030 performs control of the polarizer driving mechanism 1060.

With this configuration, the ophthalmic apparatus 1840 can produce a relative change between the polarization direction of the illumination polarization component extracted from the slit illumination light and the polarization direction of the photography polarization component extracted from the return light from the subject's eye E.

Figure 27A:
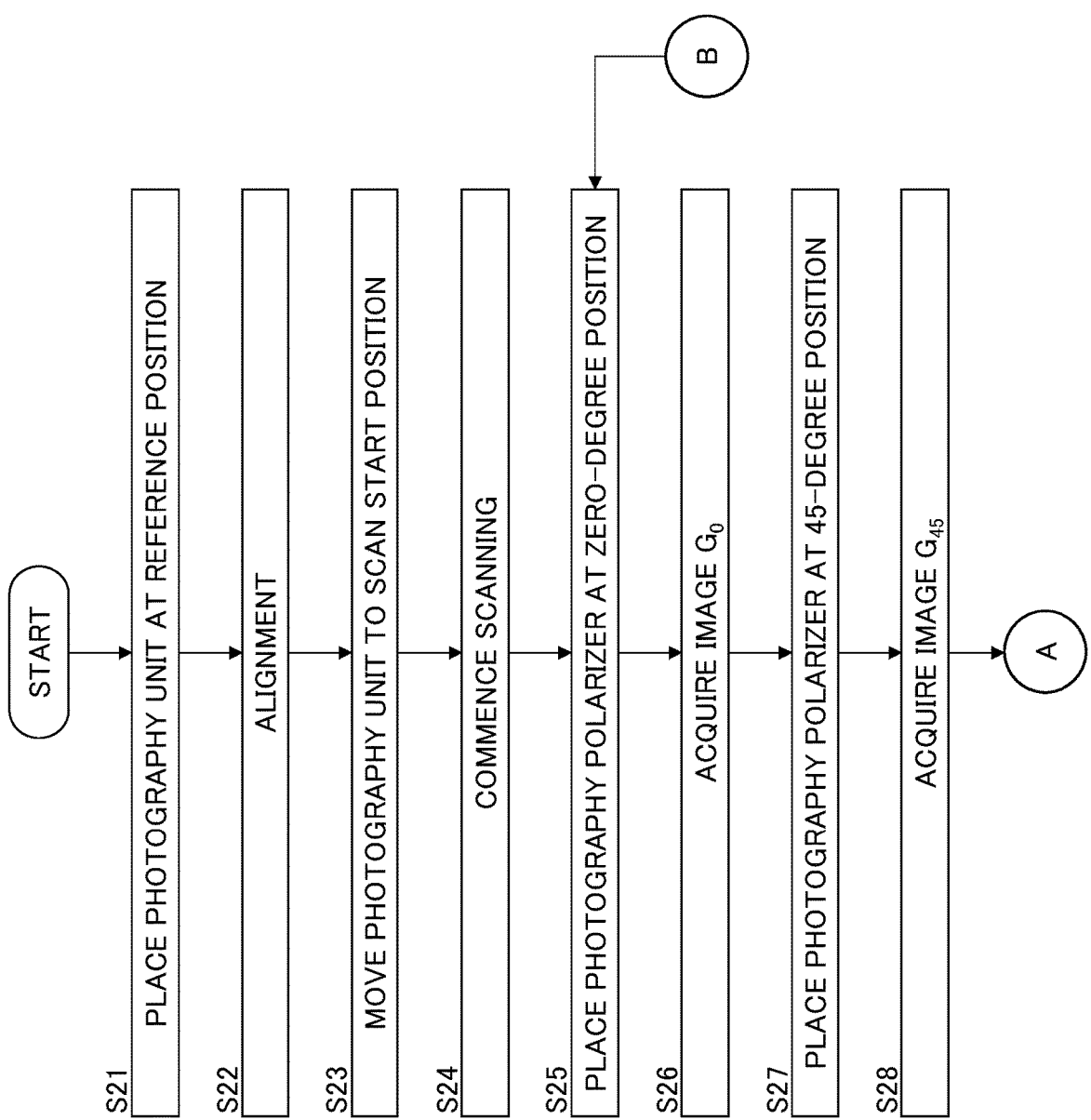
FIG. 27A is a flowchart illustrating processing executed by an ophthalmic apparatus according to an aspect example of an embodiment.
Figure 27B:
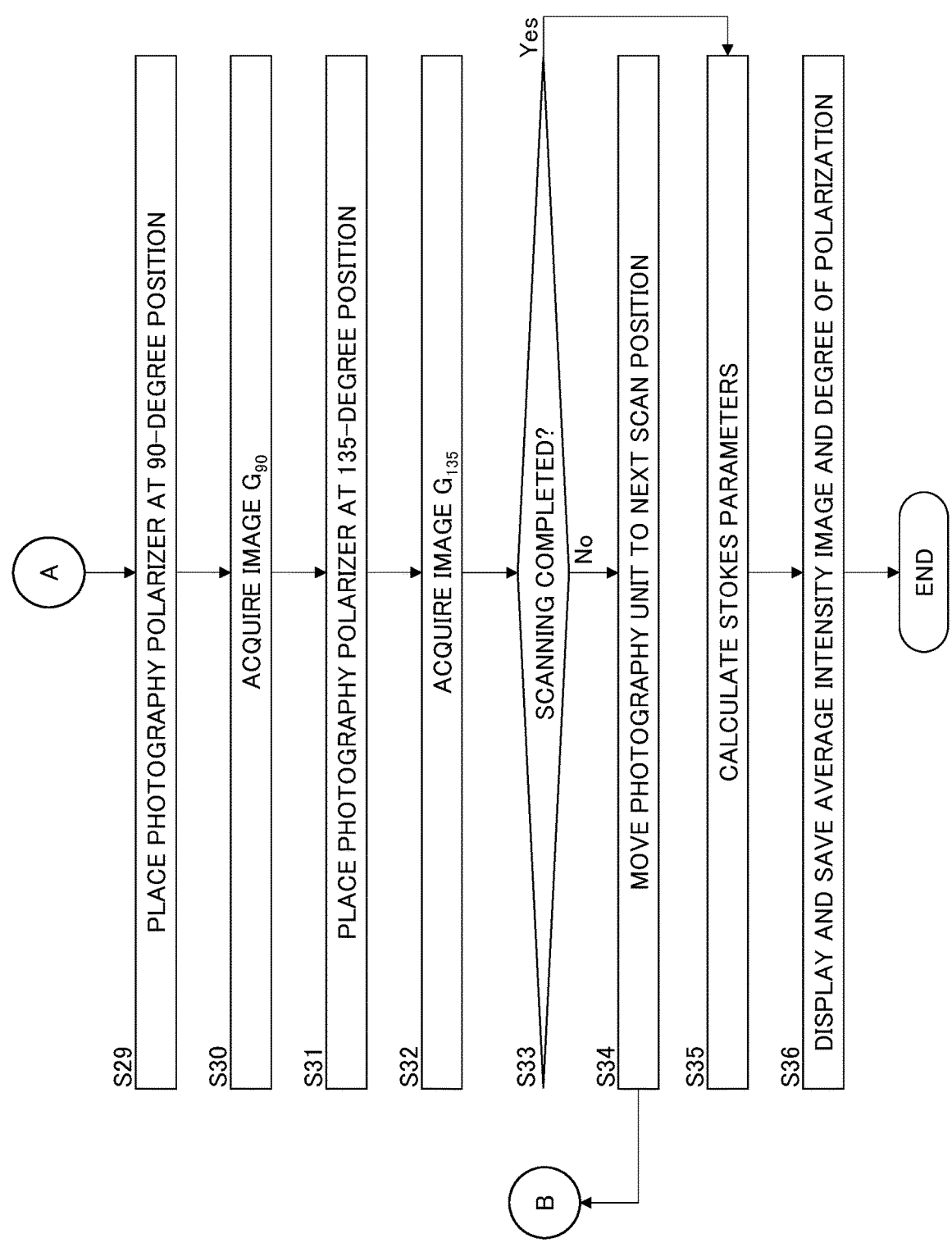
FIG. 27B is a flowchart illustrating processing executed by an ophthalmic apparatus according to an aspect example of an embodiment.

FIG. 27 shows one example of the operation of the ophthalmic apparatus 1840 of the present aspect. The present example is one example of the operation for obtaining the Stokes parameters as the polarization information.

Note that in the present example, the illumination polarizer 1012 is fixed and only the photography polarizer 1021 is driven. In other words, in the present example, while the polarization direction of an illumination polarization component projected onto the subject's eye E is constant (unchanged), the polarization direction of a photography polarization component extracted from return light from the subject's eye E is variable. In another operation example, the photography polarizer 1021 is fixed and only the illumination polarizer 1012 is driven. In yet another operation example, both the illumination polarizer 1012 and the photography polarizer 1021 are driven.

To begin with, the photography unit (the illumination system 1010 and the photography system 1020) are placed at a reference position (S21). The reference position is, for example, a position directly in front of the subject's eye E. More specifically, the reference position is not only the neutral position in the body axis direction of the subject (the Y direction, longitudinal direction, vertical direction), but also the neutral position in the left-right direction (the X direction, lateral direction, horizontal direction) perpendicular to both the body axis direction and the axial direction of the subject's eye E (the Z direction, depth direction). The operation of moving the photography unit to the reference position is performed automatically and/or manually.

Next, alignment of the optical system (the illumination system 1010 and the photography system 1020) with respect to the subject's eye E is performed (S22). The alignment is performed automatically and/or manually. Further, preparatory operations other than the alignment may also be performed.

Next, the photography unit is moved to the scan start position (S23). The operation of moving of the photography unit to the scan start position is performed automatically and/or manually.

Once the photography unit is placed at the scan start position, the ophthalmic apparatus 1840 commences scanning of the subject's eye E (S24). The controller 1030 begins the scanning in response to a predetermined event. This event may be, for example, an instruction from the user or completion of the step S22.

Upon commencement of the scanning, the controller 1030 performs control of the polarizer driving mechanism 1060 (the photography polarizer driving mechanism 1062) to place the photography polarizer 1021 at the zero-degree position (S25). The zero-degree position corresponds to a state of the photography polarizer 1021 in which the angle formed by the polarization direction of the illumination polarization component and the polarization direction of the photography polarization component is zero degrees, that is, a state in which these polarization directions are parallel to each other. In other words, the zero-degree position corresponds to an arrangement state of the photography polarizer 1021 in which the transmission axis direction of the illumination polarizer 1012 and the transmission axis direction of the photography polarizer 1021 match, that is, a state in which these transmission axes are arranged in parallel to each other.

Next, the controller 1030 performs control of the illumination system 1010 and the photography system 1020 to conduct photography of the subject's eye E. As a result, an image $G_0$ corresponding to the zero-degree position is obtained (S26). The image $G_0$ acquired by this step is stored in a storage device that is not shown in the drawings.

Next, the controller 1030 performs control of the polarizer driving mechanism 1060 (the photography polarizer driving mechanism 1062) to place the photography polarizer 1021 at the 45-degree position (S27). The 45-degree position corresponds to a state of the photography polarizer 1021 in which the angle formed by the polarization direction of the illumination polarization component and the polarization direction of the photography polarization component is 45 degrees.

Next, the controller 1030 performs control of the illumination system 1010 and the photography system 1020 to conduct photography of the subject's eye E. As a result, an image $G_{45}$ corresponding to the 45-degree position is obtained (S28). The image $G_{45}$ acquired by this step is stored in a storage device that is not shown in the drawings.

Next, the controller 1030 performs control of the polarizer driving mechanism 1060 (the photography polarizer driving mechanism 1062) to place the photography polarizer 1021 at the 90-degree position (S29). The 90-degree position corresponds to a state of the photography polarizer 1021 in which the angle formed by the polarization direction of the illumination polarization component and the polarization direction of the photography polarization component is 90 degrees.

Next, the controller 1030 performs control of the illumination system 1010 and the photography system 1020 to conduct photography of the subject's eye E. As a result, an image $G_{90}$ corresponding to the 90-degree position is obtained (S30). The image $G_{90}$ acquired by this step is stored in a storage device that is not shown in the drawings.

Next, the controller 1030 performs control of the polarizer driving mechanism 1060 (the photography polarizer driving mechanism 1062) to place the photography polarizer 1021 at the 135-degree position (S31). The 135-degree position corresponds to a state of the photography polarizer 1021 in which the angle formed by the polarization direction of the illumination polarization component and the polarization direction of the photography polarization component is 135 degrees.

Next, the controller 1030 performs control of the illumination system 1010 and the photography system 1020 to conduct photography of the subject's eye E. As a result, an image $G_{135}$ corresponding to the 135-degree position is obtained (S32). The image $G_{135}$ acquired by this step is stored in a storage device that is not shown in the drawings.

This completes the photographing operation at the scan start position. The controller 1030 determines whether or not the scanning has completed (S33).

For example, the scanning is determined to be completed when a photographing operation at the scan end position is completed. A predetermined number of scan positions are set between the scan start position and the scan end position. For example, in the case where the distance from the scan start position to the scan end position is 10 mm and the number of scan positions is 100, the intervals between these scan positions (the distance between two adjacent scan positions) is 0.1 mm. The intervals between scan positions (scan interval) may not be constant. A plurality of scan positions is ordered in accordance with the arrangement (or sequence) of the scan positions.

Let N be the number of scan positions at each of which photography is conducted, and the N number of scan positions are denoted by $P_1$ to $P_N$. Four images acquired at the n-th scan position $P_n$ are denoted by $G_0(P_n)$, $G_{45}(P_n)$, $G_{90}(P_n)$, and $G_{135}(P_n)$.

If the scanning has not yet completed (S33: No), the controller 1030 performs control of the movement mechanism 1050 to move the photography unit to the next scan position (S34).

The movement of the photography unit may be continuous movement as shown in FIG. 6A or intermittent movement as shown in FIG. 6B. In the case where the photography unit is moved continuously, the series of processes in the steps S25 to S32 are executed at high speed. As a result, the four acquired images $G_0$, $G_{45}$, $G_{90}$, and $G_{135}$ depict substantially the same location (the same part, the same region, the same area) of the subject's eye E and are associated with the same scan position (the n-th scan position $P_n$).

It should be noted that in the case where the photography unit is moved continuously, the process in the step S34 corresponds to an operation of shifting to photography at the next scan position. On the other hand, in the case where the photography unit is moved intermittently, the process in the step S34 corresponds to an operation of moving the photography unit by a distance equal to the scan interval described above.

The series of processes in the steps S25 to S34 are repeated until the controller 1030 determines in the step S33 that the scanning has completed (S33: Yes). With this repetition, the four images $G_0(P_n)$, $G_{45}(P_n)$, $G_{90}(P_n)$, and $G_{135}(P_n)$ are acquired for each of the N number of scan positions (for each n-th scan position $P_n$).

Next, the polarization information generating processor 1080 calculates the Stokes parameters ($S_0$, $S_1$, $S_2$, $S_3$) on the basis of the image $G_0$ acquired in the step S26, the image $G_{45}$ acquired in the step S28, the image $G_{90}$ acquired in the step S30, and the image $G_{135}$ acquired in the step S32 (S35). The method of calculating the Stokes parameters ($S_0$, $S_1$, $S_2$, $S_3$) is well known. The Stokes parameters ($S_0$, $S_1$, $S_2$, $S_3$) are calculated for each pixel position.

In addition, the polarization information generating processor 1080 obtains an average intensity image and a degree of polarization from the Stokes parameters ($S_0$, $S_1$, $S_2$, $S_3$) calculated in the step S35. The controller 1030 displays the average intensity image and the degree of polarization on a display device that is not shown in the drawings. Further, the controller 1030 saves the average intensity image and the degree of polarization in a storage device that is not shown in the drawings (S36).

The average intensity for generating the average intensity image is calculated by the following formula: $\sqrt{[(S_0^2+S_1^2)/2]}$. Further, the degree of polarization is calculated by the following formula: $\sqrt{[(S_1^2+S_2^2+S_3^2)/S_0]}$. The average intensity and the degree of polarization are calculated for each pixel position.

Figure 28A:
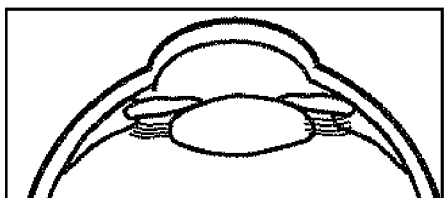
FIG. 28A shows an example of an image generated by processing executed by an ophthalmic apparatus according to an aspect example of an embodiment.
Figure 28B:
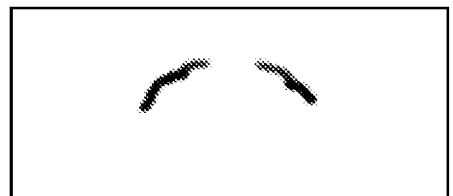
FIG. 28B shows an example of an image generated by processing executed by an ophthalmic apparatus according to an aspect example of an embodiment.

An intensity image as shown in FIG. 28A is constructed based on the average intensity calculated for each pixel position. Similarly, a polarization degree image as shown in FIG. 28B is constructed based on the degree of polarization calculated for each pixel position. The polarization degree image of FIG. 28B is an image obtained from the subject's eye E after corneal transplantation. A part of the corneal graft that has not settled (has not been engrafted) has a high degree of polarization and is therefore emphasized (highlighted) in the polarization degree image.

Information obtained from the Stokes parameters ($S_0$, $S_1$, $S_2$, $S_3$) calculated in the step S36 is not limited to an average intensity image and a degree of polarization, and may be any types or kinds of information.

In the case where the number of the photography systems 1020 provided in the ophthalmic apparatus 1840 is one, photography is sequentially performed four times in the steps S26, S28, S30 and S32. On the other hand, in the case where the number of the photography systems 1020 provided in the ophthalmic apparatus 1840 is two, the photography in the step S26 and the photography in the step S28 may be performed simultaneously, and the photography in the step S30 and the photography in the step S32 may be performed simultaneously, for example.

Figure 29A:
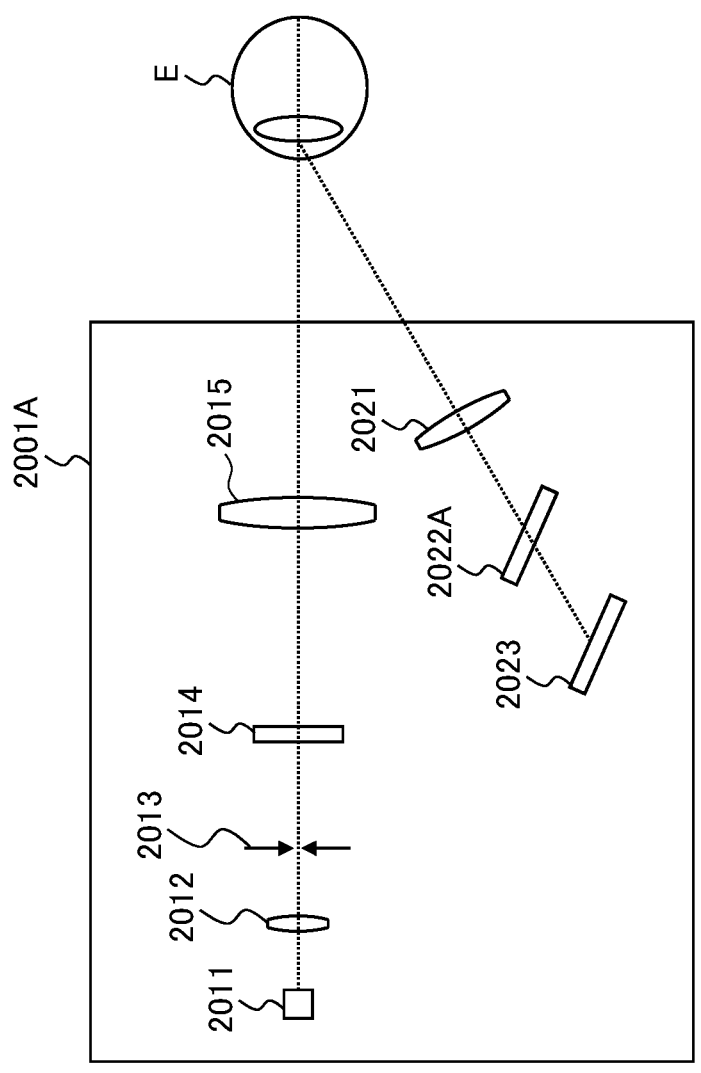
FIG. 29A is a diagram illustrating a configuration of an ophthalmic apparatus according to an aspect example of an embodiment.

In some aspect examples of the embodiment, the photography polarizer may include a polarizing plate that is arranged in an oblique manner with respect to the optical axis of the photography system. The photography unit 2001A shown in FIG. 29A is a modification of the photography unit 2001 of FIG. 11. In the photography unit 2001 of FIG. 11, the polarizing plate 2022 of the photography system is arranged to be perpendicular to the optical axis of the photography system (photography optical axis). On the other hand, in the photography unit 2001A, the polarizing plate 2022A of the photography system is arranged to be parallel to the light receiving surface of the image sensor 2023. Note that since the illumination system and the photography system of the photography unit 2001A are configured to satisfy the Scheimpflug condition, the light receiving surface of the image sensor 2023 is arranged in an oblique manner with respect to the photography optical axis.

Figure 29B:
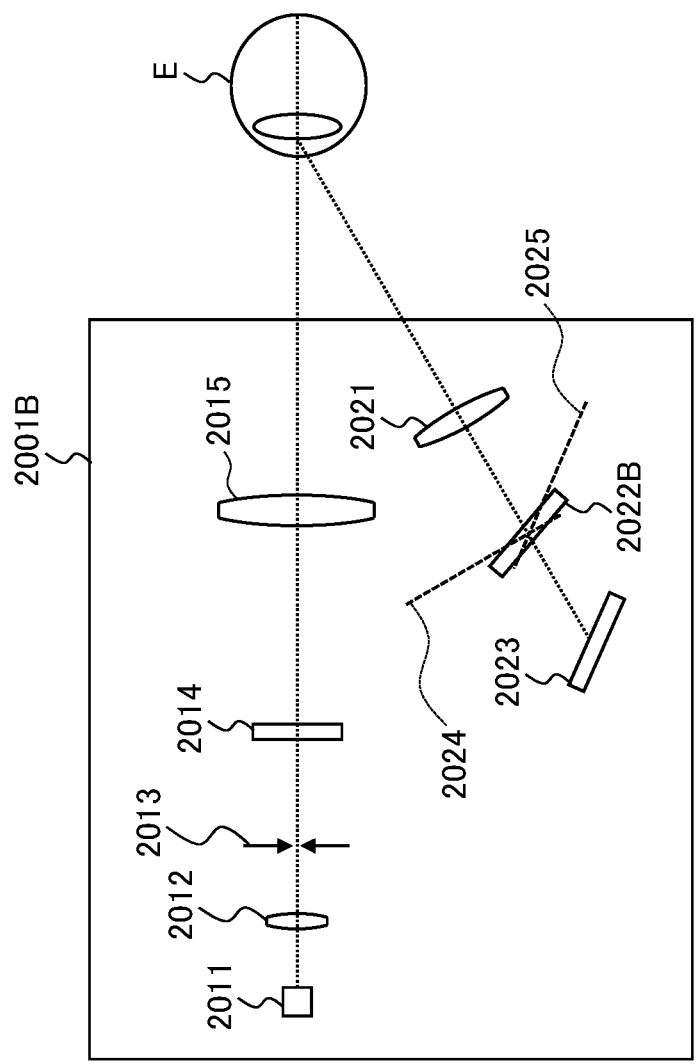
FIG. 29B is a diagram illustrating a configuration of an ophthalmic apparatus according to an aspect example of an embodiment.

Another example is shown in FIG. 29B. The photography unit 2001B shown in FIG. 29B is a modification of the photography unit 2001 of FIG. 11. The reference character 2024 in FIG. 29B denotes a direction perpendicular to the photography optical axis, and the reference character 2025 denotes a direction parallel to the light receiving surface of the image sensor 2023. In the photography unit 2001B, the polarizing plate 2022B of the photography system is oriented and placed in a direction between the direction 2024 perpendicular to the photography optical axis (the first direction) and the direction 2025 parallel to the light receiving surface of the image sensor 2023 (the second direction).

An ophthalmic apparatus of some aspect examples may include a mechanism for changing the orientation of the polarizing plate provided in the photography system. This makes it possible to arrange the polarizing plate in a desired or appropriate orientation.

Figure 30:
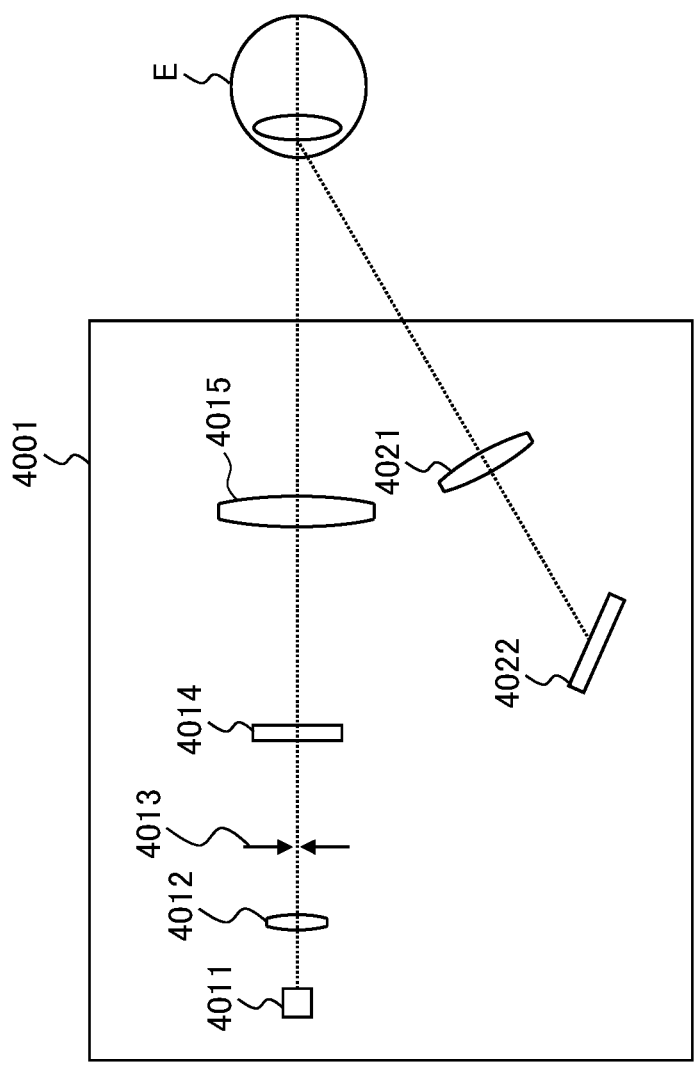
FIG. 30 is a diagram illustrating a configuration of an ophthalmic apparatus according to an aspect example of an embodiment.

FIG. 30 shows a configuration of an ophthalmic apparatus according to one aspect of the embodiment. The photography unit 4001 of the ophthalmic apparatus according to the present aspect includes an illumination system and a photography system. The illumination system and the photography system are configured to satisfy the Scheimpflug condition.

The illumination system includes the light source 4011, the collimator lens 4012, the slit forming mechanism 4013, the polarizing plate 4014, and the objective lens 4015. The light source 4011 is configured to emit light, the collimator lens 4012 is configured to convert the light emitted from the light source 4011 into parallel light, the slit forming mechanism 4013 is configured to generate slit illumination light from the parallel light generated by the collimator lens 4012, the polarizing plate 4014 is configured to extract an illumination polarization component from the slit illumination light generated by the slit forming mechanism 4013, and the objective lens 4015 is configured to project the illumination polarization component that has passed through the polarizing plate 4014 (parallel light) onto the subject's eye E. Note that the illumination system may include elements other than these.

The photography system includes the objective lens 4021 and the polarization camera 4022. The objective lens 4021 is configured to convert return light from the subject's eye E with illumination light (illumination polarization component) projected, into converging light. The polarization camera 4022 is configured to detect the converging return light generated by the objective lens 4021. Note that the photography system may include elements other than these. The polarization camera 4022 includes a polarizer array corresponding to a photography polarizer, and a photodiode array corresponding to an image sensor. In a standard polarization camera 4022, a lens array, a polarizer array (phase plate array), and a photodiode array are positioned and arranged on a pixel-by-pixel basis.

Figure 31:
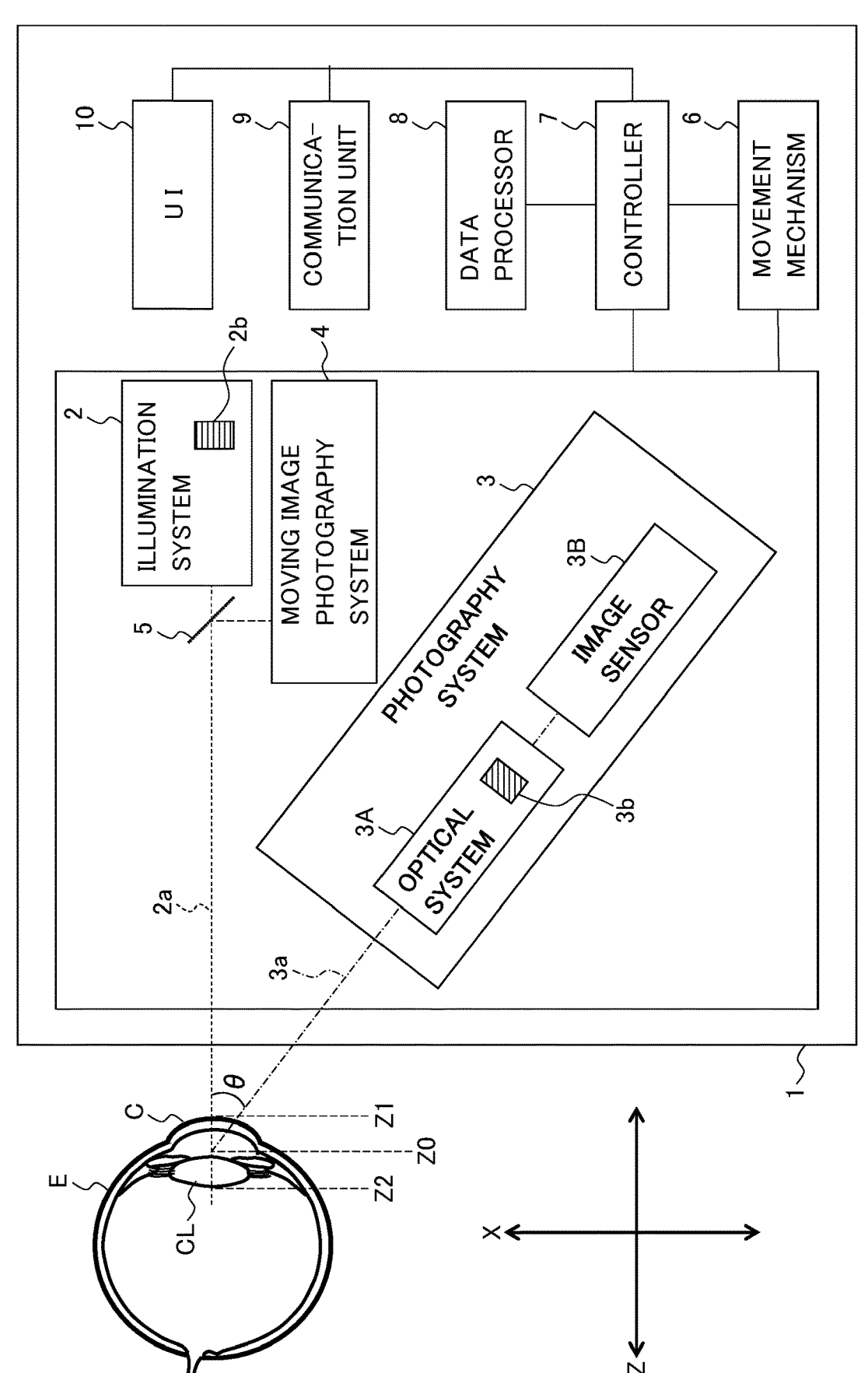
FIG. 31 is a diagram illustrating a configuration of an ophthalmic apparatus according to an aspect example of an embodiment.

FIG. 31 shows one example of a specific configuration of an ophthalmic apparatus that can function as the various aspect examples described above. FIG. 31 is a top view.

The direction along the axis of the subject's eye E is defined to be the Z direction. Of the directions perpendicular to the Z direction, the left-right direction (or, the lateral direction, the horizontal direction) for the subject is defined to be the X direction. The direction perpendicular to both the X direction and the Z direction (the longitudinal direction, the vertical direction, the body axis direction) is defined to be the Y direction.

The ophthalmic apparatus of the present example is a slit lamp microscope system 1 that has a similar configuration as that disclosed in Patent Document 3 (Japanese Unexamined Patent Application Publication No. 2019-213733 (International Publication No. WO 2019/240149)). The slit lamp microscope system 1 includes the illumination system 2, the photography system 3, the moving image photography system 4, the optical path coupling element 5, the movement mechanism 6, the controller 7, the data processor 8, the communication unit 9 and the user interface 10.

The reference character C denotes the cornea of the subject's eye E, and the reference character CL denotes the crystalline lens of the subject's eye E. The anterior chamber is a region between the cornea C and the crystalline lens CL (the region between the cornea C and the iris).

For details of each element of the slit lamp microscope system 1, see Patent Document 3 (Japanese Unexamined Patent Application Publication No. 2019-213733 (International Publication No. WO 2019/240149)).

The illumination system 2 is configured to project illumination light onto the anterior segment of the subject's eye E. The reference character 2a denotes the optical axis of the illumination system 2 that is referred to as the illumination optical axis. The illumination system 2 includes the illumination polarizer 2b. Furthermore, the illumination system 2 includes a light source unit, which is not shown in the drawings, and other elements.

The photography system 3 is configured to perform photography of the anterior segment onto which the illumination light from the illumination system 2 is being projected. The reference character 3a denotes the optical axis of the photography system 3 that is referred to as the photography optical axis. The optical system 3A is configured to guide return light from the anterior segment of the subject's eye E with the slit light projected, to the image sensor 3B. The optical system 3A includes the photography polarizer 3b and other elements. The image sensor 3B includes a light detecting plane that receives the light guided by the optical system 3A. The image sensor 3B includes an area sensor that has a two dimensional image detecting area. The area sensor may be, for example, a charge-coupled device (CCD) area sensor, a complementary metal oxide semiconductor (CMOS) area sensor, or another type or kind of area sensor.

The illumination system 2 and the photography system 3 function as a Scheimpflug camera. More specifically, the illumination system 2 and the photography system 3 are configured in such a manner that the subject plane along the illumination optical axis 2a, the optical system 3A, and the light detecting plane of the image sensor 3B satisfy the Scheimpflug condition, that is, in such a manner that the YZ plane passing through the illumination optical axis 2a (the YZ plane contains the subject plane), the principal plane of the optical system 3A, and the light detecting plane of the image sensor 3B all intersect on the same straight line.

With this configuration, the illumination system 2 and the photography system 3 may conduct photography, for example, in a state where at least the area from the posterior surface of the cornea C to the anterior surface of the crystalline lens CL, which is referred to as the anterior chamber, is in focus. Further, the illumination system 2 and the photography system 3 may conduct photography, for example, in a state where at least the area from the vertex of the anterior surface of the cornea C (Z=Z1) to the vertex of the posterior surface of the crystalline lens CL (Z=Z2) is in focus. Note that the coordinate Z=Z0 corresponds to the intersection of the illumination optical axis 2a and the photography optical axis 3a.

The moving image photography system 4 is a video camera that performs moving image photography of the anterior segment of the subject's eye E in parallel with the photography of the subject's eye E performed by the illumination system 2 and the photography system 3. The optical path coupling element 5 couples the optical path of the illumination system 2 and the optical path of the moving image photography system 4. The optical path of the illumination system 2 is referred to as the illumination optical path, and the optical path of the moving image photography system 4 is referred to as the moving image photography optical path.

Figure 32:
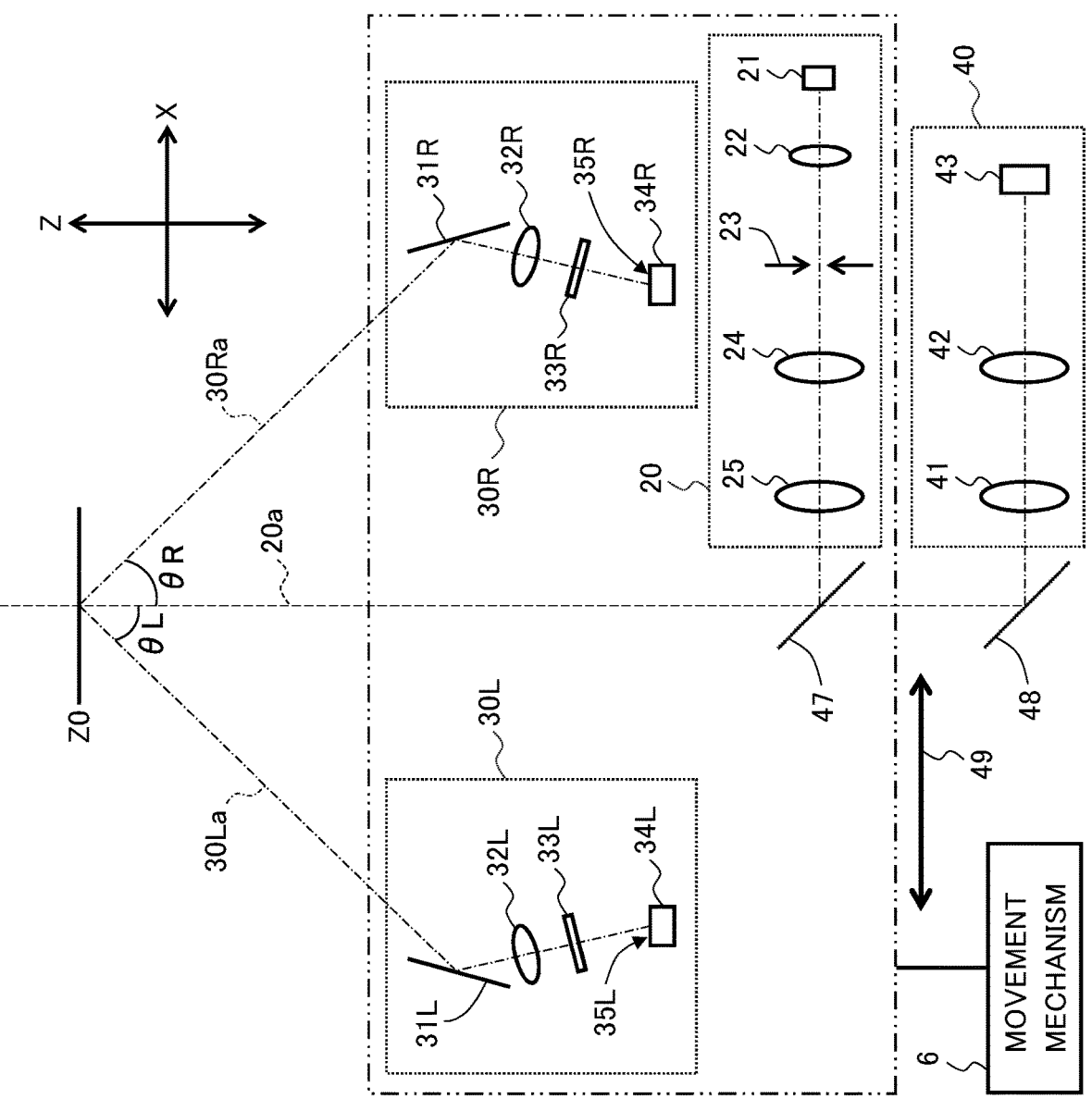
FIG. 32 is a diagram illustrating a configuration of an ophthalmic apparatus according to an aspect example of an embodiment.

FIG. 32 shows a specific example of an optical system that includes the illumination system 2, the photography system 3, the moving photography system 4, and the optical path coupling element 5. The optical system shown in FIG. 32 includes the illumination system 20, the left photography system 30L, the right photography system 30R, the moving image photography system 40, and the beam splitter 47. The illumination system 20 is an example of the illumination system 2, the left photography system 30L and the right photography system 30R are examples of the photography system 3, the moving image photography system 40 is an example of the moving image photography system 4, and the beam splitter 47 is an example of the optical path coupling element 5. The optical system shown in FIG. 32 is one example of a configuration that includes two photography systems like the ophthalmic apparatus 1500 in FIG. 15.

The reference character 20a denotes the optical axis of the illumination system 20 (referred to as the illumination optical axis), the reference character 30La denotes the optical axis of the left photography system 30L (referred to as the left photography optical axis), and the reference character 30Ra denotes the optical axis of the right photography system 30R (referred to as the right photography optical axis). The angle θL represents the angle formed by the illumination optical axis 20a and the left photography optical axis 30La, and the angle 8R represents the angle formed by the illumination optical axis 20a and the right photography optical axis 30Ra. The coordinate Z=Z0 corresponds to the intersection of the illumination optical axis 20a, the left photography optical axis 30La, and the right photography optical axis 30Ra.

The movement mechanism 6 moves the illumination system 20, the left photography system 30L, and the right photography system 30R in the directions denoted by the arrow 49 (the X direction).

The illumination light source 21 of the illumination system 20 outputs illumination light (e.g., visible light), and the positive lens 22 refracts the illumination light. The slit forming part 23 forms a slit to allow part of the illumination light to pass through the slit. The slit light generated in this way is refracted by the group of objective lenses 24 and 25, reflected by the beam splitter 47, and projected onto the anterior segment of the subject's eye E.

The reflector 31L and the imaging lens 32L of the left photography system 30L direct, to the photography polarizer 33L, light coming from the anterior segment onto which the slit light is being projected by the illumination system 20 (i.e., light coming from the anterior segment and traveling in the direction of the left photography system 30L). The light that has passed through the photography polarizer 33L, which corresponds to a photography polarization component, is detected by the image sensor 34L. The image sensor 34L receives the photography polarization component by the light detecting plane 35L.

The left photography system 30L performs repetitive photography in parallel with movement of the illumination system 20, the left photography system 30L, and the right photography system 30R performed by the movement mechanism 6. With this, a plurality of anterior segment images (i.e., a series of Scheimpflug images) is acquired.

The subject plane along the illumination optical axis 20*a*, the optical system that includes the reflector 31L and the imaging lens 32L, and the light detecting plane 35L satisfy the Scheimpflug condition. The right photography system 30R has the same configuration and function as those of the left photography system 30L.

The Scheimpflug image collection conducted by the left photography system 30L and the Scheimpflug image collection conducted by the right photography system 30R are performed in parallel with each other.

The controller 7 may be configured to execute synchronization between the repetitive photography carried out by the left photography system 30L and the repetitive photography carried out by the right photography system 30R. This synchronization can provide a correspondence (relationship) between the series of Scheimpflug images obtained by the left photography system 30L and the series of Scheimpflug images obtained by the right photography system 30R.

Note that the controller 7 or the data processor 8 may be configured to execute a process of determining a correspondence between the plurality of anterior segment images obtained by the left photography system 30L and the plurality of anterior segment images obtained by the right photography system 30R.

The moving image photography system 40 acquires a moving image of the anterior segment of the subject's eye E from a fixed position in parallel with the photography performed by the left photography system 30L and the photography performed by the right photography system 30R. The light transmitted through the beam splitter 47 is reflected by the reflector 48 and enters the moving image photography system 40. The light that has entered the moving image photography system 40 is refracted by the objective lens 41 and then forms an image on the light detecting plane of the image sensor 43 by the imaging lens 42. The image sensor 43 may be an area sensor. The moving image photography system 40 may be used for monitoring of the movement of the subject's eye E, alignment, tracking, and other operations. The moving image photography system 40 may also be used for processing collected Scheimpflug images.

Returning to the reference of FIG. 31, the movement mechanism 6 is configured to move the illumination system 2 and the photography system 3 in an integrated manner in the X direction.

The controller 7 is configured to perform control of each part of the slit lamp microscope system 1. The controller 7 can execute control of the illumination system 2, the photography system 3, and the movement mechanism 6, and control of the moving image photography system 4 in parallel with each other. As a result of this parallel control, acquisition (collection) of a series of Scheimpflug images and moving image photography (acquisition (collection) of a series of time series images) can be conducted in parallel with each other.

Further, the controller 7 can execute control of the illumination system 2, the photography system 3, and the movement mechanism 6, and control of the moving image photography system 4 in synchronization with each other. This synchronization control makes it possible to synchronize the acquisition (collection) of a series of Scheimpflug images and the moving image photography with each other.

In the case where the photography system 3 includes the left photography system 30L and the right photography system 30R, the controller 7 can execute synchronization control between repetitive photography performed by the left photography system 30L (acquisition (collection) of a series of Scheimpflug images) and repetitive photography performed by the right photography system 30R (acquisition (collection) of a series of Scheimpflug images).

The controller 7 includes a processor, a storage device, and the like. The storage device retains computer programs such as various kinds of control programs. One or more of the functions of the controller 7 are implemented by cooperation of software such as the control program and hardware such as the processor. The controller 7 executes control of the illumination system 2, the photography system 3, and the movement mechanism 6, in order to conduct scanning of a three dimensional region of the subject's eye E using the slit illumination light (using an illumination polarization component thereof). For details of this control, refer to Patent Document 3 (Japanese Unexamined Patent Application Publication No. 2019-213733 (International Publication No. WO 2019/240149)).

The data processor 8 executes various kinds of data processing. The data processor 8 includes a processor, a storage device, and the like. The storage device retains computer programs such as various kinds of data processing programs. One or more of the functions of the data processor 8 are implemented by cooperation of software such as the data processing program and hardware such as the processor. The data processor 8 may be configured to execute any kinds of data processing described in the above embodiments, such as the generation of an image containing no specular reflection noise, the comparative analysis between a diffuse reflection image and a specular reflection image, the generation of polarization information, and so forth.

The communication unit 9 performs data communication between the slit lamp microscope system 1 and one or more other apparatuses. The user interface 10 includes any types or kinds of user interface devices such as a display device and an operation device.

The slit lamp microscope system 1 shown in FIG. 31 and FIG. 32 is merely an example, and therefore the configurations of ophthalmic apparatuses according to embodiments as well as the configurations for implementing aspect examples of the embodiments are not limited to the slit lamp microscope system 1 of the present example.

Some non-limiting features of the ophthalmic apparatus according to the above non-limiting embodiment will be described below.

The first aspect example of the ophthalmic apparatus of the embodiment includes: an illumination system configured to project illumination light onto a subject's eye; and a photography system configured to perform photography of the subject's eye, wherein the illumination system and the photography system are configured to satisfy a Scheimpflug condition, the illumination system includes a light source unit configured to output slit illumination light and an illumination polarizer configured to extract an illumination polarization component from the slit illumination light output by the light source unit, and the illumination system is configured to project the illumination polarization component extracted by the illumination polarizer onto the subject's eye as the illumination light, and the photography system includes a photography polarizer configured to extract a photography polarization component from return light from the subject's eye with the slit illumination light projected and an image sensor configured to detect the photography polarization component extracted by the photography polarizer.

The second aspect example of the ophthalmic apparatus of the embodiment is the ophthalmic apparatus according to the first aspect example, further including a movement mechanism configured to move the illumination system and the photography system.

The third aspect example of the ophthalmic apparatus of the embodiment is the ophthalmic apparatus according to the second aspect example, further including a first controller configured to perform at least control of the photography system and control of the movement mechanism to cause the photography system to collect a series of images.

The fourth aspect example of the ophthalmic apparatus of the embodiment is the ophthalmic apparatus according to any of the first to third aspect examples, further including: an illumination polarizer moving mechanism configured to insert and remove the illumination polarizer into and from an optical path of the illumination system; and a photography polarizer moving mechanism configured to insert and remove the photography polarizer into and from an optical path of the photography system.

The fifth aspect example of the ophthalmic apparatus of the embodiment is the ophthalmic apparatus according to any of the first to fourth aspect examples, further including a polarizer driving mechanism configured to perform one of or both driving of the illumination polarizer for changing a polarization direction of the illumination polarization component and driving of the photography polarizer for changing a polarization direction of the photography polarization component.

The sixth aspect example of the ophthalmic apparatus of the embodiment is the ophthalmic apparatus according to the fifth aspect example, wherein the polarizer driving mechanism includes a first polarizer driving mechanism configured to perform one of or both the driving of the illumination polarizer and the driving of the photography polarizer to produce a relative change between the polarization direction of the illumination polarization component and the polarization direction of the photography polarization component.

The seventh aspect example of the ophthalmic apparatus of the embodiment is the ophthalmic apparatus according to the sixth aspect example, further including: a movement mechanism configured to move the illumination system and the photography system; and a first controller configured to perform at least control of the photography system and control of the movement mechanism to cause the photography system to collect a series of images.

The eighth aspect example of the ophthalmic apparatus of the embodiment is the ophthalmic apparatus according to the seventh aspect example, wherein the first controller is configured to control the movement mechanism to move the illumination system and the photography system in a predetermined movement direction, and the first polarizer driving mechanism is configured to perform one of or both the driving of the illumination polarizer and the driving of the photography polarizer such that the polarization direction of the illumination polarization component becomes perpendicular to the predetermined movement direction and the polarization direction of the photography polarization component becomes parallel to the predetermined movement direction.

The ninth aspect example of the ophthalmic apparatus of the embodiment is the ophthalmic apparatus according to any of the fifth to eighth aspect examples, wherein the photography system includes a first photography system and a second photography system, wherein the illumination system and the first photography system are configured to satisfy a Scheimpflug condition, the illumination system and the second photography system are configured to satisfy a Scheimpflug condition, the photography polarizer includes a first photography polarizer disposed in the first photography system and a second photography polarizer disposed in the second photography system, and the image sensor includes a first image sensor disposed in the first photography system and a second image sensor disposed in the second photography system.

The tenth aspect example of the ophthalmic apparatus of the embodiment is the ophthalmic apparatus according to the ninth aspect example, further including a second polarizer driving mechanism configured to perform one of or both the driving of the first photography polarizer and the driving of the second photography polarizer to produce a relative change between a polarization direction of a first photography polarization component and a polarization direction of a second photography polarization component, the first photography polarization component being extracted from first return light from the subject's eye by the first photography polarizer and the second photography polarization component being extracted from second return light from the subject's eye by the second photography polarizer.

The eleventh aspect example of the ophthalmic apparatus of the embodiment is the ophthalmic apparatus according to the tenth aspect example, further including: a movement mechanism configured to move the illumination system and the photography system; and a first controller configured to perform at least control of the photography system and control of the movement mechanism to cause the photography system to collect a series of images.

The twelfth aspect example of the ophthalmic apparatus of the embodiment is the ophthalmic apparatus according to the eleventh aspect example, wherein the first controller is configured to control the movement mechanism to move the illumination system and the photography system in a predetermined movement direction, the polarization direction of the illumination polarization component is oriented in a direction perpendicular to the predetermined movement direction, and the second polarizer driving mechanism is configured to perform one of or both the driving of the first photography polarizer and the driving of the second photography polarizer such that both the polarization direction of the first photography polarization component and the polarization direction of the second photography polarization component become parallel to the predetermined movement direction.

The thirteenth aspect example of the ophthalmic apparatus of the embodiment is the ophthalmic apparatus according to any of the fifth to twelfth aspect examples, further including a second controller configured to control the polarizer driving mechanism to produce a relative change between the polarization direction of the illumination polarization component and the polarization direction of the photography polarization component, wherein the photography system is configured to generate an image of the subject's eye corresponding to a predetermined combination of the polarization direction of the illumination polarization component and the polarization direction of the photography polarization component.

The fourteenth aspect example of the ophthalmic apparatus of the embodiment is the ophthalmic apparatus according to the thirteenth aspect example, wherein the second controller is configured to perform one of or both the driving of the illumination polarizer and the driving of the photography polarizer such that the polarization direction of the illumination polarization component and the polarization direction of the photography polarization component become perpendicular to each other, to cause the photography system to generate a diffuse reflection image of the subject's eye.

The fifteenth aspect example of the ophthalmic apparatus of the embodiment is the ophthalmic apparatus according to the fourteenth aspect example, wherein the second controller is further configured to perform one of or both the driving of the illumination polarizer and the driving of the photography polarizer such that the polarization direction of the illumination polarization component and the polarization direction of the photography polarization component become parallel to each other, to cause the photography system to generate a specular reflection image of the subject's eye.

The sixteenth aspect example of the ophthalmic apparatus of the embodiment is the ophthalmic apparatus according to the fifteenth aspect example, further including an image generating processor configured to generate an image of the subject's eye that contains no specular reflection noise based on the diffuse reflection image and the specular reflection image.

The seventeenth aspect example of the ophthalmic apparatus of the embodiment is the ophthalmic apparatus according to the fifteenth or sixteenth aspect example, further including an analyzing processor configured to perform a comparative analysis between the diffuse reflection image and the specular reflection image.

The eighteenth aspect example of the ophthalmic apparatus of the embodiment is the ophthalmic apparatus according to any of the first to seventeenth aspect examples, further including a polarization information generating processor configured to generate polarization information that represents a polarization state of the return light from the subject's eye based on the photography polarization component detected by the image sensor.

The nineteenth aspect example of the ophthalmic apparatus of the embodiment is the ophthalmic apparatus according to the eighteenth aspect example, wherein the photography system includes a first photography system and a second photography system, wherein the illumination system and the first photography system are configured to satisfy a Scheimpflug condition, the illumination system and the second photography system are configured to satisfy a Scheimpflug condition, the photography polarizer includes a first photography polarizer disposed in the first photography system and a second photography polarizer disposed in the second photography system, and the image sensor includes a first image sensor disposed in the first photography system and a second image sensor disposed in the second photography system.

The twentieth aspect example of the ophthalmic apparatus of the embodiment is the ophthalmic apparatus of the embodiment is the ophthalmic apparatus according to the nineteenth aspect example, wherein the polarization information generating processor is configured to generate the polarization information based on a first photography polarization component and a second photography polarization component, the first photography polarization component being extracted from first return light from the subject's eye by the first photography polarizer and detected by the first image sensor and the second photography polarization component being extracted from second return light from the subject's eye by the second photography polarizer and detected by the second image sensor.

The twenty first aspect example of the ophthalmic apparatus according to any of the eighteenth to twentieth aspect examples, further including: a movement mechanism configured to move the illumination system and the photography system; and a first controller configured to perform at least control of the photography system and control of the movement mechanism to cause the photography system to collect a series of images, wherein the polarization information generating processor is configured to generate the polarization information based on the series of images.

The twenty second aspect example of the ophthalmic apparatus of the embodiment is the ophthalmic apparatus according to any of the eighteenth to twenty first aspect examples, further including: a polarizer driving mechanism configured to perform one of or both driving of the illumination polarizer for changing a polarization direction of the illumination polarization component and driving of the photography polarizer for changing a polarization direction of the photography polarization component; and a second controller configured to control the polarizer driving mechanism to produce a relative change between the polarization direction of the illumination polarization component and the polarization direction of the photography polarization component, wherein the second controller is configured to control the polarizer driving mechanism such that two or more combinations of the polarization direction of the illumination polarization component and the polarization direction of the photography polarization component are produced, and the polarization information generating processor is configured to generate the polarization information based on two or more photography polarization components detected by the image sensor respectively corresponding to the two or more combinations.

The twenty third aspect example of the ophthalmic apparatus of the embodiment is the ophthalmic apparatus according to the twenty second aspect example, wherein the second controller is configured to control the polarizer driving mechanism such that a relative angle between the polarization direction of the illumination polarization component and the polarization direction of the photography polarization component has four values of 0 degrees, 45 degrees, 90 degrees, and 135 degrees, and the polarization information generating processor is configured to calculate Stokes parameters based on four photography polarization components detected by the image sensor respectively corresponding to the four values of the relative angle.

The twenty fourth aspect example of the ophthalmic apparatus of the embodiment is the ophthalmic apparatus according to any of the eighteenth to twenty third aspect examples, further including a visual information generating processor configured to generate visual information based on the polarization information generated by the polarization information generating processor.

The twenty fifth aspect example of the ophthalmic apparatus of the embodiment is the ophthalmic apparatus according to any of the first to twenty fourth aspect examples, wherein the photography polarizer includes a polarizing plate placed in an oblique manner with respect to an optical axis of the photography system.

The twenty sixth aspect example of the ophthalmic apparatus of the embodiment is the ophthalmic apparatus according to the twenty fifth aspect example, wherein the polarizing plate is placed parallel to a light receiving surface of the image sensor.

The twenty seventh aspect example of the ophthalmic apparatus of the embodiment is the ophthalmic apparatus according to the twenty fifth aspect example, wherein the polarizing plate is placed to be oriented in a direction between a first direction and a second direction, the first direction being perpendicular to the optical axis of the photography system and the second direction being parallel to the light receiving surface of the image sensor.

The twenty eighth aspect example of the ophthalmic apparatus of the embodiment is the ophthalmic apparatus according to any of the first to twenty seventh aspect examples, wherein the photography system includes a polarization camera that includes a polarizer array as the photography polarizer and a photodiode array as the image sensor.

As described in the present disclosure, an ophthalmic apparatus having any of the above non-limiting features is capable of providing an improvement in ophthalmic imaging.

In addition, those skilled in the art will understand that by combining any of the matters and/or items described in the present disclosure with an ophthalmic apparatus that has any of the above non-limiting features, it becomes possible not only to provide a further improvement in ophthalmic imaging, but also to provide various types and kinds of applications of ophthalmic imaging.

Other Embodiments

While described so far are some embodiments of an ophthalmic apparatus, embodiments according to the present disclosure are not limited to ophthalmic apparatuses. Examples of embodiments other than ophthalmic apparatuses include a method of controlling an ophthalmic apparatus, a computer program, and a recording medium. Similar to the embodiments of ophthalmic apparatuses, these embodiments can also provide an improvement in image quality of ophthalmic imaging.

A method of controlling an ophthalmic apparatus according to one embodiment provides a way how to control an ophthalmic apparatus.

The ophthalmic apparatus includes an illumination system configured to project slit illumination light onto a subject's eye, a photography system configured to perform photography of the subject's eye, a movement mechanism configured to move the illumination system and the photography system, and a processor. Further, the illumination system and the photography system are configured to satisfy a Scheimpflug condition. In addition, the illumination system includes a light source unit configured to output slit illumination light and an illumination polarizer configured to extract an illumination polarization component from the slit illumination light output by the light source unit, and the illumination system is configured to project the illumination polarization component extracted by the illumination polarizer onto the subject's eye as the illumination light. Furthermore, the photography system includes a photography polarizer configured to extract a photography polarization component from return light from the subject's eye with the slit illumination light projected and an image sensor configured to detect the photography polarization component extracted by the photography polarizer.

The method according to the present embodiment is configured to cause the processor included in the ophthalmic apparatus to execute at least control of the photography system and control of the movement mechanism, thereby causing the photography system to collect a series of images.

Any of the matters and/or items described in the present disclosure may be combined with the method according to the present embodiment.

A program according to one embodiment is for operating an ophthalmic apparatus.

This ophthalmic apparatus includes an illumination system configured to project slit illumination light onto a subject's eye, a photography system configured to perform photography of the subject's eye, a movement mechanism configured to move the illumination system and the photography system, and a processor. Further, the illumination system and the photography system are configured to satisfy a Scheimpflug condition. In addition, the illumination system includes a light source unit configured to output slit illumination light and an illumination polarizer configured to extract an illumination polarization component from the slit illumination light output by the light source unit, and the illumination system is configured to project the illumination polarization component extracted by the illumination polarizer onto the subject's eye as the illumination light. Furthermore, the photography system includes a photography polarizer configured to extract a photography polarization component from return light from the subject's eye with the slit illumination light projected and an image sensor configured to detect the photography polarization component extracted by the photography polarizer.

The program according to the present embodiment is configured to cause the processor included in the ophthalmic apparatus to execute at least control of the photography system and control of the movement mechanism, thereby causing the photography system to collect a series of images.

Any of the matters and/or items described in the present disclosure may be combined with the program according to the present embodiment.

A recording medium according to one embodiment is a computer-readable non-transitory recording medium that stores a program for operating an ophthalmic apparatus.

The ophthalmic apparatus includes an illumination system configured to project slit illumination light onto a subject's eye, a photography system configured to perform photography of the subject's eye, a movement mechanism configured to move the illumination system and the photography system, and a processor. Further, the illumination system and the photography system are configured to satisfy a Scheimpflug condition. In addition, the illumination system includes a light source unit configured to output slit illumination light and an illumination polarizer configured to extract an illumination polarization component from the slit illumination light output by the light source unit, and the illumination system is configured to project the illumination polarization component extracted by the illumination polarizer onto the subject's eye as the illumination light. Furthermore, the photography system includes a photography polarizer configured to extract a photography polarization component from return light from the subject's eye with the slit illumination light projected and an image sensor configured to detect the photography polarization component extracted by the photography polarizer.

The program stored in the recording medium according to the present embodiment is configured to cause the processor included in the ophthalmic apparatus to execute at least control of the photography system and control of the movement mechanism, thereby causing the photography system to collect a series of images.

Any of the matters and/or items described in the present disclosure may be combined with the recording medium according to the present embodiment.

A computer-readable non-transitory recording medium that can be used as a recording medium according to the present embodiment may be a recording medium of any form, and may be any of a magnetic disk, an optical disk, a magneto-optical disk, and a semiconductor memory.

Any of the matters and/or items described in embodiments of ophthalmic apparatuses may be combined with any embodiments of other categories than ophthalmic apparatuses.

In some examples, a matter or an item freely selected from various kinds of matters and/or items described as an optional aspect of an ophthalmic apparatus according to an embodiment may be combined with an embodiment of any category such as an embodiment of a method of controlling an ophthalmic apparatus, an embodiment of a program, or an embodiment of a recording medium.

In addition, any of the matters and/or items described in the present disclosure may be combined with an embodiment of any category such as an embodiment of a method of controlling an ophthalmic apparatus, an embodiment of a program, or an embodiment of a recording medium.

While certain embodiments have been described, these embodiments have been presented by way of example only, and are not intended to limit the scope of the inventions. Indeed, the novel embodiments described herein may be embodied in a variety of other forms; furthermore, various omissions, substitutions, additions and changes in the form of the embodiments described herein may be made without departing from the spirit of the inventions. The accompanying claims and their equivalents are intended to cover such forms or modifications as would fall within the scope and spirit of the inventions.

What is claimed is:

1. An ophthalmic apparatus comprising:
an illumination system configured to project illumination light onto a subject's eye; and
a photography system configured to perform photography of the subject's eye, wherein
the illumination system and the photography system are configured to satisfy a Scheimpflug condition,
the illumination system includes a light source unit configured to output slit illumination light and an illumination polarizer configured to extract an illumination polarization component from the slit illumination light output by the light source unit, and the illumination system is configured to project the illumination polarization component extracted by the illumination polarizer onto the subject's eye as the illumination light,
the photography system includes a photography polarizer configured to extract a photography polarization component from return light from the subject's eye with the slit illumination light projected and an image sensor configured to detect the photography polarization component extracted by the photography polarizer, and
the ophthalmic apparatus further comprising a polarizer driving mechanism configured to perform one of or both driving of the illumination polarizer for changing a polarization direction of the illumination polarization component and driving of the photography polarizer for changing a polarization direction of the photography polarization component.

2. The ophthalmic apparatus according to claim 1, further comprising a movement mechanism configured to move the illumination system and the photography system.

3. The ophthalmic apparatus according to claim 2, further comprising a first controller configured to perform at least control of the photography system and control of the movement mechanism to cause the photography system to collect a series of images.

4. The ophthalmic apparatus according to claim 1, further comprising:
an illumination polarizer moving mechanism configured to insert and remove the illumination polarizer into and from an optical path of the illumination system; and
a photography polarizer moving mechanism configured to insert and remove the photography polarizer into and from an optical path of the photography system.

5. The ophthalmic apparatus according to claim 4, wherein the polarizer driving mechanism includes a first polarizer driving mechanism configured to perform one of or both the driving of the illumination polarizer and the driving of the photography polarizer to produce a relative change between the polarization direction of the illumination polarization component and the polarization direction of the photography polarization component.

6. The ophthalmic apparatus according to claim 5, further comprising:
a movement mechanism configured to move the illumination system and the photography system; and
a first controller configured to perform at least control of the photography system and control of the movement mechanism to cause the photography system to collect a series of images.

7. The ophthalmic apparatus according to claim 6, wherein
the first controller is configured to control the movement mechanism to move the illumination system and the photography system in a predetermined movement direction, and
the first polarizer driving mechanism is configured to perform one of or both the driving of the illumination polarizer and the driving of the photography polarizer such that the polarization direction of the illumination polarization component becomes perpendicular to the predetermined movement direction and the polarization direction of the photography polarization component becomes parallel to the predetermined movement direction.

8. The ophthalmic apparatus according to claim 1, wherein the photography system includes a first photography system and a second photography system, wherein
the illumination system and the first photography system are configured to satisfy a Scheimpflug condition,
the illumination system and the second photography system are configured to satisfy a Scheimpflug condition,
the photography polarizer includes a first photography polarizer disposed in the first photography system and a second photography polarizer disposed in the second photography system, and
the image sensor includes a first image sensor disposed in the first photography system and a second image sensor disposed in the second photography system.

9. The ophthalmic apparatus according to claim 8, further comprising a second polarizer driving mechanism configured to perform one of or both the driving of the first photography polarizer and the driving of the second photography polarizer to produce a relative change between a polarization direction of a first photography polarization component and a polarization direction of a second photography polarization component, the first photography polarization component being extracted from first return light from the subject's eye by the first photography polarizer and the second photography polarization component being extracted from second return light from the subject's eye by the second photography polarizer.

10. The ophthalmic apparatus according to claim 9, further comprising:

a movement mechanism configured to move the illumination system and the photography system; and a first controller configured to perform at least control of the photography system and control of the movement mechanism to cause the photography system to collect a series of images.

11. The ophthalmic apparatus according to claim 10, wherein the first controller is configured to control the movement mechanism to move the illumination system and the photography system in a predetermined movement direction, the polarization direction of the illumination polarization component is oriented in a direction perpendicular to the predetermined movement direction, and the second polarizer driving mechanism is configured to perform one of or both the driving of the first photography polarizer and the driving of the second photography polarizer such that both the polarization direction of the first photography polarization component and the polarization direction of the second photography polarization component become parallel to the predetermined movement direction.

12. The ophthalmic apparatus according to claim 1, further comprising a second controller configured to control the polarizer driving mechanism to produce a relative change between the polarization direction of the illumination polarization component and the polarization direction of the photography polarization component, wherein the photography system is configured to generate an image of the subject's eye corresponding to a predetermined combination of the polarization direction of the illumination polarization component and the polarization direction of the photography polarization component.

13. The ophthalmic apparatus according to claim 12, wherein the second controller is configured to perform one of or both the driving of the illumination polarizer and the driving of the photography polarizer such that the polarization direction of the illumination polarization component and the polarization direction of the photography polarization component become perpendicular to each other, to cause the photography system to generate a diffuse reflection image of the subject's eye.

14. The ophthalmic apparatus according to claim 13, wherein the second controller is further configured to perform one of or both the driving of the illumination polarizer and the driving of the photography polarizer such that the polarization direction of the illumination polarization component and the polarization direction of the photography polarization component become parallel to each other, to cause the photography system to generate a specular reflection image of the subject's eye.

15. The ophthalmic apparatus according to claim 14, further comprising an image generating processor configured to generate an image of the subject's eye that contains no specular reflection noise based on the diffuse reflection image and the specular reflection image.

16. The ophthalmic apparatus according to claim 14, further comprising an analyzing processor configured to perform a comparative analysis between the diffuse reflection image and the specular reflection image.

17. The ophthalmic apparatus according to claim 1, further comprising a polarization information generating processor configured to generate polarization information that represents a polarization state of the return light from the subject's eye based on the photography polarization component detected by the image sensor.

18. The ophthalmic apparatus according to claim 17, wherein the photography system includes a first photography system and a second photography system, wherein the illumination system and the first photography system are configured to satisfy a Scheimpflug condition, the illumination system and the second photography system are configured to satisfy a Scheimpflug condition, the photography polarizer includes a first photography polarizer disposed in the first photography system and a second photography polarizer disposed in the second photography system, and the image sensor includes a first image sensor disposed in the first photography system and a second image sensor disposed in the second photography system.

19. The ophthalmic apparatus according to claim 18, wherein the polarization information generating processor is configured to generate the polarization information based on a first photography polarization component and a second photography polarization component, the first photography polarization component being extracted from first return light from the subject's eye by the first photography polarizer and detected by the first image sensor and the second photography polarization component being extracted from second return light from the subject's eye by the second photography polarizer and detected by the second image sensor.

20. The ophthalmic apparatus according to claim 17, further comprising:

a movement mechanism configured to move the illumination system and the photography system; and a first controller configured to perform at least control of the photography system and control of the movement mechanism to cause the photography system to collect a series of images, wherein the polarization information generating processor is configured to generate the polarization information based on the series of images.

21. The ophthalmic apparatus according to claim 17, further comprising:

a second controller configured to control the polarizer driving mechanism to produce a relative change between the polarization direction of the illumination polarization component and the polarization direction of the photography polarization component, wherein the second controller is configured to control the polarizer driving mechanism such that two or more combinations of the polarization direction of the illumination polarization component and the polarization direction of the photography polarization component are produced, and the polarization information generating processor is configured to generate the polarization information based on two or more photography polarization components detected by the image sensor respectively corresponding to the two or more combinations.

22. The ophthalmic apparatus according to claim 21, wherein the second controller is configured to control the polarizer driving mechanism such that a relative angle between the polarization direction of the illumination polarization component and the polarization direction of the photography polarization component has four values of 0 degrees, 45 degrees, 90 degrees, and 135 degrees, and the polarization information generating processor is configured to calculate Stokes parameters based on four photography polarization components detected by the image sensor respectively corresponding to the four values of the relative angle.

23. The ophthalmic apparatus according to claim 17, further comprising a visual information generating processor configured to generate visual information based on the polarization information generated by the polarization information generating processor.

24. The ophthalmic apparatus according to claim 1, wherein the photography polarizer includes a polarizing plate placed in an oblique manner with respect to an optical axis of the photography system.

25. The ophthalmic apparatus according to claim 24, wherein the polarizing plate is placed parallel to a light receiving surface of the image sensor.

26. The ophthalmic apparatus according to claim 24, wherein the polarizing plate is placed to be oriented in a direction between a first direction and a second direction, the first direction being perpendicular to the optical axis of the photography system and the second direction being parallel to the light receiving surface of the image sensor.

27. The ophthalmic apparatus according to claim 1, wherein the photography system includes a polarization camera that includes a polarizer array as the photography polarizer and a photodiode array as the image sensor.

28. A method of controlling an ophthalmic apparatus that includes an illumination system configured to project slit illumination light onto a subject's eye, a photography system configured to perform photography of the subject's eye, a movement mechanism configured to move the illumination system and the photography system, a polarizer driving mechanism, and a processor, wherein the illumination system and the photography system are configured to satisfy a Scheimpflug condition, the illumination system includes a light source unit configured to output slit illumination light and an illumination polarizer configured to extract an illumination polarization component from the slit illumination light output by the light source unit, the illumination system is configured to project the illumination polarization component extracted by the illumination polarizer onto the subject's eye as the illumination light, the photography system includes a photography polarizer configured to extract a photography polarization component from return light from the subject's eye with the slit illumination light projected and an image sensor configured to detect the photography polarization component extracted by the photography polarizer, and the polarizer driving mechanism is configured to perform one of or both driving of the illumination polarizer for changing a polarization direction of the illumination polarization component and driving of the photography polarizer for changing a polarization direction of the photography polarization component, the method comprising:

causing the processor to perform control of the polarizer driving mechanism to produce a relative change between the polarization direction of the illumination polarization component and the polarization direction of the photography polarization component; and causing the processor to perform at least control of the photography system and control of the movement mechanism to cause the photography system to collect a series of images.

29. A computer-readable non-transitory recording medium storing a program configured to cause a computer to execute control of an ophthalmic apparatus that includes an illumination system configured to project slit illumination light onto a subject's eye, a photography system configured to perform photography of the subject's eye, a movement mechanism configured to move the illumination system and the photography system, and a polarizer driving mechanism, wherein the illumination system and the photography system are configured to satisfy a Scheimpflug condition, the illumination system includes a light source unit configured to output slit illumination light and an illumination polarizer configured to extract an illumination polarization component from the slit illumination light output by the light source unit, the illumination system is configured to project the illumination polarization component extracted by the illumination polarizer onto the subject's eye as the illumination light, and the photography system includes a photography polarizer configured to extract a photography polarization component from return light from the subject's eye with the slit illumination light projected and an image sensor configured to detect the photography polarization component extracted by the photography polarizer, and the polarizer driving mechanism is configured to perform one of or both driving of the illumination polarizer for changing a polarization direction of the illumination polarization component and driving of the photography polarizer for changing a polarization direction of the photography polarization component, the program stored in the computer-readable non-transitory recording medium comprising:

an instruction for causing the processor to perform control of the polarizer driving mechanism to produce a relative change between the polarization direction of the illumination polarization component and the polarization direction of the photography polarization component; and an instruction for causing the computer to perform at least control of the photography system and control of the movement mechanism to cause the photography system to collect a series of images.

* * * * *